(12) United States Patent
Agrawal et al.

(10) Patent No.: US 11,836,853 B2
(45) Date of Patent: *Dec. 5, 2023

(54) GENERATION AND PRESENTATION OF PREDICTED PERSONALIZED THREE-DIMENSIONAL BODY MODELS

(71) Applicant: Amazon Technologies, Inc., Seattle, WA (US)

(72) Inventors: Amit Kumar Agrawal, Santa Clara, CA (US); Jinjin Li, San Jose, CA (US); Rohith Mysore Vijaya Kumar, Sunnyvale, CA (US); Dylan John Drover, Mountain View, CA (US); Brandon Michael Smith, Fremont, CA (US); Prakash Ramu, Portland, OR (US); Ram Sever, Sunnyvale, CA (US); Apoorv Chaudhri, Cupertino, CA (US); Visesh Uday Kumar Chari, Santa Cruz, CA (US); Sunil Sharadchandra Hadap, Dublin, CA (US); Rajesh Gautam, Cupertino, CA (US)

(73) Assignee: Amazon Technologies, Inc., Seattle, WA (US)

( * ) Notice: Subject to any disclaimer, the term of this patent is extended or adjusted under 35 U.S.C. 154(b) by 75 days.

This patent is subject to a terminal disclaimer.

(21) Appl. No.: 17/377,214

(22) Filed: Jul. 15, 2021

(65) Prior Publication Data

US 2021/0343074 A1  Nov. 4, 2021

Related U.S. Application Data

(63) Continuation of application No. 16/584,360, filed on Sep. 26, 2019, now Pat. No. 11,069,131.

(51) Int. Cl.
*G06T 17/00* (2006.01)
*A61B 5/00* (2006.01)
(Continued)

(52) U.S. Cl.
CPC ............ *G06T 17/00* (2013.01); *A61B 5/4872* (2013.01); *G06T 15/005* (2013.01); *G06T 15/80* (2013.01); *G06T 19/20* (2013.01); *G06T 2210/41* (2013.01)

(58) Field of Classification Search
None
See application file for complete search history.

(56) References Cited

U.S. PATENT DOCUMENTS

| 8,918,162 B2 | 12/2014 | Prokoski |
| 8,982,147 B2 | 3/2015 | Ramani et al. |

(Continued)

FOREIGN PATENT DOCUMENTS

| CA | 2831674 A1 | 4/2005 |
| CA | 2884668 A1 | 9/2016 |
| CN | 109409348 A | 3/2019 |

OTHER PUBLICATIONS

Anguelov, D., Srinivasan, P., Koller, D., Thrun, S., Rodgers, J. and Davis, J., "SCAPE: Shape Completion and Animation of People," ACM Trans. Graph. (Proc. SIGGRAPH), 24(3):408-416, Jul. 2005, 9 pages, http://robots.stanford.edu/papers/anguelov.shapecomp.pdf.

(Continued)

*Primary Examiner* — Frank S Chen
(74) *Attorney, Agent, or Firm* — Athorus, PLLC

(57) ABSTRACT

Described are systems and methods directed to generation of a personalized three-dimensional ("3D") body model of a body, such as a human body, based on two-dimensional ("2D") images of that body and the generation and presentation of predicted personalized 3D body models of the body (Continued)

when one or more body measurements (e.g., body fat, body weight, muscle mass) are changed. For example, a user may provide a target body measurement value and the implementations will generate one or more predicted personalized 3D body models representative of a predicted appearance of the body with the target body measurement value.

20 Claims, 33 Drawing Sheets

(51) Int. Cl.
    G06T 15/00    (2011.01)
    G06T 15/80    (2011.01)
    G06T 19/20    (2011.01)

(56) References Cited

U.S. PATENT DOCUMENTS

| | | | |
|---|---|---|---|
| 10,489,683 | B1 | 11/2019 | Koh et al. |
| 2004/0151366 | A1 | 8/2004 | Nefian et al. |
| 2011/0234581 | A1* | 9/2011 | Eikelis .......... G06T 19/006 345/419 |
| 2013/0325493 | A1 | 12/2013 | Wong et al. |
| 2014/0340479 | A1 | 11/2014 | Moore et al. |
| 2016/0247017 | A1 | 8/2016 | Sareen et al. |
| 2016/0284123 | A1 | 9/2016 | Hare et al. |
| 2018/0089821 | A1 | 3/2018 | Koldyshev |
| 2019/0122424 | A1 | 4/2019 | Moore et al. |
| 2019/0191137 | A1 | 6/2019 | Bisti |
| 2020/0193710 | A1 | 6/2020 | Talgorn et al. |

OTHER PUBLICATIONS

Anonymous: "BMI 3D", www.bmi3d.de; Nov. 25, 2018 (Nov. 25, 2018), XP002801424,URL: https://web.archive.org/web/20181125231845/https://www.bmi3d.de/rechner.html [Retrieved from the Internet on Dec. 16, 2020]; the whole document.
Anonymous: "Documentation: What is MakeHuman?", MakeHuman, May 20, 2016 (May 20, 2016), XP002801426, URL: http://www.makehumancommunity.org/wiki/Documentation:Whatis MakeHuman%3F [Retrieved from the Internet on Jan. 30, 2021]; the whole document.
Anonymous: "Virtual Weight Loss Simulator", www.changeinseconds. com; Dec. 11, 2016 (Dec. 11, 2016), XP002801425, URL: https://web.archive.org/web/20161206202928;%20/http://www. changeinseconds.com/simulator/ [Retrieved from the Internet on Dec. 16, 2020]; the whole document.
Balan, A. O. and Black, M. J., "The Naked Truth: Estimating Body Shape under Clothing," In European Conference on Computer Vision (ECCV), 2008, 15 pages, https://www.researchgate.net/profile/Michael_Black6/publication/221305001_The_Naked_Truth_Estimating_Body_Shape_Under_Clothing/links/0fcfd512d21f538458000000/The-Naked-Truth-Estimating-Body-Shape-Under-Clothing pdf?orgin=publication_detail.
Bălan, A. O., Sigal, L., Black, M. J., Davis, J. E. and Haussecker, H. W., "Detailed Human Shape and Pose from Images," In IEEE Conference on Computer Vision and Pattern Recognition (CVPR), 2007, 9 pages.
Bogo, F., Kanazawa, A., Lassner, C., Gehler, P., Romero, J. and Black, M. J., "Keep it SMPL: Automatic Estimation of 3D Human Pose and Shape from a Single Image," In European Conference on Computer Vision (ECCV), 2016, 21 pages, https://arxiv.org/pdf/1607.08128v1.pdf.
Boisvert, J., Shu, C., Wuhrer, S., and Xi, P., "Three-Dimensional Human Shape Inference from Silhouettes: Reconstruction and Validation," Machine Vision and Applications, 24(1):145-157, 2013, 13 pages, http://people.scs.carleton.ca/~c_shu/Publications/silhouettes_human_rec_MVA11.pdf.
Bukar et al., "Automatic age and gender classification using supervised appearance model," Journal of Electronic Imaging, Aug. 2016; 25(6):0601605, 12 pages.
Chen, W., Wang, H., Li, Y., Su, H., Wang, Z., Tu, C., Lischinski, D., Cohen-Or, D. and Chen, B. Synthesizing Training Images for Boosting Human 3D Pose Estimation. In 2016 Fourth International Conference on 3D Vision (3DV) Oct. 25, 2016 (pp. 479-488). IEEE, 10 pages.
Chen, X., Guo, Y Zhou, B. and Zhao, Q., "Deformable Model for Estimating Clothing and Naked Human Shapes from a Single Image," The Visual Computer, 29(11):1187-1196, 2013, 10 pages.
Chen, Y., Kim, T.-K. and Cipolla, R., "Inferring 3D Shapes and Deformations from Single Views," In European Conference on Computer Vision, 2010, 14 pages.
Chen, Y., Kim, T.-K. and Cipolla, R., Silhouette-Based Object Phenotype Recognition Using 3D Shape Priors. In Inter-national Conference on Computer Vision (ICCV), 2011, 8 pages.
Devries, T. and Taylor, G. W., Learning Confidence for Out-of-Distribution Detection in Neural Networks, arXiv preprint arXiv:1802.04865, 2018, 12 pages.
Dibra, E., Jain, H., Öztireli, C., Ziegler, R. and Gross, M., "HSNets: Estimating Human Body Shape from Silhouettes with Convolutional Neural Networks," In International Conference on 3D Vision (3DV), 2016, 10 pages.
Dibra, E., Jain, H., Öztireli, C., Ziegler, R. and Gross, M., "Human Shape from Silhouettes Using Generative HKS Descriptors and Cross-Modal Neural Networks," In IEEE Conference on Computer Vision and Pattern Recognition (CVPR), 2017, 11 pages.
Dibra, E., Jain, H., Öztireli, C., Ziegler, R. and Gross, M., "Shape from Selfies: Human Body Shape Estimation Using CCA Regression Forests," In European Converence on Computer Vision (ECCV), 2016, 17 pages.
Gilbert, A., Volino, M., Collomosse, J. and Hilton, A.,"Volumetric Performance Capture from Minimal Camera View-Points," In European Conference on Computer Vision, 2018, 16 pages.
Gong, K., Liang, X., Zhang, D., Shen, X. and Lin, L., "Look into Person: Self-Supervised Structure-Sensitive Learning and a New Benchmark for Human Parsing," In IEEE Conference on Computer Vision and Pattern Recognition (CVPR), 2017, 9 pages.
Guan, P., Weiss, A., Bălan, A. O. and Black, M. J., "Estimating Human Shape and Pose from a Single Image," In IEEE International Conference on Computer Vision (ICCV), 2009, 8 pages.
Güler, R. A., Neverova, N. and Kokkinos, I., "DensePose: Dense Human Pose Estimation in the Wild," In IEEE Conference on Computer Vision and Pattern Recognition (CVPR), 2018, 10 pages.
He, K., Zhang, X., Ren, S. and Sun, J., "Deep Residual Learning for Image Recognition," In IEEE Conference on Computer Vision and Pattern Recognition (CVPR), 2016, 9 pages.
Hirano, D., Funayama, Y. and Maekawa, T. 3D Shape Reconstruction From 2D Images. Computer-Aided Design and Applications. 2009 CAD Solutions, LLC. Jan. 1, 2009 ;6(5):701-10, 10 pages.
Hiorprasert, T., Harwood, D. and Davis, L. S., "A Statistical Approach for Real-Time Robust Background Subtraction and Shadow Detection," In IEEE International Conference on Computer Vision (ICCV), 1999, 19 pages.
International Search Report and Written Opinion dated Dec. 23, 2020, issued in corresponding International Application No. PCT/US2020/052569.
Joo, H., Simon, T. and Y. Sheikh, Y., "Total Capture: A 3D Deformation Model for Tracking Faces, Hands, and Bodies," In IEEE Conference on Computer Vision and Pattern Recognition (CVPR), 2018, 10 pages.
Kanazawa, A., Black, M. J., Jacobs, D. W. and Malik, J., "End-to-End Recovery of Human Shape and Pose," In IEEE Conference on Computer Vision and Pattern Recognition (CVPR), 2018, 10 pages.
Krasin, I., Duerig, T., Alldrin, N., Ferrari, V., Abu-El-Haija, S., Kuznetsova, A., Rom, H., Uijlings, J., Popov, S., Kamali, S., Malloci, M., Pont-Tuset, J., Veit, A., Belongie, S., Gomes, V., Gupta, A., Sun, C., Chechik, G., Cai, D., Feng, Z., Narayanan, D., and Murphy, K., "Openimages: A Public Dataset for Large-Scale Multi-Label and Multi-Class Image Classification," Dataset available from https://storage.googleapis.com/openimages/web/index. html, 2017.

(56) References Cited

OTHER PUBLICATIONS

Kundu, A., Li, Y. and Rehg, J. M., "3D-RCNN: Instance-Level 3D Object Reconstruction via Render-and-Compare," In IEEE Conference on Computer Vision and Pattern Recognition (CVPR), 2018, 10 pages.

Lassner, C., Romero, J., Kiefel, M., Bogo, F., Black, M. J. and Gehler, P. V., "Unite the People—Closing the Loop Between 3D and 2D Human Representations," In IEEE Conference on Computer Vision and Pattern Recognition (CVPR), 2017, 10 pages.

Long, J., Shelhamer, E., and Darrell, T., "Fully Convolutional Networks for Semantic Segmentation, "In IEEE Conference on Computer Vision and Pattern Recognition (CVPR), 2015, 10 pages.

Loper, M., Mahmood, N., Romero, J., Pons-Moll, G. and Black, M. J., "SMPL: A Skinned Multi-Person Linear Model," ACM Trans. Graphics (Proc. SIGGRAPH Asia), 34(6):248:1-248:16, Oct. 2015, 16 pages.

Mülayim, A. Y., Yilmaz, U. and Atalay, V. Silhouette-based 3D Model Reconstruction from Multiple Images. IEEE Transactions on Systems, Man, and Cybernetics, Part B (Cybernetics). Jul. 22, 2003;33(4):582-91, 27 pages.

Nakedlabs.com, Aug. 2, 2018 (Aug. 2, 2018), XP002801423, URL: https://web.archive.org/web/20180802014000/https://nakedlabs com/ [Retrieved from the Internet: Dec. 16, 2020]; the whole document.

Ngiam, J., Khosla, A., Kim, M., Nam, J., Lee, H.and Ng, A. Y., "Multimodal Deep Learning," In International Conference on Machine Learning (ICML), pp. 689-696, 2011, 8 pages.

Nguyen et al., "Gender Recognition from Human-Body Images Using Visible-Light and Thermal Camera Videos Based on a Convolutional Neural Network for Image Feature Extraction," Sensors,Mar. 2017:17(3);637, 22 pages.

Omran, M., Lassner, C., Pons-Moll, G., Gehler, P. V. and Schiele, B., "Neural Body Fitting: Unifying Deep Learning and Model-Based Human Pose and Shape Estimation," In International Conference on 3D Vision (3DV), 2018, 14 pages.

Park, S., Hwang, J. and Kwak, N. 3D Human Pose Estimation Using Convolutional Neural Networks with 2D Pose Information. In European Conference on Computer Vision, Sep. 8, 2016 (pp. 156-169), https://arxiv.org/pdf/1608.03075v2.pdf, 15 pages.

Pavlakos et al., "Expressive Body Capture: 3D Hands, Face, and Body from a Single Image," 2019 IEEE/CVF Conference on Computer Vision and Pattern Recognition (CVPR), Jun. 1, 2019, 11 pages.

PAvlakos, G., Zhu, L., Zhou, X. and Daniilidis, K., "Learning to Estimate 3D Human Pose and Shape from a Single Color Image," In IEEE Conference on Computer Vision and Pattern Recognition (CVPR), 2018, 10 pages.

Popa, A.-I., Zanfir, M. and C. Sminchisescu, C., "Deep Multitask Architecture for Integrated 2D and 3D Human Sensing," In IEEE Conference on Computer Vision and Pattern Recognition (CVPR), 2017, 10 pages.

Rhodin, H., Robertini, N., Casas, D., Richardt, C., Seidel, H.-P. and Theobalt, C., "General Automatic Human Shape and Motion Capture Using Volumetric Contour Cues," In European Conference on Computer Vision, 2016, 18 pages.

Robinette, K. M., Blackwell, S., Daanen, H., Boehmer, M., Fleming, S., Brill, T., Hoeferlin, D. and Burnsides, D., "Civilian American and European Surface Anthropometry Resource (CAESAR) Final Report," Tech. Rep. AFRL-HEWP-TR-2002-0169, US Air Force Research Laboratory, 2002, 70 pages.

Rogez, G., Weinzaepfel, P. and Schmid C. LCR-Net++: Multi-Person 2D and 3D Pose Detection in Natural Images. IEEE IEEE Transactions on Pattern Analysis and Machine Intelligence, Jan. 14, 2019;42(5): 1146-61, Downloaded on Jul. 18, 2020, 16 pages.

Sigal, L., Bălan, A. O. and Black, M. J., "Combined Discriminative and Generative Articulated Pose and Non-Rigid Shape Estimation," In Neural Information Processing Systems (NIPS), 2007, 8 pages.

Su et al., "Multi-view Convolutional Neural Networks for 3D Shape Recognition," 2015 IEEE International Conference on Computer Vision (ICCV), Dec. 7-13, 2015, Santiago, Chile, 9 pages.

Sun, J., Ovsjanikov, M. and Guibas, L., "A Concise and Provably Informative Multi-Scale Signature Based on Heat Diffusion," In Symposium on Geometry Processing, 2009, 10 pages.

Sun, X., Wu, J., Zhang, X., Zhang, Z., Zhang, C., Xue, T., Tenenbaum, J. B. and Freeman, W. T. Pix3D: Dataset and Methods for Single-Image 3D Shape Modeling. In 2018 IEEE/CVF Conference on Computer Vision and Pattern Recognition, Jun. 18, 2018 (pp. 2974-2983). IEEE, 10 pages.

Tan, J. K. V., Budvytis, I. and Cipolla, R., "Indirect Deep Structured Learning for 3D Human Body Shape and Pose Prediction," In British Machine Vision Conference, 2017, 11 pages.

TC2 Labs LLC, "SizeUSA", 3 pages, http://scan2fit.com/sizeusa/about.php.

Rome, D., Russell, C. and Agapito, L. Lifting from the Deep: Convolutional 3D Pose Estimation from a Single Image. In Proceedings of the IEEE Conference on Computer Vision and Pattern Recognition 2017 (pp. 2500-2509), 11 pages.

Varol, G., Ceylan, D Russell, B., Yang, J., Yumer, E., Laptev, I. and Schmid, C., "BodyNet: Volumetric Inference of 3D Human Body Shapes," In European Conference on Computer Vision (ECCV), 2018, 17 pages.

Varol, G., Romero, J., Martin, X., Mahmood, N., Black, M. J., Laptev, I. and Schmid, C., "Learning from Synthetic Humans," In IEEE Conference on Computer Vision and Pattern Recognition (CVPR), 2017, 9 pages.

Xi, P., Lee, W.-S. and Shu, C., "A Data-Driven Approach to Human-Body Cloning Using a Segmented Body Database," In Pacific Conference on Computer Graphics and Applications (PG), 2007, 9 pages.

Xie, H., Yao, H., Sun, X., Zhou, S. and Zhang, S. Pix2Vox: Context-aware 3D Reconstruction from Single and Multi-View Images. arXiv preprint arXiv: 1901.11153, https://arxiv.org/pdf/1901.11153.pdf, Jul. 29, 2019, 9 pages.

Yu, F., Zhang, Y., Song, S., Seff, A., and Xiao, J., "LSUN: Construction of a Large-Scale Image Dataset Using Deep Learning with Humans in the Loop," arXiv preprint arXiv:1506.03365, 2015, 9 pages.

Zanfir, A., Marinoiu, E. and Sminchisescu, C., "Monocular 3D Pose and Shape Estimation of Multiple People in Natural Scenes—the Importance of Multiple Scene Constraints," In IEEE Conference on Computer Vision and Pattern Recognition (CVPR), 2018, 10 pages.

Zhang, H., Dana, K., Shi, J., Zhang, Z., Wang, X., Tyagi, A. and Agrawal, A., "Context Encoding for Semantic Segmentation," In The IEEE Conference on Computer Vision and Pattern Recognition (CVPR), Jun. 2018, 10 pages.

Search Report dated Nov. 25, 2022, for corresponding CN Application No. 2020800677735, 4 pages.

Dibra Endri et al.: "HS-Nets: Estimating Human Body Shape from Silhouettes with Convolutional Neural Networks", 2016 Fourth International Conference on 3D Vision (30V), IEEE, Oct. 25, 2016 (Oct. 25, 2016), pp. 108-117, XP033027616, DOI: 10.1109/3DV.2016.19 [retrieved on Dec. 15, 2016].

EPO Search Report from Office action dated May 17, 2023, issued in corresponding EP Application No. 20789364.5.

Haritosh, Ankur et al."A Novel Method to Estimate Height, Weight and Body Mass Index from Face Images", 2019 Twelfth International Conference on Contemporary Computing (IC3), IEEE, Aug. 8, 2019 (Aug. 8, 2019), pp. 1-6, XP033618825, DOI: 10.1109/IC3.2019.8844872 [retrieved on Sep. 18, 2019].

Pantanowitz, Adam et al.: "Estimation of Body Mass Index from Photographs using Deep Convolutional Neural Networks", arxiv.org, Cornell University Library, 201 Olin Librarycornell University Ithaca, Ny 14853, Aug. 29, 2019 (Aug. 29, 2019), XP081489793.

* cited by examiner

GENERATION AND PRESENTATION OF PREDICTED PERSONALIZED THREE-DIMENSIONAL BODY MODELS

PRIORITY CLAIM

This application is a Continuation of U.S. patent application Ser. No. 16/584,360, filed Sep. 26, 2019, and titled "Predictive Personalized Three-Dimensional Body Models," the contents of which are herein incorporated by reference in their entirety.

BACKGROUND

Three-dimensional modeling of the human body currently requires large or expensive sensors, such as stereo imaging elements, three-dimensional scanners, depth sensing devices, etc.

DETAILED DESCRIPTION

As is set forth in greater detail below, implementations of the present disclosure are directed to the collection of two-dimensional ("2D") body images of a body of a user, generation and presentation of a personalized three-dimensional ("3D") body model of the body of the user based on those 2D body images, and the generation and presentation of different predicted personalized 3D body models of the body of the user at different body measurements (e.g., different body fat percentages, different muscle mass amounts, different body weights, etc.).

For example, an application executing on a portable device that includes a 2D camera, such as cell phones, tablets, laptops, etc., may provide instructions to a user and collect 2D body images of a body of the user from different body directions. In other implementations, the 2D body images may be obtained from any other source. Those 2D body images may be sent by the application to remote computing resources that process the 2D body images to determine personalized 3D body parameters, to generate a personalized 3D body model of the body of the user, and/or to determine body measurements of the body of the user. Body measurements include, but are not limited to, body composition (e.g., weight, body fat, bone mass, body mass, body volume, etc.). Body parameters includes, but are not limited to, shape vector of the body, pose, body dimensions (e.g., arm length, leg length, arm circumference, leg circumference, shoulder width, shoulder circumference, waist width, waist circumference, torso width, torso circumference, body height, etc.), texture/color, etc.

The application executing on the portable device receives the current body measurement information and personalized 3D body parameters, generates the personalized 3D body model, and presents some or all of the body measurements and the personalized 3D body model to the user. The user may interact with the personalized 3D body model to view different sides of the personalized 3D body model and/or to visualize differences in the personalized 3D body model if one or more body measurements change. For example, a user may provide a target body measurement, such as a decrease in body fat, and the disclosed implementations may generate one or more predicted personalized 3D body models that represent a predicted appearance of the body of the user with the target body measurement(s). In some implementations, the predicted appearance of the body may be presented as a 3D body slider and/or other adjustor that the user may interact with the view progressive changes to the body appearance at different body measurements.

Figure 1A:
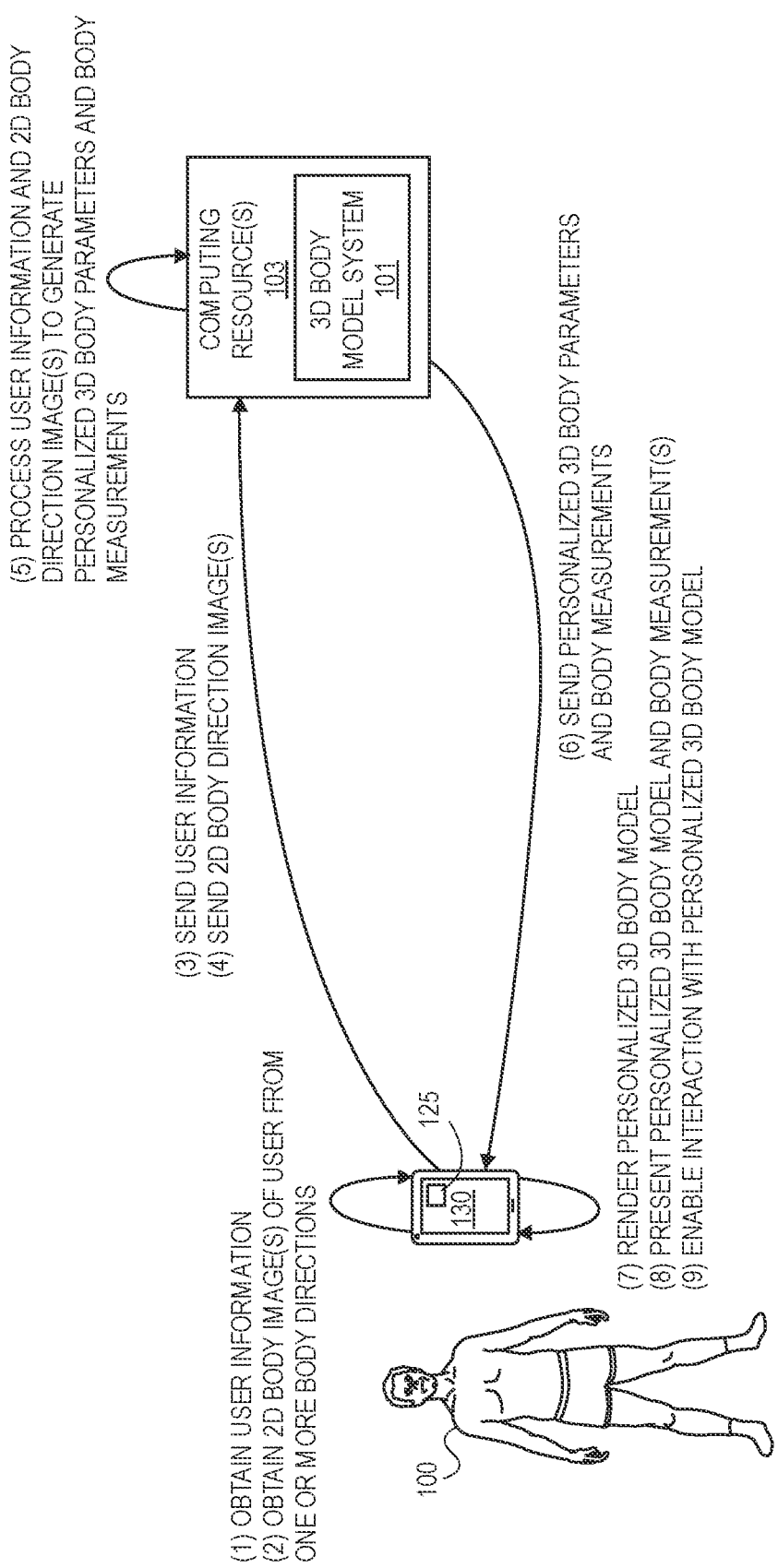
FIGS. 1A through 1B are a transition diagram of two-dimensional body image collection and processing to produce a personalized three-dimensional body model of that body that is presented back to the user, in accordance with implementations of the present disclosure.
Figure 1B:
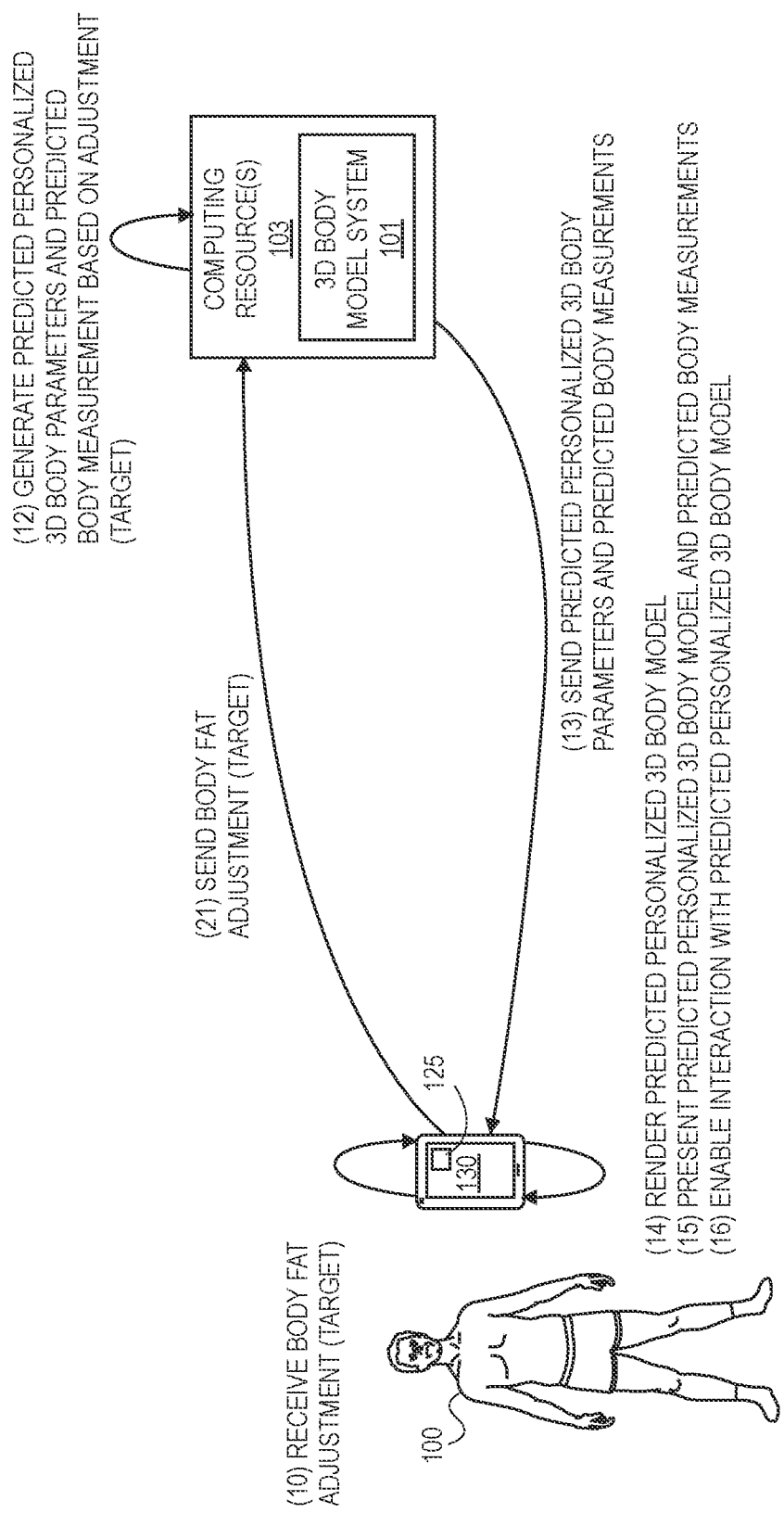
Figure 2:
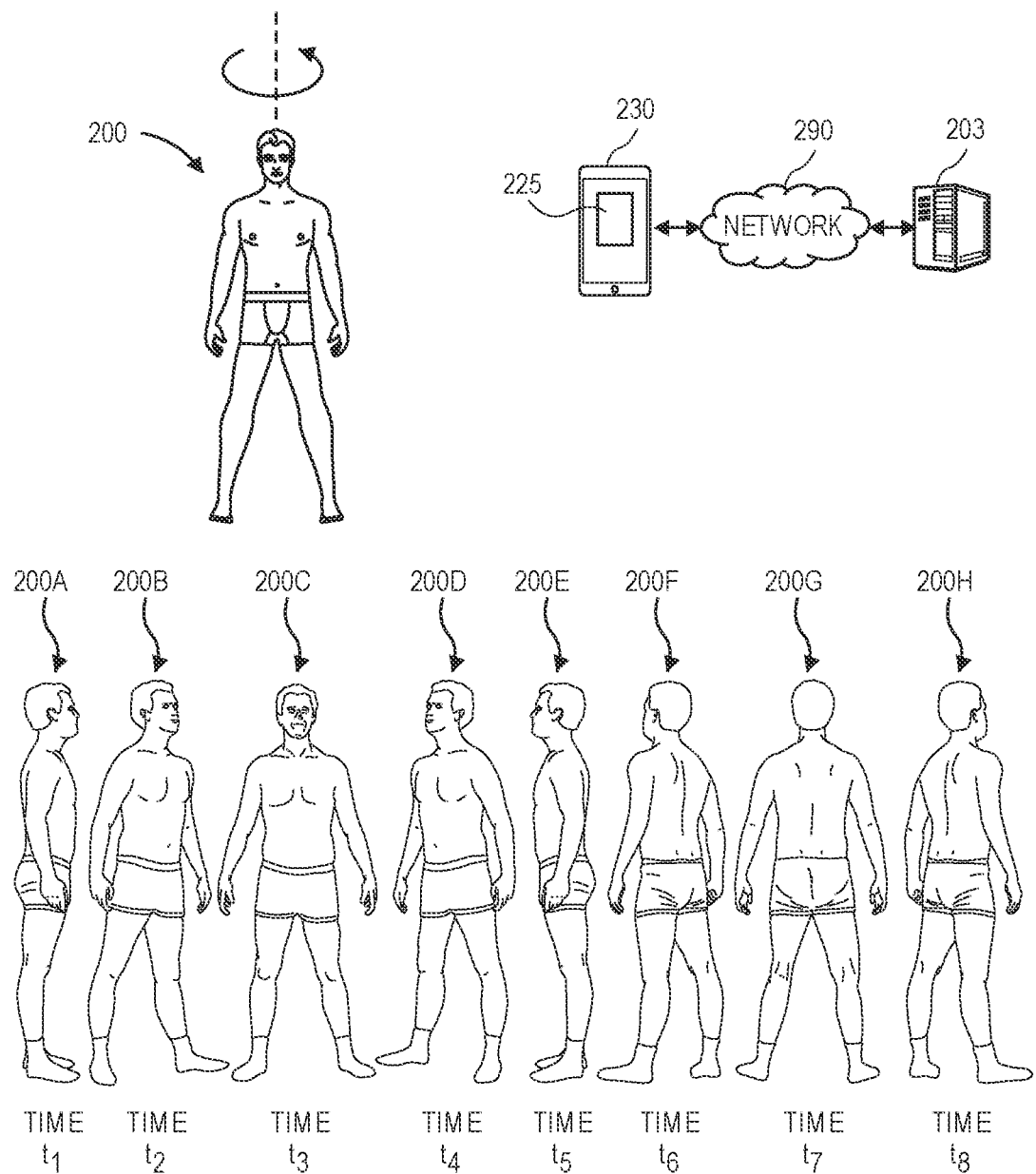
FIG. 2 illustrates different body directions of a body that may be captured in two-dimensional body images and used to produce a personalized three-dimensional body model, in accordance with implementations of the present disclosure.

FIG. 1A is a transition diagram of 2D body image collection and processing to produce a personalized 3D body model of a body of a user 100 that is presented back to the user, FIG. 1B is a transition diagram of a generation of a predicted 3D body model, and FIG. 2 illustrates examples of different orientations or body directions of a body 200, in accordance with implementations of the present disclosure.

In some implementations, a user 100/200 may execute an application 125/225 on a portable device 130/230, such as a cellular phone, tablet, laptop, etc., that includes an imaging element (e.g., camera) and interact with the application. The imaging element may be any conventional imaging element, such as a standard 2D Red, Green, Blue ("RGB") digital camera that is included on many current portable devices. Likewise, images, as discussed herein may be still images generated by the imaging element and/or images or frames extracted from video generated by the imaging element.

The user may provide user information, such as username, password, etc., to the application so that the application can identify the user and determine a user account associated with the user. Likewise, the user may provide other user information, such as body measurements, including but not limited to weight, height, age, gender, ethnicity, etc. The user may select which user information is provided or choose not to provide any user information. In addition, in some implementations, the user may interact with the application executing on the portable device 130/230 without providing any user identifying information (e.g., operate as a guest to the application).

Upon user identification and/or receipt of user information, the user 100/200 positions the portable device 130/230 such that a field of view of the imaging element of the portable device is substantially horizontal and facing toward the user. In some implementations, the application 125/225 executing on the portable device 130/230 may provide visual and/or audible instructions that guide the user 100/200 in the placement and positioning of the portable device 130/230. For example, the application may instruct the user 100/200 to place the portable device 130/230 between waist and head height of the user and in a substantially vertical direction (e.g., between 2 and 10 degrees of vertical) such that the imaging element is pointed toward the user and the field of view of the imaging element is substantially horizontal.

In some implementations, the application may request that the user wear a minimal amount of clothing, such as undergarments shown in FIGS. 1A, 1B, and 2. By wearing minimal clothing, processing of the 2D body image may be more accurate.

Once the portable device is properly positioned, 2D body images of the user 100/200 are captured by the imaging element of the portable device 130/230. As discussed in more detail below, those 2D body images are processed to determine that the user is in a defined pose, such as an "A Pose," and to determine a body direction of the body of the user with respect to the camera. The defined pose may be any body position that enables image capture of components of the body. In one example, the defined pose is an "A Pose" in which the arms are separated from the sides of the body and the legs are separated, for example by separating the feet of the body to about shoulder width. The A Pose allows image processing of 2D body images to distinguish between body parts (e.g., legs, arms, torso) from different angles and also aids in body direction determination. The body direction may be any direction or orientation of the body with respect to the imaging element. Example body directions include, but are not limited to, a front side body direction in which the body is facing the imaging element, a right side body direction in which the body is turned such that a right side of the body is facing the imaging element, a left side body direction in which a left side of the body is facing the imaging element, and a back side body direction in which a back of the body is facing the imaging element. As will be appreciated, any number of body directions and corresponding orientations of the body may be utilized with the disclosed implementation and the four discussed (front side, right side, back side, and left side) are provided only as examples.

In some implementations, the application 125/225 executing on the portable device 130/230 may guide the user through different body directions and select one or more 2D images as representative of each body direction. For example, referring to FIG. 2, an application 225 executing on the portable device 230 may guide the user into the proper pose, such as the "A Pose" illustrated by the body 200 of the user and then guide the user through a series of body directions 200A, 200B, 200C, 200D, 200E, 200F, 200G, and 200H in which the user rotates their body to the requested body direction and remains in the A Pose while 2D body images are generated and one or more of those 2D body images are selected by the application as a 2D body direction image corresponding to the current body direction of the body of the user. In the example illustrated in FIG. 2, eight different 2D body direction images are selected by the application 225 executing on the portable device 230, one for each respective body direction 200A, 200B, 200C, 200D, 200E, 200F, 200G, and 200H. Determination of the proper defined pose and body direction and subsequent 2D body direction image selection are discussed in further detail below.

Returning back to FIG. 1A, as each 2D body direction image is selected by the application, or after all 2D body direction images are selected, the 2D body direction images are sent from the application 125/225 executing on the portable device 130/230 via a network 290 (FIG. 2) to remote computing resources 103/203 for further processing. In addition, the user information provided to the application by the user 100/200 may be sent from the application executing on the portable device 130/230 to the remote computing resources 103/203. In other implementations, all processing may be done on the portable device. In still other examples, as images are generated, the images may be sent to the remote computing resources 103/203 and processed by the remote computing resources 103/203 to select the body direction images.

The remote computing resources 103/203 may include a 3D body model system 101/201 that receives the user information and/or the 2D body direction images and processes those images using one or more neural networks, such as a convolutional neural network, to generate personalized 3D body parameters corresponding to a personalized 3D body model of the body of the user 100/200. In addition, one or more of the 2D body direction images, such as front side 2D body direction image may be processed to determine one or more additional body measurements, such as body fat percentage, body mass, bone density, muscle mass, etc.

The 3D body model system 101/201, upon generating the personalized 3D body parameters and body measurements, sends the personalized 3D body parameters and body measurements back to the application 125/225 executing the portable device 130/230. The application 125/225, upon receipt of the personalized 3D body parameters and the body measurements, generates from the personalized 3D body parameters a personalized 3D body model that is representative of the body 100/200 of the user and presents the personalized 3D body model and body measurements on a display of the portable device 130/230.

In addition to rendering and presenting the personalized 3D body model and body measurements, the user 100/200 can interact with the presented personalized 3D body model and body measurements. For example, the user may view historical information that was previously collected for the user via the application 125/225. The user may also interact with the presented personalized 3D body model to rotate and/or turn the presented personalized 3D body model. For example, if the portable device 130/230 includes a touch-based display, the user may use the touch-based display to interact with the application and rotate the presented personalized 3D body model to view different views (e.g., front, side, back) of the personalized 3D body model.

In some implementations, as part of interaction with the application 125/225, the user 100/200 may provide one or more adjustments to body measurements, referred to herein as targets. For example, a user may request to alter the body fat measurement value of the body by a defined amount (e.g., from 25% to 20%), alter the muscle mass by a defined amount, alter the body weight a defined amount, etc. In other implementations, in addition to altering one or more body measurements, the user may specify one or more activities (e.g., exercise, nutrition, sleep) that should cause adjustments to one or more body measurements.

In the example illustrated in FIG. 1B, the user provides a body fat measurement adjustment to a target body fat measurement value. Upon receipt of the target body fat measurement value, the application 125/225 executing on the portable device 130/230 sends the target body fat measurement value to the remote computing resources 103/203 for further processing. The remote computing resources and the 3D body model system 101/201 process the received target body fat measurement value along with other current body measurements and the personalized 3D body parameters to generate predicted personalized 3D body parameters and predicted body measurements that correspond to the target body fat measurement value.

The remote computing resources 103/203 may then send the predicted personalized 3D body parameters and predicted body measurements to the application 125/225 and the application 125/225 may render a predicted 3D body model based on the received predicted personalized 3D body parameters. Similar to the personalized 3D body model, the application 125/225 may present the predicted 3D body model and the predicted body measurements to the user and enable interaction by the user with the predicted personalized 3D body model and/or the predicted body measurements. As discussed further below, in some implementations, the user may be able to alter views between the personalized 3D body model and the predicted personalized 3D body model. In other implementations, the application may integrate the personalized 3D body model and the predicted personalized 3D body model to produce a 3D body slider and/or other adjustor (e.g., radio button, dial, etc.) that provides the user with a continuous view of different appearances of the body at different body measurements between the current body measurements and the predicted body measurements. The 3D body slider and/or other adjustor, which relates to any type of controller or adjustor that may be used to present different appearances of the body at different body measurements is referred to herein generally as a "3D body model adjustor."

Figure 3A:
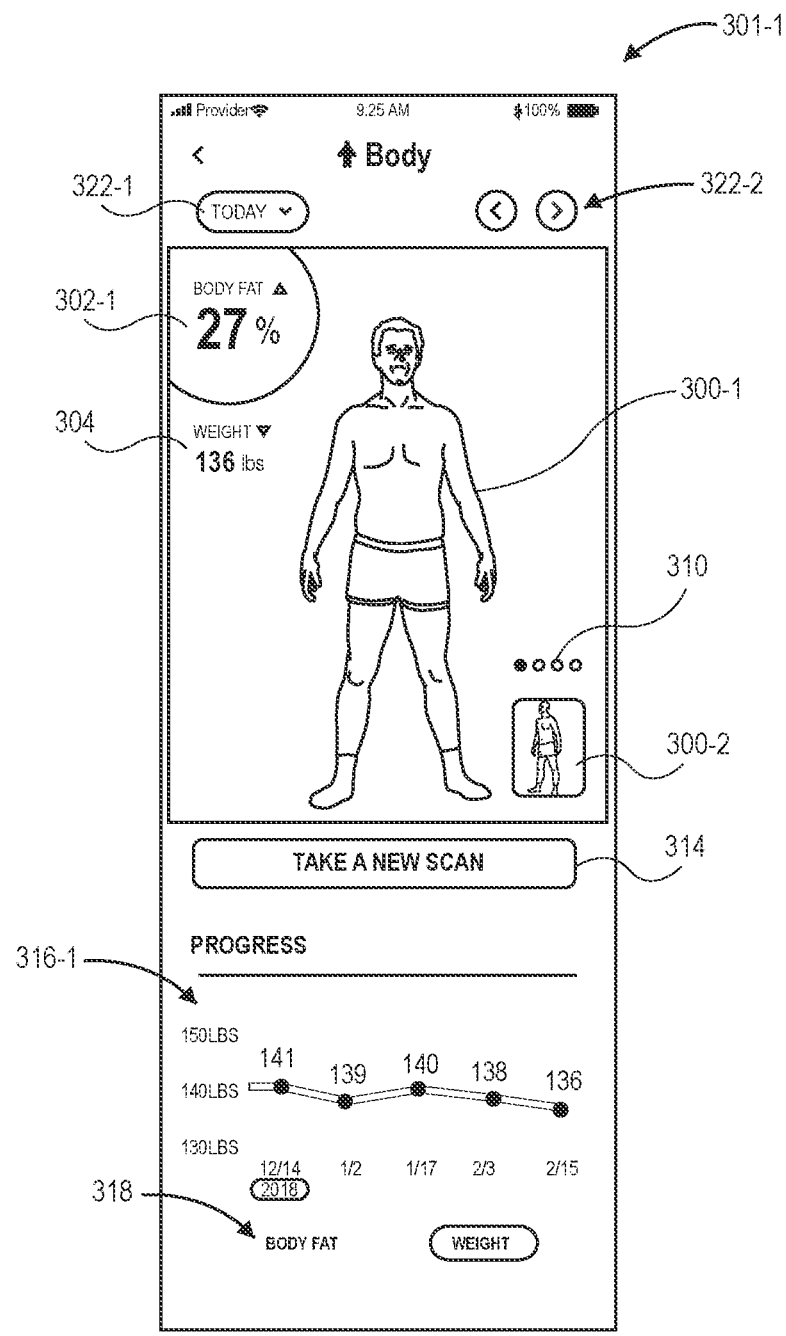
FIG. 3A is a user interface illustrating a captured two-dimensional body image and corresponding body measurement information determined from at least the two-dimensional body image, in accordance with implementations of the present disclosure.

FIG. 3A is a user interface 301-1 presented by an application executing on a portable device, such as the application 125 executing on the portable device 130 discussed above with respect to FIGS. 1A, 1B, and 2, in accordance with implementations of the present disclosure.

Figure 3B:
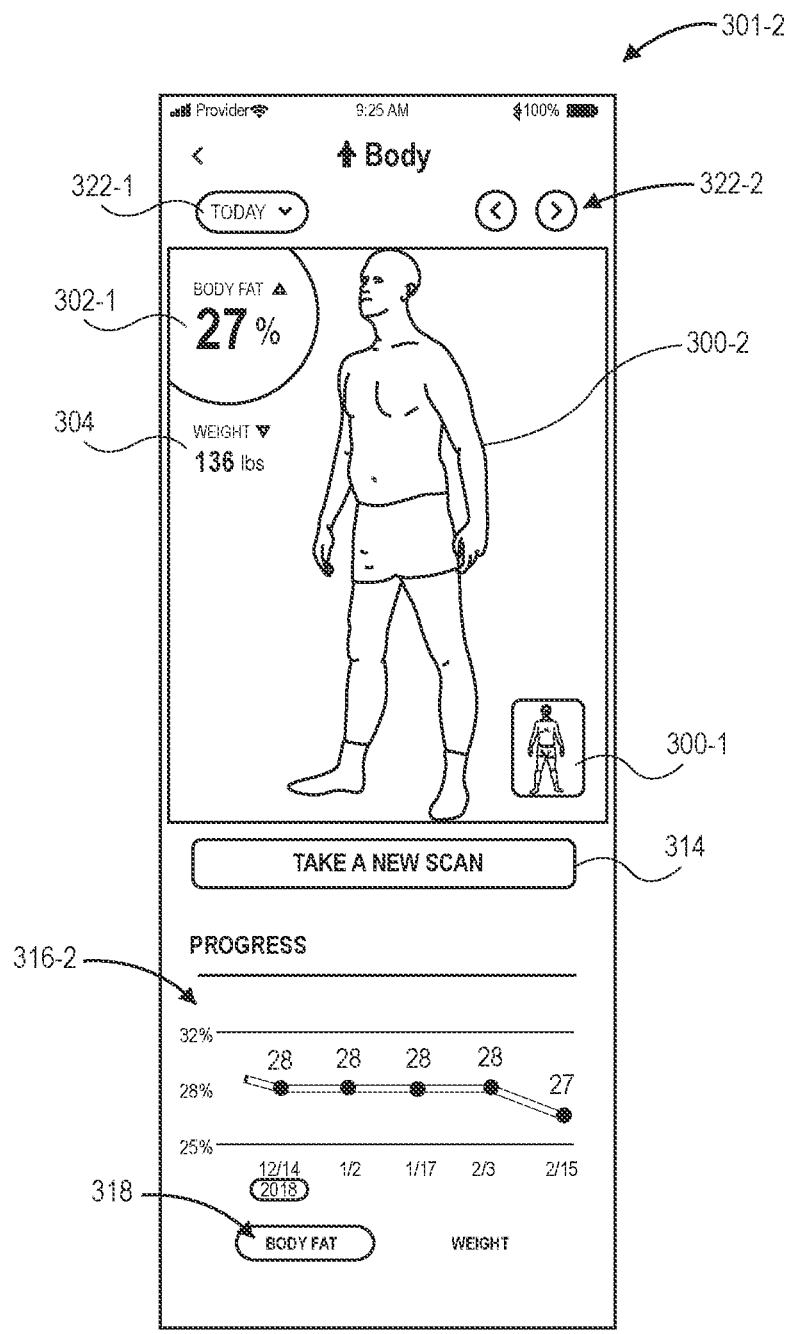
FIG. 3B is a user interface illustrating a personalized three-dimensional body model and corresponding body measurement information generated from a two-dimensional body image, in accordance with implementations of the present disclosure.

In this example, the user interface 301-1 illustrates a 2D body direction image 300-1 captured by an imaging element of the portable device that was used to generate and present a personalized 3D body model and corresponding body measurement information. In this example, the illustrated user interface 301-1 shows the 2D body direction image, the body fat percentage 302-1 determined for the body, and the weight 304 of the body, which may be determined from the 2D model image 300-1 and/or provided as user information by the user. In other implementations, additional or fewer body measurements may be presented on the user interface 301-1 by the application. A user interacting with the user interface 301-1 may also select to view other 2D body direction images that were used to generate a personalized 3D body model and/or body measurements, by selecting the indicators 310 and/or swiping or otherwise indicating with the user interface 301-1 to alter the currently presented 2D body direction image 300-1. The user may also alternate between a view of 2D body direction images 300-1, as illustrated in the user interface 301-1 of FIG. 3A and the rendered and presented personalized 3D body model 300-2, as illustrated in the small image presentation of the personalized 3D body model 300-2 in FIG. 3A and as illustrated as the primary image 300-2 in user interface 301-2 of FIG. 3B. Referring briefly to FIG. 3B, the user may interact with to rotate and/or change the view of the personalized 3D body model 300-2 by directly interacting with the personalized 3D body model 300-2. For example, the user may rotate the presentation of the personalized 3D body model to view different portions of the personalized 3D body model, zoom out to view more of the personalized 3D body model, or zoom in to view details corresponding to a portion of the personalized 3D body model.

In some implementations, if the user has utilized the application over a period of time to generate multiple instances of personalized 3D body models of the user, the user interface may also present historical body measurements 316 corresponding to the different dates in which 2D body images of the body of the user were captured and used to generate a personalized 3D body model and body measurements of the body of the user. In the illustrated example, the user may select between viewing historical body weight 316-1 illustrated in FIG. 3A and body fat percentage 316-2, as illustrated in FIG. 3B, through selection of the toggle control 318. In other implementations, different or additional historical body measurements 316 may be accessible through the user interface 301.

In addition to viewing historical body measurements 316, the user may also access and view either the 2D body images that were collected at those prior points in time and/or view the personalized 3D body models generated from those prior 2D body images, through selection of the date control 322-1 or the arrow control 322-2.

The user may also interact with the user interface 301 to select to take a new scan of their body by selecting the Take A New Scan control 314. In response to a user selecting the Take A New Scan control 314, the application executing on the portable device will provide instructions to the user to position the user in the defined pose (e.g., A Pose) and at proper body directions so that 2D body direction images can be generated and used to produce a personalized 3D body model of the body of the user, as discussed herein.

In some implementations, a user may also interact with the application to predict an appearance of the body with different body measurements (e.g., changes in body fat percentage and/or changes in muscle mass).

Figure 3C:
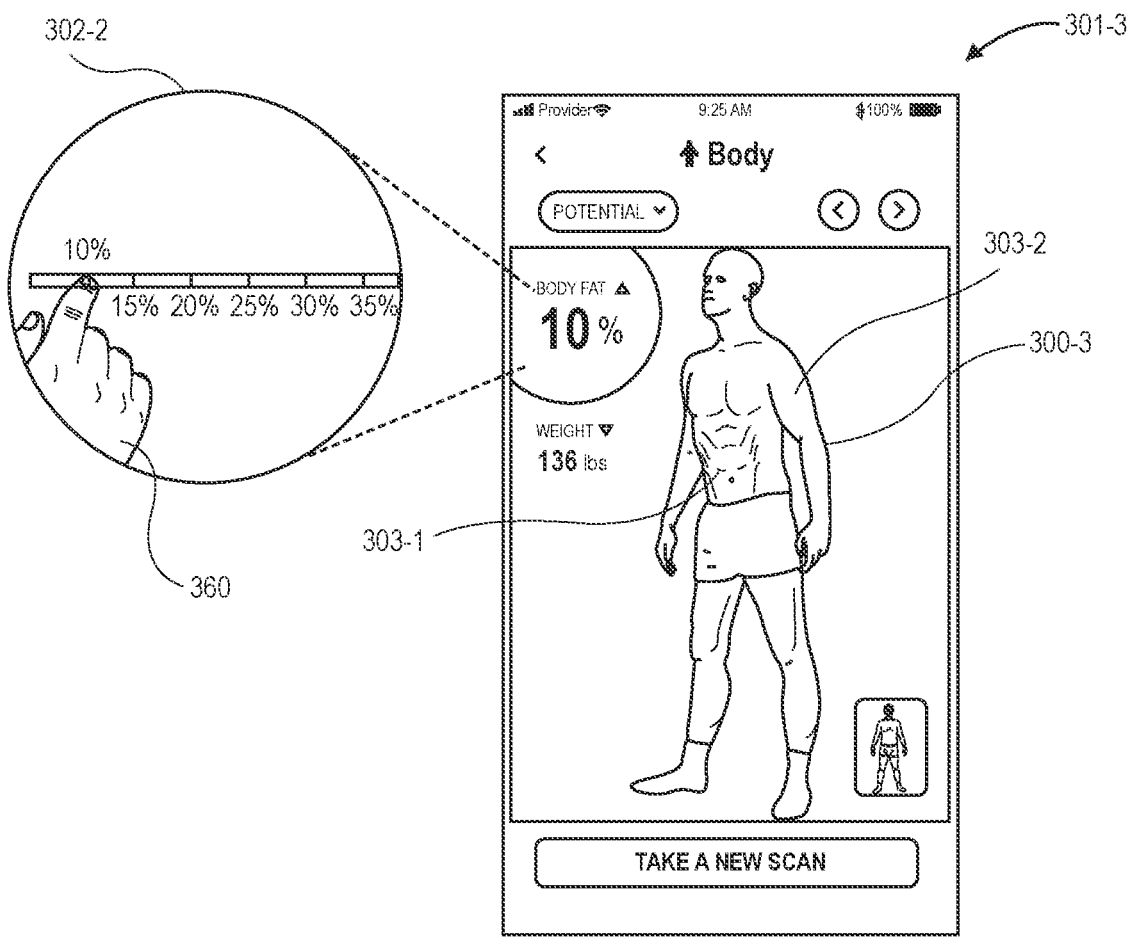
FIG. 3C is a user interface illustrating an example 3D body model adjustor in the form of a slider adjustment and resulting predicted personalized three-dimensional body model and corresponding body measurement, in accordance with implementations of the present disclosure.

For example, FIG. 3C is a user interface illustrating an example 3D body model adjustor in the form of a slider adjustment and resulting predicted three-dimensional body model and corresponding body measurement, in accordance with implementations of the present disclosure. As illustrated, a user may interact with the user interface 301-3 to alter one or more body measurements and the application executing on the device will generate a predicted personalized 3D body model 300-3 in accordance with the altered body measurements, in accordance with implementations of the present disclosure. In the illustrated example, the user is using their hand 360 to interact with a single slider 302-2 presented on the user interface 301-3 to alter the body fat measurement value, in this example from the computed 27% to 10%.

In response to receiving the target body measurement, in this example the reduced body fat measurement value, the disclosed implementations, as discussed further below, generate and present a predicted personalized 3D body model 300-3 and predicted body measurements representative of a predicted appearance of the body of the user with the target body measurement. The predicted personalized 3D body model 300-3 may be predicted and rendered based on the personalized 3D body model and corresponding personalized 3D body parameters determined for the body of the user. Likewise, shading and contours, such as shading to show stomach muscle definition 303-1 or size changes, such as increased arm size 303-2 may be generated and applied to aid in the presentation of the predicted personalized 3D body model.

Like the other rendered and presented personalized 3D body models, the user may interact with the presented predicted personalized 3D body model 300-3 to view different portions or aspects of the predicted personalized 3D body model.

While the example illustrated in FIG. 3C shows alteration of the body fat percentage, in other examples, a user may select to alter other body measurements, such as body weight, muscle mass, etc. Likewise, in some examples, based on a change to one body measurement, other body measurements may be automatically changed to correspond to the changed body measurement. For example, if the user changes the body fat percentage from 27% to 10%, as in the illustrated example, the application executing on the portable device may determine that in most instances a change in that amount of body fat percentage also typically results in a weight change from the determined 136 pounds to 115 pounds. The user may accept this anticipated change to other body measurements, provide other inputs for those body measurements, or select to leave those body measurements unchanged.

In still other examples, a user may be able to interact with a multi-dimensional slider and specify different changes to body measurements and/or activities. In some implementations, some or all of the sliders of the multi-dimensional slider may be interconnected such that a change to one slider may results in a change or adjustment to another slider. In other implementations, other forms of multi-dimensional 3D body model adjustors may also be presented.

Figure 3D:
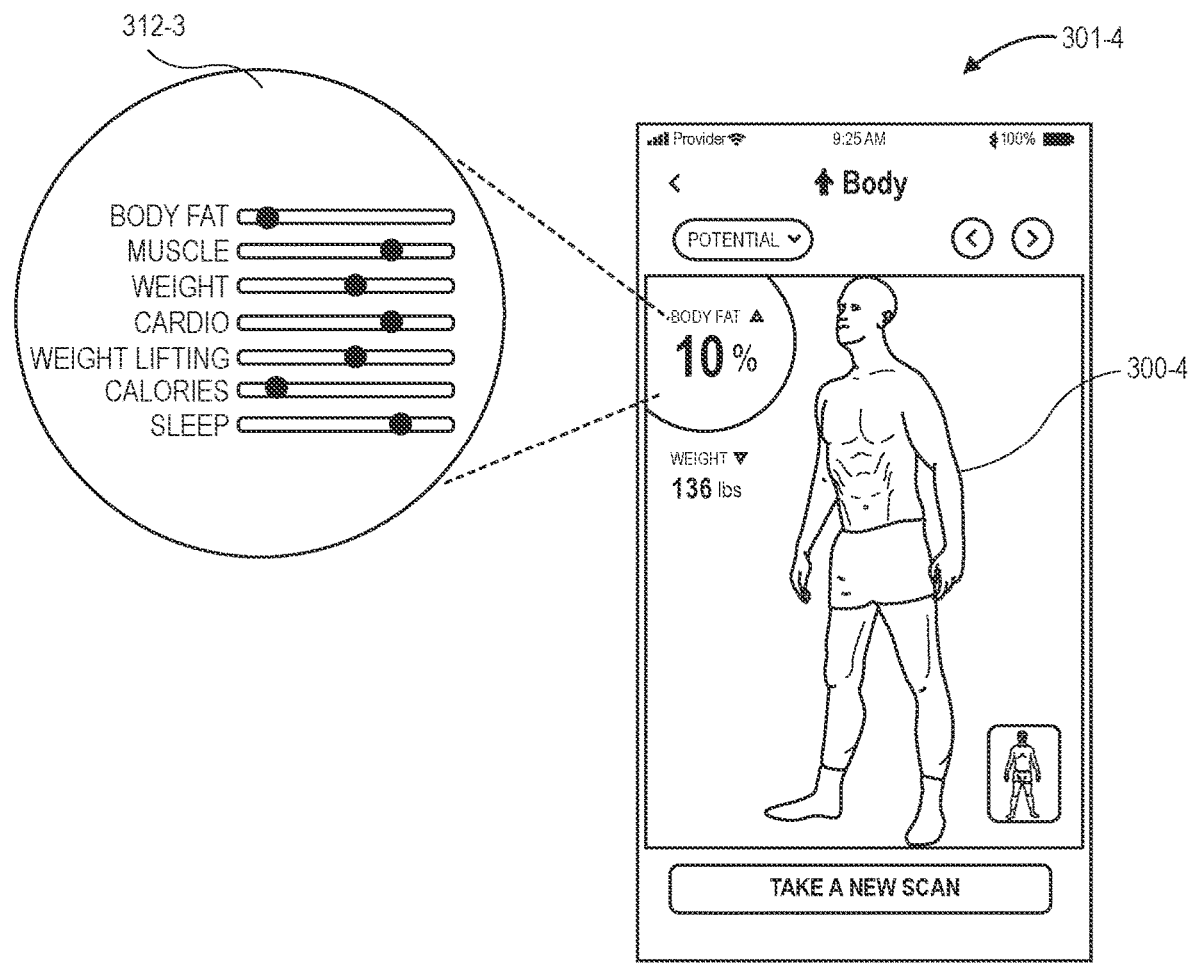
FIG. 3D is a user interface illustrating another example 3D body model adjustor in the form of a multi-dimensional slider adjustment and resulting predicted personalized three-dimensional body model and corresponding body measurement, in accordance with implementations of the present disclosure.

FIG. 3D is a user interface 301-4 illustrating another example 3D body model adjustor in the form of a multi-dimensional slider 312-3 adjustment and resulting predicted personalized 3D body model 300-4, in accordance with implementations of the present disclosure. In this example, the user may interact with a multi-dimensional slider 312-3 to adjust one or more body measurements and/or activity levels. In this example, the user may adjust the body fat measurement value, muscle mass measurement of the body, weight of the body, the amount of time they do cardio exercises, lift weights, the number of calories consumed, and/or the number of hours the user sleeps. In other implementations, the sliders may represent other body measurements (e.g., muscle mass, weight, etc.) and/or other activities that may be changed by the user and utilized by the disclosed implementations as targets for use in computing predicted personalized 3D body parameters and corresponding predicted personalized 3D body models.

Figure 4:
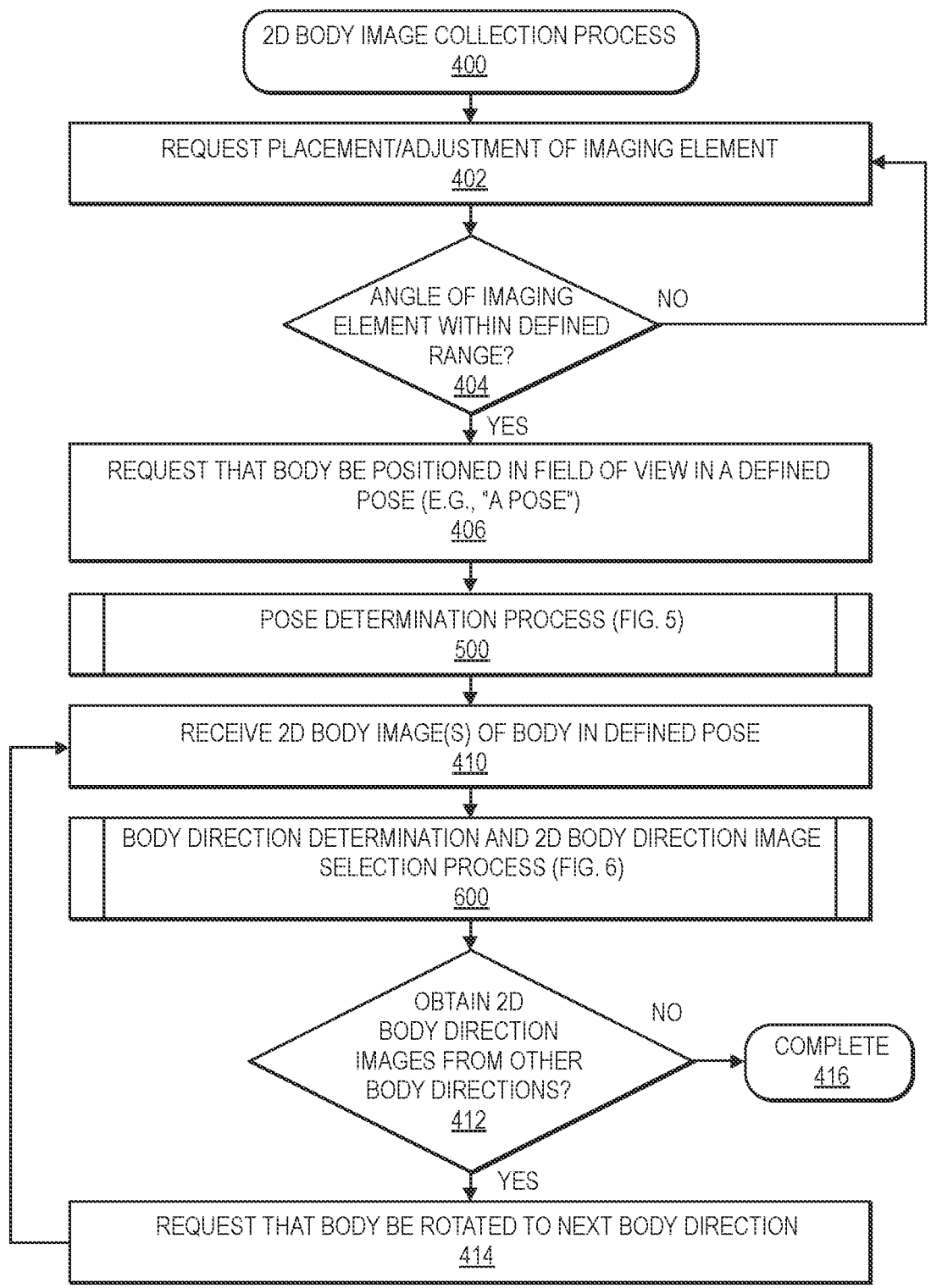
FIG. 4 is an example two-dimensional body image collection process, in accordance with implementations of the present disclosure.

FIG. 4 is an example 2D body image collection process 400, in accordance with implementations of the present disclosure. In some implementations, the example process 400 may be performed by an application executing on a portable device, such as the application 125 executing on the portable device 130 as discussed above with respect to FIGS. 1A, 1B, and 2. In other implementations, the example process 400 may be performed by one or more remote computing resources that receives images from the portable device and sends information/messages to the portable device. In still other examples, a portion of the example process 400 may be performed on the portable device and another portion may be performed by the remote computing resources.

The example process 400 begins, for example, when a user interacting with an application executing on a portable device requests to have a personalized 3D body model of their body generated. When the process 400 initiates, a request is presented (visually and/or audibly) that an imaging element, such as a camera, or the portable device that includes the imaging element, be positioned at a height, such as between the knees of the body and the head of the body (e.g., between two feet and six feet) and oriented such that the field of view of the portable device is substantially horizontal and oriented toward the body, as in 402. For example, the application executing on the mobile device may present a visual and/or audible output requesting that the portable device be placed within two and five degrees of vertical at about waist height such that the imaging element of the portable device is substantially horizontal and oriented toward the body of the user.

As the imaging element/portable device is placed into position, a determination is made as to whether the angle of the imaging element/portable device is within a defined range, as in 404. For example, data from one or more inputs of the portable device, such as an accelerometer, may be received and processed to determine an angle of the portable device and thus, the angle of the imaging element. The defined range may be any range at which image distortion does not impact the processing of the images to generate the personalized 3D body model, as discussed herein. For example, the defined range may be between zero degrees and ten degrees from vertical. In other implementations, the defined range may be more than zero degrees (e.g., two degrees) to reduce chances of the device falling over due to lack of stability. Likewise, in some implementations the upper bound of the defined range may be less or more than ten degrees. In some instances, the defined range may be greater than or equal to the range or angle indicated in the request to the user for placement of the imaging element/portable device.

If it is determined that the angle of the imaging element is not within the defined range, the example process 400 returns to block 402 and requests adjustment of the imaging element/portable device until the imaging element/portable device is at an angle that is within the defined range. For example, visual, tactile, and/or audible feedback may be presented by the portable device that includes the imaging element to guide the user in positioning the imaging element within the defined range.

Once it is determined that the angle of the imaging element/portable device is within the defined range, a confirmation message may be sent to the user and/or a request may be presented, audibly and/or visually, that the body to be scanned be positioned in the field of view of the imaging element in a defined pose, such as the "A Pose," as in 406. Any defined pose may be requested. When the user is in the A Pose, their arms are slightly separated from their torso and their legs are separated about shoulder width apart such that both their arms and their legs are slightly splayed out diagonally. The A Pose may be particularly beneficial as it separates the body appendages (arms, legs) from each other and from the body core/torso so that image processing can properly identify and define the parts of the body and body point locations, as discussed further below.

In some implementations, the focal point of the imaging element may also be adjusted based on the position of the body in the field of view of the imaging element. For example, rather than focusing on the entire image, the example process 400 may cause the imaging element to adjust the focal point to focus on the body of the user. Likewise, the exposure of the imaging element may be adjusted based on the lighting of the body of the user within the field of view of the imaging element.

Figure 5:
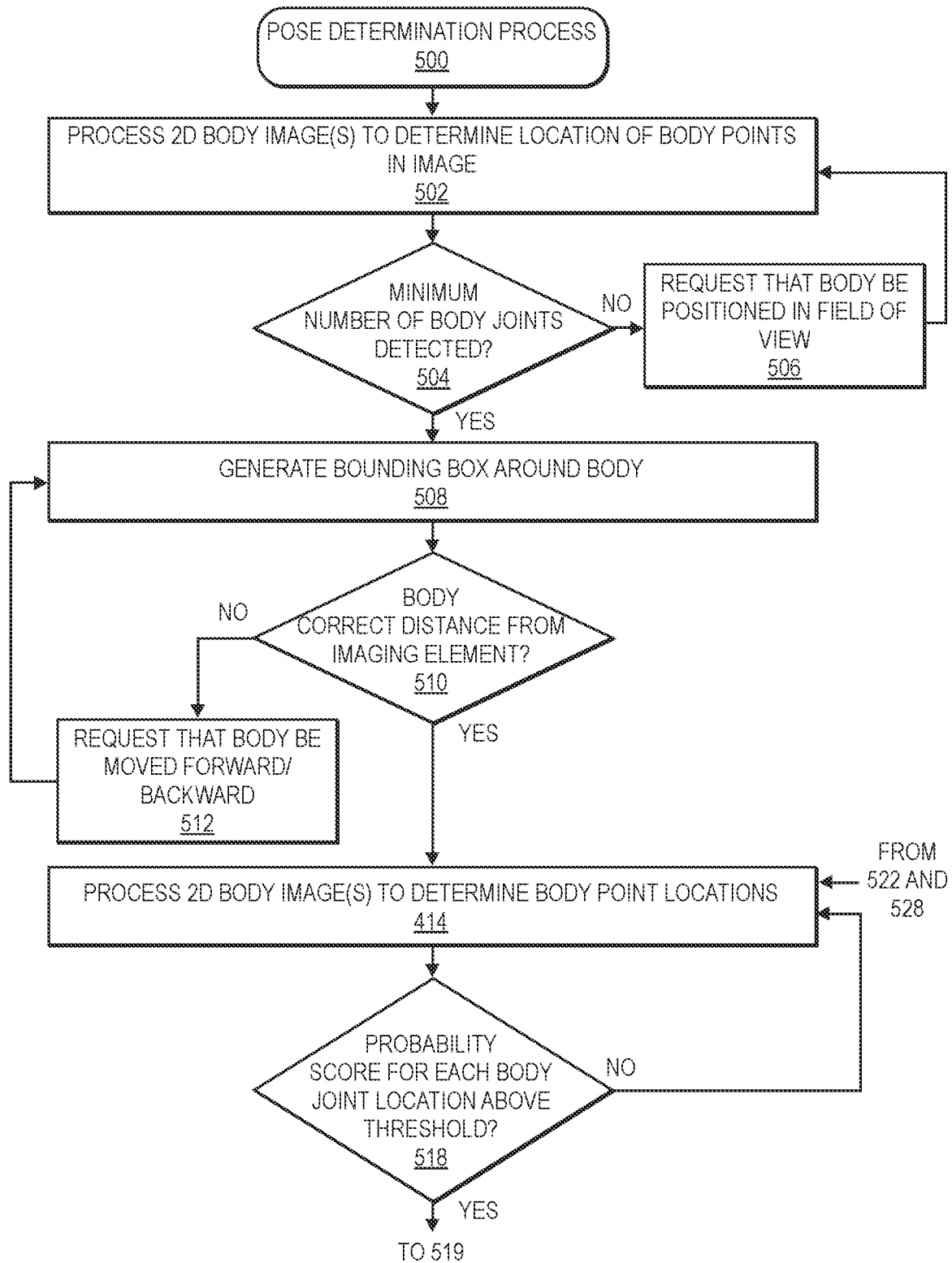
FIG. 5 is an example pose determination process, in accordance with implementations of the present disclosure.
Figure 5:
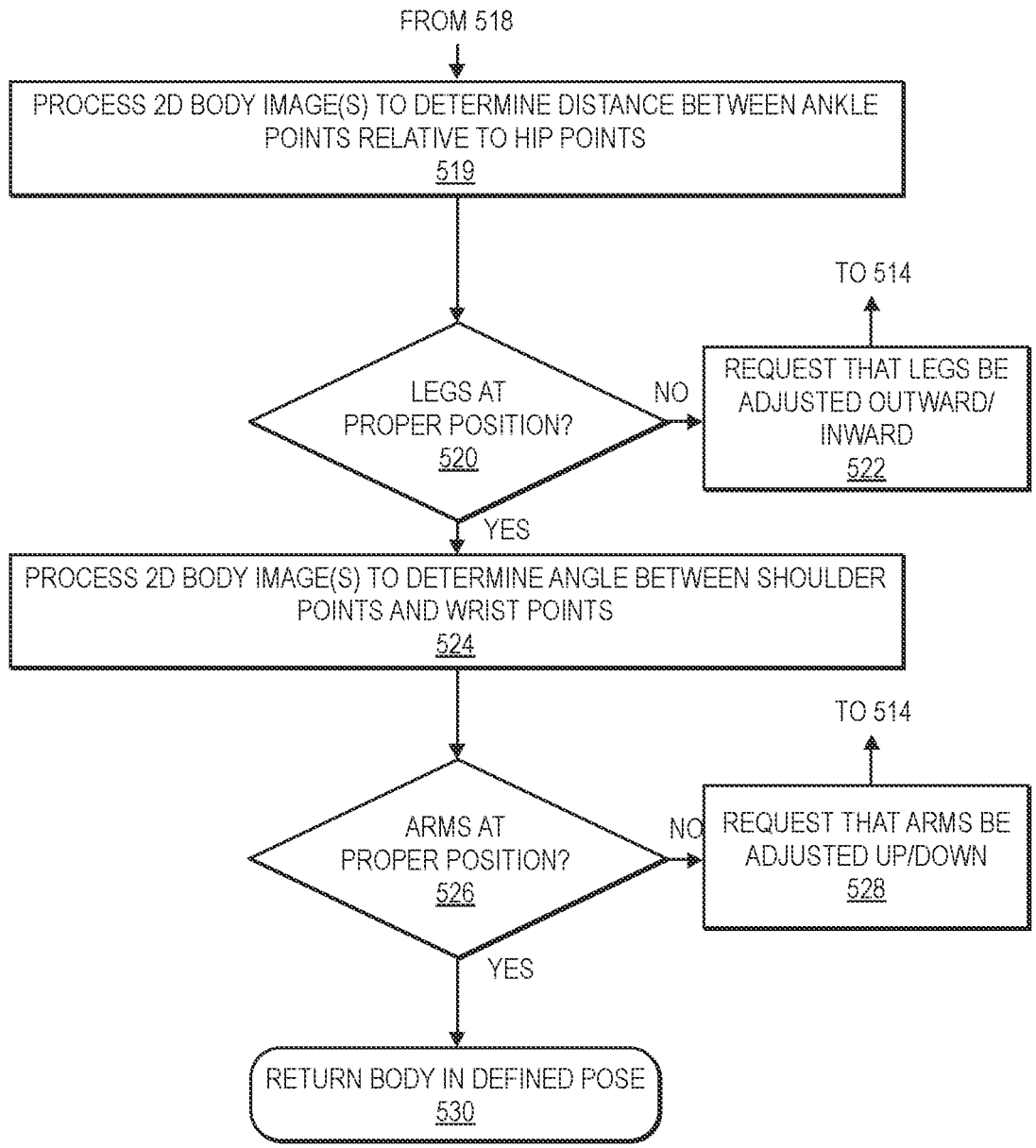

As the request that the user position the body in a defined pose, such as the A Pose, the pose determination process 500 discussed further below with respect to FIG. 5, is performed to confirm that the body is positioned within the field of view of the imaging element and in the defined pose, as in 500. The example process 500 may be performed as illustrated herein at a defined point within the example process 400 to confirm the position and pose of the body before other aspects of the example process 400 are performed. In other implementations, once the example process 500 is initiated, it may continue to monitor the position and pose of the body while the other aspects of the example process 400 are performed. For example, the example process 500, as discussed below, may continue to monitor that the body of the user remains in the field of view and in the defined pose while 2D body images of the body in different body directions are captured, as discussed below. If, during other aspects of the example process 400 it is determined that the body is no longer positioned in the field of view of the imaging element or the body is no longer in the defined pose, the example process 500 may generate a request that the body be positioned in the field of view with the defined pose before other aspects of the example process 400 proceed.

When the example process 500 confirms that the body is within the field of view of the imaging element and in the defined pose, one or more 2D body images of the body in the defined pose are received from the imaging element, as in 410. Those received images are then processed to determine a body direction of the body and to select a 2D body direction image representative of the body in the determined body direction, as in 600. Body direction determination and 2D body direction image selection are discussed below with respect to FIG. 6 and the example process 600.

Upon completion of the example process 600 in which body direction is determined and one or more 2D body direction images are selected and provided to remote computing resources, a determination is made as to whether additional 2D body direction images of the body from other body directions are to be obtained as part of the example process 400, as in 412. In some implementations, only a single 2D body direction image may be obtained and used to generate personalized 3D body parameters and/or body measurements. In other implementations, multiple 2D body direction images of the body in different body directions may be obtained with the example process 400 that are used together to generate personalized 3D body parameters and/or body measurements. For example, in some implementations, four different 2D body direction images (e.g., front side, right side, back side, left side) may be obtained with the example process 400 and used by the remote computing resources to generate personalized 3D body parameters and/or body measurements. In other implementations, more or fewer than four 2D body direction images may be obtained. In some examples, the user of the application executing on the portable device may select how many 2D body direction images are to be obtained and used for personalized 3D body parameter generation.

If it is determined that additional 2D body direction images are to be selected and provided to the remote computing resource for use in generating personalized 3D body parameters and/or body measurements, a request is presented (e.g., visually and/or audibly) that the body be rotated to a next body direction, as in 414. In some implementations, there may be a defined order in which the body is to be rotated. For example, body direction determination may proceed from front side, to right side, to back side, to left side. Such an order of body direction rotation may aid in the accuracy of body direction determination and distinguishing between left side and right side, or front side and back side.

As the request that the body rotate to a next body direction, the example process 400 returns to block 410 and continues. This portion of the process 400 may continue until all 2D body direction images that are to be used for processing by the remote computing resources have been selected and sent to the remote computing resources. If it is determined at decision block 412 that no additional 2D body direction images are to be obtained, the example process 400 completes, as in 416.

FIG. 5 is an example pose determination process 500, in accordance with implementations of the present disclosure. Similar to the example process 400 (FIG. 4), the example process may be performed by an application executing on a portable device, such as application 125 executing on portable device 130, discussed above with respect to FIGS. 1A, 1B, and 2. In other implementations, the example process 500 may be performed by one or more remote computing resources that receives images from the portable device and sends information/messages to the portable device. In still other examples, a portion of the example process 500 may be performed on the portable device and another portion may be performed by the remote computing resources.

As discussed above, the example process 500 may be performed at or near the beginning of the example process 400 to confirm that the body is within the field of view of the imaging element and in the defined pose and then complete. In other implementations, the example process 500 may continually be performed as images are received as part of the example process 400 and 2D body direction images selected.

The example process 500 begins by processing 2D body images received from the imaging element to determine a location of body joints, body features, body parts, etc., generally referred to herein as "body points," in the image, as in 502. For example, each image received from the imaging element may be processed by a neural network, such as a convolutional neural network ("CNN") to determine body point locations, such as the location of body joints (e.g., wrist, ankle, knee), the location of body parts (e.g., hand, foot, shoulder), and/or other body points. As will be appreciated, any trained neural network may be utilized to determine body point locations within a 2D image. In some implementations, because body point determination is performed on the portable device, a low latency neural network, such as ENet may be trained and utilized. In other implementations, other neural networks may be utilized.

The output of the neural network for each image may be a heat map indicating, for each pixel of the image, which is defined by an x, y coordinate (or other coordinate frame), a probability score that a body point is at that position. The probability score may be any defined value or indicator that may be used as in indicator as to the likelihood that a body point has is at the location.

An initial determination may be made as to whether the body is positioned within the field of view of the imaging element by determining if a minimum number of body point locations have been detected with a high enough probability, as in 504. The minimum number may be any defined amount (e.g., one, two, four, etc.). While multiple body points may be located, in some implementations, only particular body points may be considered in determining whether the minimum number of body point locations have been determined. For example, in some implementations, the body point locations for the left shoulder, right shoulder, left ankle, right ankle, left wrist, right wrist, and top of head may be the only body point locations that are considered when determining that the minimum number of body point locations have been determined.

If it is determined that the minimum number of body point locations have not been detected, a request (e.g., visual and/or audible) may be presented that requests that the body be positioned in the field of view, as in 506. If it is determined that a minimum number of body point locations have been determined, a bounding box is formed around the determined body point locations, as in 508, and a determination made as to whether the body is at an appropriate distance from the imaging element/portable device, as in 510. For example, a determination may be made as to whether the bounding box encompasses a defined amount or percentage range (e.g., 60%-70%) of the image, whether a height of the bounding box is within a defined percentage range (e.g., 70%-80%) or amount of the entire height of the image, whether a width of the bound box is within a defined percentage (e.g., 30%-50%) or amount of the entire width of the image, etc.

If it is determined that the bounding box does not encompass a defined amount of the image, a request (visual and/or audible) may be presented requesting that the body be moved forward or backward with respect to the imaging element/portable device, as in 512, and the example process 500 returns to block 508 and continues. For example, if it is determined that the bounding box does not encompass enough of the image, the request may be a request that the body move closer to the imaging element/portable device. In comparison, if the bounding box encompasses too much of the image, or portions of the body point locations are beyond the image, the request may be a request that the body move farther away from the imaging element/portable device.

Once it is determined at decision block 510 that the body is at a correct distance from the imaging element/portable device, 2D body images received from the imaging element are processed to determine body point locations, as in 514. Processing of the 2D body images to determine body point locations may be performed using the same neural network discussed above with respect to block 502 that is executing on the portable device to determine body point locations of the body positioned in the field of view of the imaging element. As discussed above, the output for each 2D body image processed by the neural network may be a heat map that indicates for each pixel of the 2D body image (in x, y coordinates) a probability that a body point is at that location.

The output (heat map) for each 2D body image may then be considered and a determination made as to whether the probability score for each body point location is above a threshold, as in 518. The threshold may be any value (e.g., 0.7) or indicator and may be different for different body points and/or different body point locations. Likewise, in some implementations, the determination may be for all body point locations indicated by the processing of the 2D body images. In other implementations only the locations and probability scores for select body points may be considered when determining if the probability score has been exceeded for those body point locations. For example, in some implementations, the example process may only consider whether the body point locations for the body points of left shoulder, right shoulder, left ankle, right ankle, left wrist, right wrist, left hip, right hip, and top of head exceed the threshold. In other implementations, fewer or additional body point locations may be considered.

If it is determined that the probability score for each body point location is not above the threshold, the example process 500 returns to block 514 and processes the next 2D body image.

Once it is determined that the body point locations do exceed the threshold, the 2D body image is processed to determine a distance between the location of the left ankle point and the right ankle point relative to the distance between the left hip point and the right hip point, as in 519. For example, it may be determined if the distance between the left ankle point and the right ankle point is equal to or greater than the distance between the left hip point and the right hip point.

Based on the relationship between the distance between the left ankle point and the right angle point relative to the distance between the left hip point and the right hip point, a determination is made as to whether the legs are at a proper position, as in 520. For example, if the defined pose is the A Pose, it may be determined that the legs are in the proper position if the distance between the left ankle point and the right ankle point is greater than or equal to the distance between the left hip point and the right hip point. If the distance between the left ankle point and the right ankle point is not greater than or equal to the distance between the left hip point and the right hip point, it may be determined that the legs are not in a proper position.

If it is determined that the legs are not in a proper position, a request is presented (visually and/or audibly) that the legs of the body be adjusted outward or inward, as in 522. For example, if it is determined that the distance between the left ankle point and the right ankle point is less than the distance between the left hip point and the right hip point, a visual, audible, and/or tactile notification may be presented by the portable device requesting that the legs of the body be separated farther apart. As the request is presented, the example process 500 returns to block 514 and continues until it is determined at decision block 520 that the legs are in the proper position for the defined pose.

Once it is determined at decision block 520 that the legs are in the proper position, the 2D body images are processed to determine an angle between the shoulder points and the wrist points, as in 524. For example, an inverse cosine of normalized dot product may be performed to determine arm spacing based on the locations determined for the left shoulder point, the left wrist point, the right shoulder point, and the right wrist point.

Based on the determined angles between the shoulder points and the wrist points, a determination is made as to whether the left arm and right arm are at the proper position, as in 526. Continuing with the above example, if the defined pose is the A Pose, the proper space of the arms may be such that the angle of the arm formed between the should point and wrist point is between 20 degrees and 40 degrees. In other examples, the arm spacing may be different.

If it is determined that the arms are not at a proper position, a visual, audible, and/or tactile notification may be presented by the portable device requesting that the arms be adjusted up or down, as in 528. For example, if it is determined that the angle of the arms exceed the range for the defined pose, the request may be a request that one or both arms be lowered. In comparison, if it is determined that the angle of the arms is below the range for the defined pose, the request may be a request that one or both arms be raised. As the request is presented, the example process 500 returns to block 514 and continues until it is determined at decision block 526 that the arms are in the proper position for the defined pose.

Once it is determined that the arms are in the proper position, the example process 500 returns a notification that the body is in the defined pose (e.g., the A pose), as in 530.

While the above example proceeds in a sequential manner determining that the distance between the body and the imaging element/portable device is correct, the legs are properly positioned, and then the arms are properly positioned, in other implementations, the determination and/or notification for each of the above may be done in parallel or in a different order. Likewise, in some implementations, the requests to make one or more adjustments (e.g., move forward/backward, spread/narrow legs, raise/lower arms) may be presented in any order and/or may all be presented concurrently. In addition, as noted above, the requests may be output by the application executing on the portable device as visual and/or audible outputs. For example, the application may present on a display of the portable device the image of the of the user body as the 2D body images are obtained by the imaging element and overlay a silhouette or other indicator as the proper position for the body according to the defined pose. Specific requests that the user move forward/backward, spread/narrow legs, raise/lower arms may be presented in conjunction with the visual indicators to aid the user in positioning the body in the correct pose.

Figure 6:
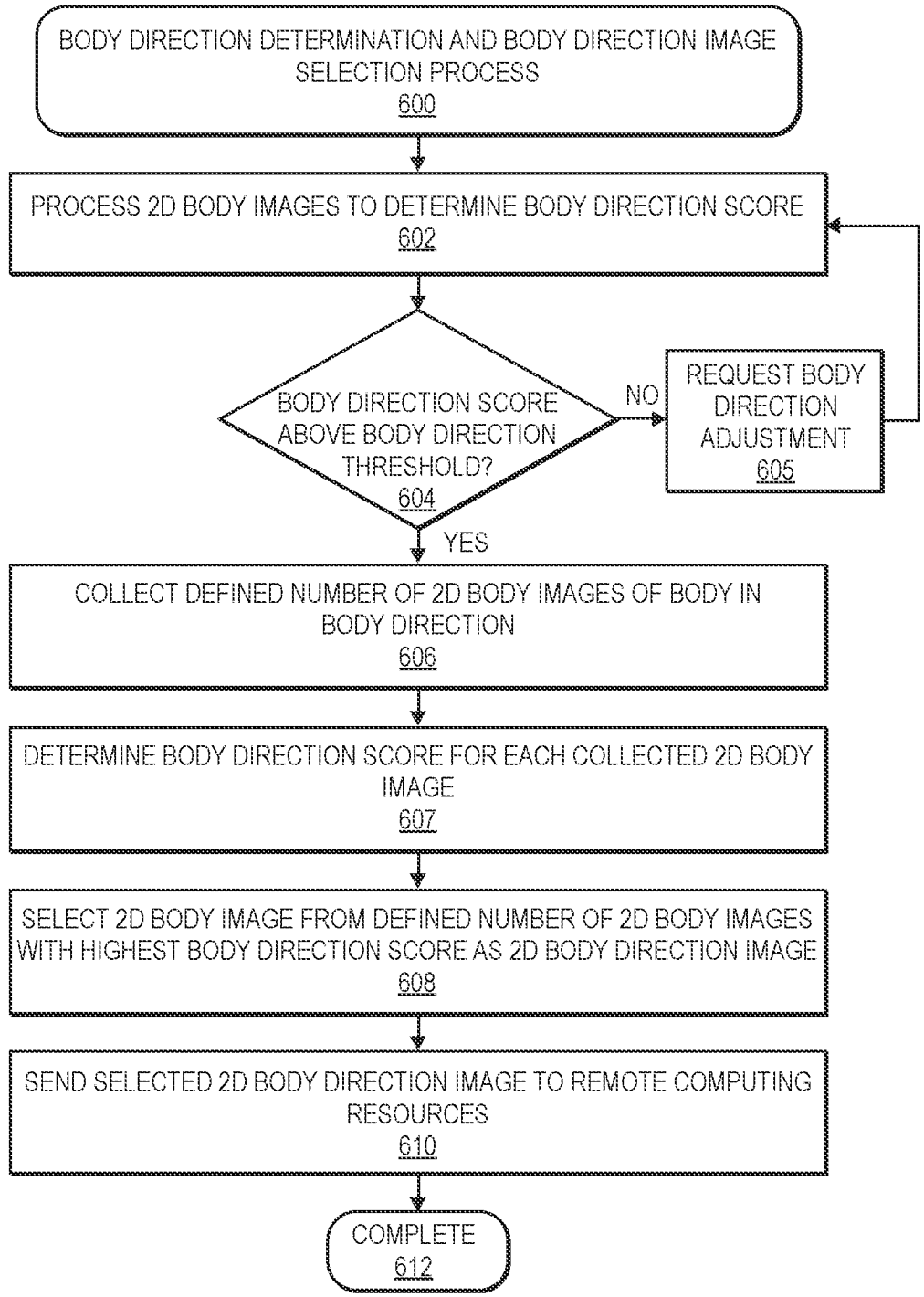
FIG. 6 is an example body direction determination and body direction image selection process, in accordance with implementations of the present disclosure.

FIG. 6 is an example body direction determination and body direction image selection process 600, in accordance with implementations of the present disclosure. Similar to FIGS. 4 and 5, the example process 600 may be performed on a portable device, on remote computing resources, or on a combination of a portable device and remote computing resources.

The example process 600 begins by processing 2D body images received from the imaging element of the portable device to determine a body direction score indicative of a direction of the body represented in the 2D body image with respect to the imaging element/portable device, as in 602. Like the example process 400 (FIG. 4) and 500 (FIG. 5), the example process 600 may be performed by the application executing on the portable device. As such, a low latency image processing technique may be performed to determine the body direction of the body represented in the received 2D body images. For example, a low latency neural network, such as a CNN, may be trained to determine a body direction of a body. In one example a MobileNet CNN may be trained to determine a body direction of a body represented in a received 2D body image. In other implementations, multiple CNNs, one for each potential body direction, may be trained to process input 2D body images and output a score indicating a probability that the body represented in the 2D body image corresponds to the body direction for which the CNN was trained. For example, if the example process 400 (FIG. 4) is to obtain 2D body direction images from a front side, right side, back side, and left side, a different CNN may be trained for each of those four body directions. Received 2D body images may be processed in parallel by each of the four CNNs and a body direction score presented by each CNN indicating a probability that the body represented in the 2D body image is in the body direction trained for that CNN. The CNN with the highest score will indicate the likely body direction of the body represented in the 2D body image.

In some implementations, the order of body directions may be controlled by the application and a request may be presented that the body be initially oriented to the front side, then right side, then back side, then left side (or any other order). In such an example, processing requirements may be further reduced by only processing received 2D body images with the CNN trained for the requested body direction. For example, if the request is that the body be oriented in a right side view with respect to the imaging element, a CNN trained for right side body direction detection may be the only CNN executed to process received 2D body images.

As body direction scores are generated, a determination is made as to whether a body direction score for one of the body directions, or a requested body direction, is above a body direction threshold, as in 604. The body direction threshold may be any value or indicator relative to a confidence that the body direction has been accurately determined. If it is determined that the body direction score does not exceed the body direction threshold, a request is presented (visually and/or audibly) that the body be adjusted to the body direction, as in 605. As the request is presented, the example process 600 returns to block 602 and continues.

Once it is determined at decision block 604 that the body direction score for a received 2D body image exceeds the body direction threshold, a defined number of 2D body images of the body in the 2D body direction are collected, as in 606. The defined number of 2D body images may be any defined number (e.g., one, two, five, twenty, fifty, etc.). In addition, a body direction score is computed for each of the collected 2D body images, as in 607. The body direction scores may be computed using the same neural network utilized and discussed above with respect to block 602. For example, if the body direction is determined to be a front view, a CNN trained for front view body directions may be used to determine body directions scores for each of the collected 2D body images.

A 2D body image of the collected 2D body images having a highest body direction score is then selected as the 2D body direction image for that body direction, as in 608. For example, if twenty 2D body images are collected and body direction scores computed by a CNN trained for front view body directions, the 2D body image with a highest body direction score, as determined by the CNN, is selected as the 2D body direction image for the front view body direction.

Finally, the selected 2D body direction image is sent to remote computing resources for processing to generate personalized 3D body parameters, as in 610, and the example process 600 completes, as in 612. While the illustrated example sends 2D body direction images upon selection, in some implementations, the selected 2D body direction images may remain on the portable device and be sent to the remote computing resources by the example process 400 (FIG. 4) once all 2D body direction images have been selected.

Figure 7:
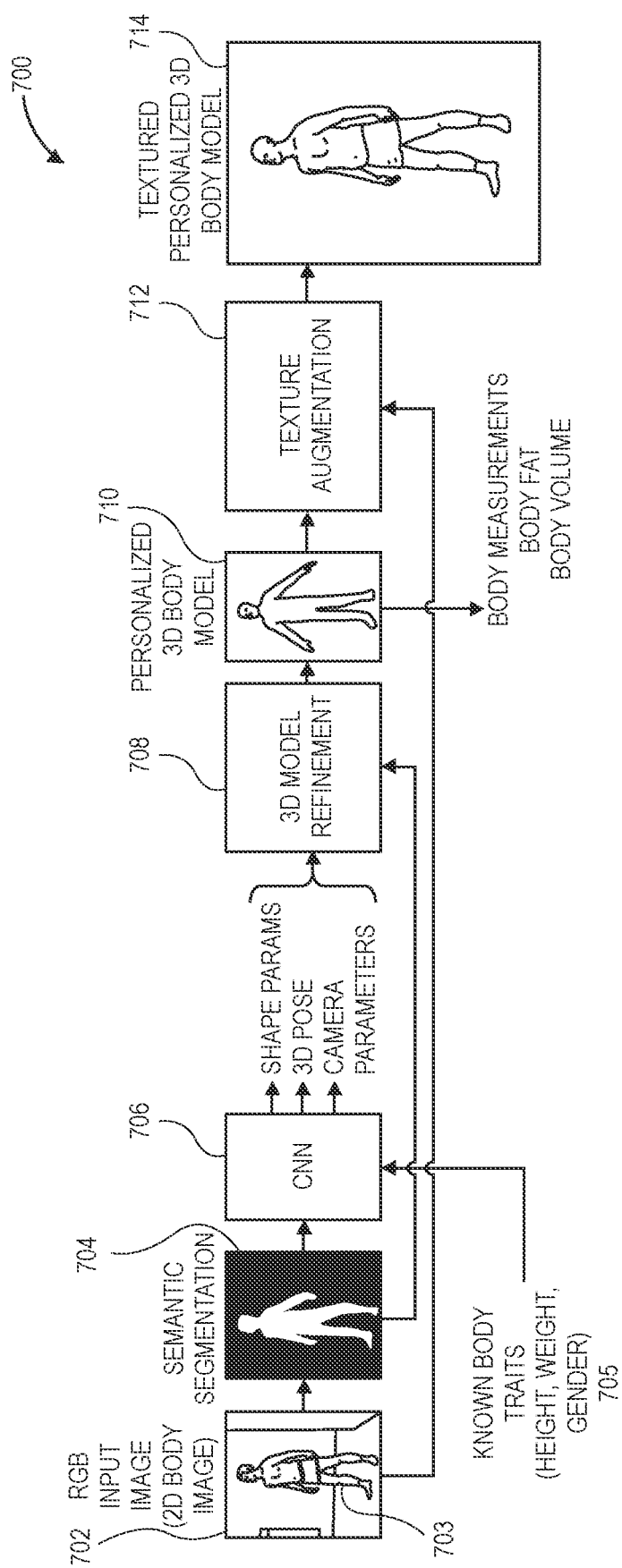
FIG. 7 is a transition diagram of processing two-dimensional body images to produce a personalized three-dimensional model of that body, in accordance with implementations of the present disclosure.

FIG. 7 is a transition diagram 700 of processing 2D body images of a body to produce a personalized 3D body model of that body, in accordance with implementations of the present disclosure.

3D modeling of a body from 2D body images begins with the receipt or creation of a 2D body image 702 that includes a representation of the body 703 of the user to be modeled. As discussed above, 2D body images 702 for use with the disclosed implementations may be generated using any conventional imaging element, such as a standard 2D Red, Green, Blue ("RGB") digital camera that is included on many current portable devices (e.g., tablets, cellular phones, laptops, etc.). The 2D body image may be a still image generated by the imaging element or an image extracted from video generated by the imaging element. Likewise, any number of images may be used with the disclosed implementations.

As discussed, the user may be instructed to stand in a particular orientation (e.g., front facing toward the imaging element, side facing toward the imaging element, back facing toward the imaging element, etc.) and/or to stand in a particular pose, such as the "A" pose as illustrated in image 702. Likewise, the user may be instructed to stand a distance from the camera such that the body of the user is completely included in a field of view of the imaging element and represented in the generated image 702. Still further, in some implementations, the imaging element may be aligned or positioned at a fixed or stationary point and at a fixed or stationary angle so that images generated by the imaging element are each from the same perspective and encompass the same field of view.

As will be appreciated, a user may elect or opt-in to having a personalized 3D body model of the body of the user generated and may also select whether the generated personalized 3D body model and/or other information may be used for further training of the disclosed implementations and/or for other purposes.

The 2D body image 702 that includes a representation of the body 703 of the user may then be processed to produce a silhouette 704 of the body 703 of the user represented in the image 702. A variety of techniques may be used to generate the silhouette 704. For example, background subtraction may be used to subtract or black out pixels of the image that correspond to a background of the image while pixels corresponding to the body 703 of user (i.e., foreground) may be assigned a white or other color values. In another example, a semantic segmentation algorithm may be utilized to label background and body (foreground) pixels. For example, a CNN may be trained with a semantic segmentation algorithm to determine bodies, such as human bodies, in images.

In some implementations, the silhouette of the body of the user may be normalized in height and centered in the image, as discussed further below. This may be done to further simplify and standardize inputs to a CNN to those on which the CNN was trained. Likewise, a silhouette of the body of the user may be preferred over the representation of the body of the user so that the CNN can focus only on body shape and not skin tone, texture, clothing, etc.

The silhouette 704 of the body may then be processed by one or more other CNNs 706 that are trained to determine body traits, also referred to herein as body features, representative of the body and to produce personalized 3D body parameters that are used to generate a personalized 3D body model of the body. In some implementations, the CNN 706 may be trained for multi-mode input to receive as inputs to the CNN the silhouette 704, and one or more known body attributes 705 of the body of the user. For example, a user may provide a height of the body of the user, a weight of the body of the user, a gender of the body of the user, etc., and the CNN may receive one or more of those provided attributes as an input.

Based on the received inputs, the CNN 706 generates personalized 3D body parameters, such as 3D joint locations, body volume, shape of the body, pose angles, etc. In some implementations, the CNN 706 may be trained to predict hundreds of body parameters of the body represented in the image 702.

Utilizing the personalized 3D body parameters, a personalized 3D body model of the body is generated. For example, the personalized 3D body parameters may be provided to a body model, such as the Shape Completion and Animation of People ("SCAPE") body model, a Skinned Multi-Person Linear ("SMPL") body model, etc., and the body model may generate the personalized 3D body model of the body of the user based on those predicted body parameters.

In some implementations, as discussed further below, personalized 3D model refinement 708 may be performed to refine or revise the generated personalized 3D body model to better represent the body of the user. For example, the personalized 3D body model may be compared to the representation of the body 703 of the user in the image 702 to determine differences between the shape of the body 703 of the user represented in the image 702 and the shape of the personalized 3D body model. Based on the determined differences, the silhouette 704 may be revised and the revised silhouette processed by the CNN 706 to produce a revised personalized 3D body model of the body of the user. This refinement may continue until there is no or little difference between the shape of the body 703 of the user represented in the image 702 and the shape of the personalized 3D body model 710. In other implementations, a 2D model image may be generated from the personalized 3D body model and that 2D model image may be compared to the silhouette and/or the 2D body image to determine differences between the 2D model image and the 2D body image or silhouette. Based on the determined differences, the personalized 3D body parameters and/or the personalized 3D body model may be revised until the personalized 3D body model corresponds to the body of the user represented in the 2D body image and/or the silhouette.

Still further, in some implementations, the personalized 3D body model 710 of the body of the user may be augmented with one or more textures, texture augmentation 712, determined from the image 702 of the body of the user. For example, the personalized 3D body model may be augmented to have a same or similar color to a skin color of the body 703 represented in the image 702, clothing or clothing colors represented in the image 702 may be used to augment the personalized 3D body model, facial features, hair, hair color, etc., of the body of the user represented in the image 702 may be determined and used to augment the personalized 3D body model, etc.

The result of the processing illustrated in the transition 700 is a personalized 3D body model 714 or avatar representative of the body of the user, that has been generated from 2D body images of the body of the user.

Figure 8A:
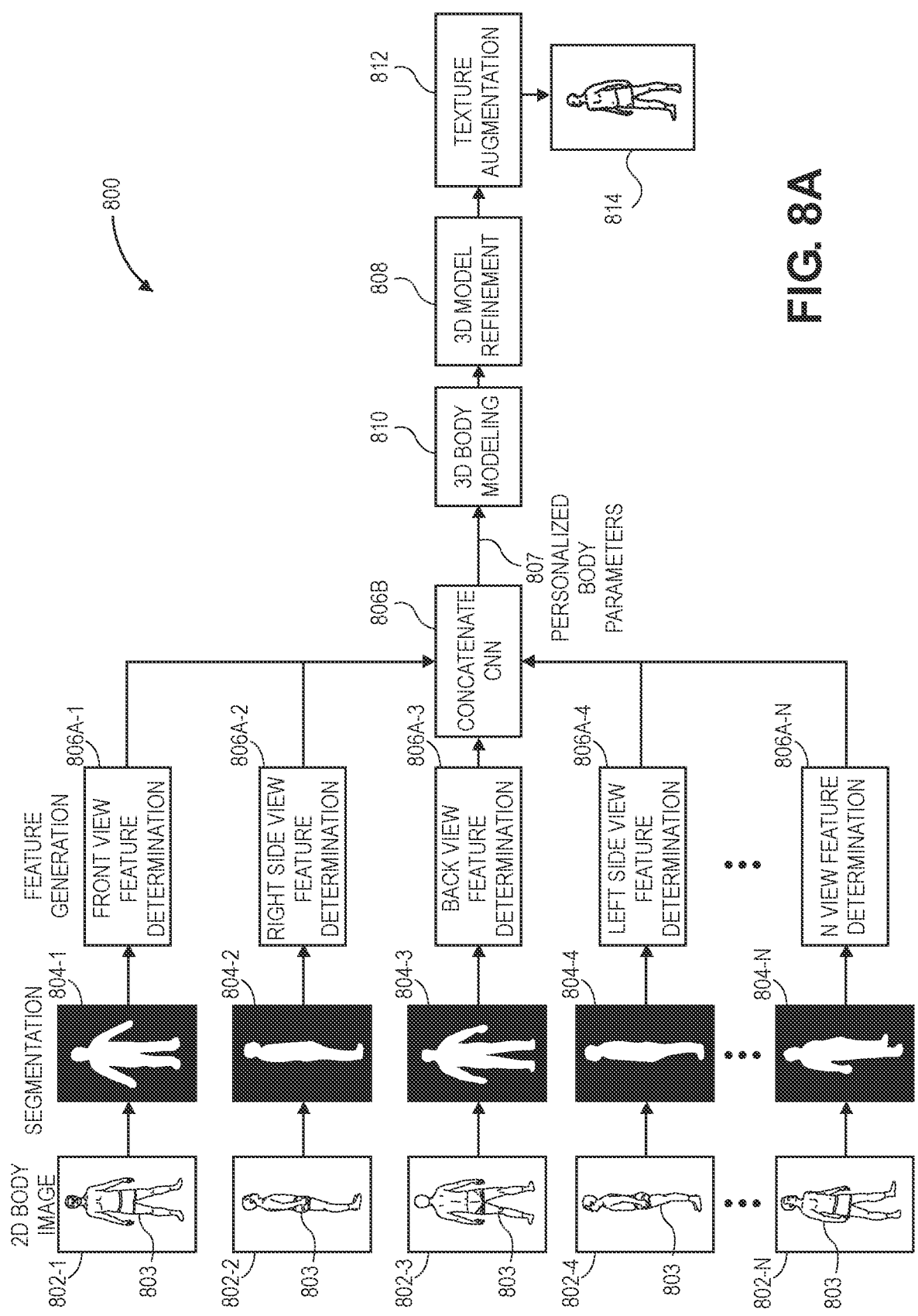
FIG. 8A is another transition diagram of processing two-dimensional body images to produce a personalized three-dimensional model of that body, in accordance with implementations of the present disclosure.

FIG. 8A is another transition diagram 800 of processing 2D body images 802 of a body to produce a personalized 3D body model of that body, in accordance with implementations of the present disclosure.

In some implementations, multiple 2D body images of a body from different views (e.g., front view, side view, back view, three-quarter view, etc.), such as 2D body images 802-1, 802-2, 802-3, 802-4 through 802-N may be utilized with the disclosed implementations to generate a personalized 3D body model of the body. In the illustrated example, the first 2D body image 802-1 is an image of a human body 803 oriented in a front view facing a 2D imaging element. The second 2D body image 802-2 is an image of the human body 803 oriented in a first side view facing the 2D imaging element. The third 2D body image 802-3 is an image of the human body 803 oriented in a back view facing the 2D imaging element. The fourth 2D body image 802-4 is an image of the human body 803 oriented in a second side view facing the 2D imaging element. As will be appreciated, any number of 2D body images 802-1 through 802-N may be generated with the view of the human body 803 in any number or orientations with respect to the 2D imaging element.

Each of the 2D body images 802-1 through 802-N are processed to segment pixels of the image that represent the human body from pixels of the image that do not represent the human body to produce a silhouette 804 of the human body as represented in that image. Segmentation may be done through, for example, background subtraction, semantic segmentation, etc. In one example, a baseline image of the background may be known and used to subtract out pixels of the image that correspond to pixels of the baseline image, thereby leaving only foreground pixels that represent the human body. The background pixels may be assigned RGB color values for black (i.e., 0,0,0). The remaining pixels may be assigned RGB values for white (i.e., 255, 255, 255) to produce the silhouette 804 or binary segmentation of the human body.

In another example, a CNN utilizing a semantic segmentation algorithm may be trained using images of human bodies, or simulated human bodies to train the CNN to distinguish between pixels that represent human bodies and pixels that do not represent human bodies. In such an example, the CNN may process the image 802 an indicate or label pixels that represent the body (foreground) and pixels that do not represent the body (background). The background pixels may be assigned RGB color values for black (i.e., 0,0,0). The remaining pixels may be assigned RGB values for white (i.e., 255, 255, 255) to produce the silhouette or binary segmentation of the human body.

In other implementations, other forms or algorithms, such as edge detection, shape detection, etc., may be used to determine pixels of the image 802 that represent the body and pixels of the image 802 that do not represent the body and a silhouette 804 of the body produced therefrom.

Returning to FIG. 8A, the first 2D body image 802-1 is processed to segment a plurality of pixels of the first 2D body image 802-1 that represent the human body from a plurality of pixels of the first 2D body image 802-1 that do not represent the human body, to produce a front silhouette 804-1 of the human body. The second 2D body image 802-2 is processed to segment a plurality of pixels of the second 2D body image 802-2 that represent the human body from a plurality of pixels of the second 2D body image 802-2 that do not represent the human body, to produce a first side silhouette 804-2 of the human body. The third 2D body image 802-3 is processed to segment a plurality of pixels of the third 2D body image 802-3 that represent the human body from a plurality of pixels of the third 2D body image 802-3 that do not represent the human body, to produce a back silhouette 804-3 of the human body. The fourth 2D body image 802-4 is processed to segment a plurality of pixels of the fourth 2D body image 802-4 that represent the human body from a plurality of pixels of the fourth 2D body image 802-4 that do not represent the human body, to produce a second side silhouette 804-4 of the human body. Processing of the 2D body images 802-1 through 802-N to produce silhouettes 804-1 through 804-N from different orientations of the human body 803 may be performed for any number of images 802.

In some implementations, in addition to generating a silhouette 804 from the 2D body image, the silhouette may be normalized in size and centered in the image. For example, the silhouette may be cropped by computing a bounding rectangle around the silhouette 804. The silhouette 804 may then be resized according to s, which is a function of a known height h of the user represented in the 2D body image (e.g., the height may be provided by the user):

$$s = h * \frac{0.8 * image_h}{\mu_h} \quad (1)$$

Where $image_h$ is the input image height, which may be based on the pixels of the image, and $\mu_h$ is the average height of a person (e.g., ~160 centimeters for females; ~176 centimeters for males).

Each silhouette 804 representative of the body may then be processed to determine body traits or features of the human body. For example, different CNNs may be trained using silhouettes of bodies, such as human bodies, from different orientations with known features. In some implementations, different CNNs may be trained for different orientations. For example, a first CNN 806A-1 may be trained to determine front view features from front view silhouettes 804-1. A second CNN 806A-2 may be trained to determine right side features from right side silhouettes. A third CNN 806A-3 may be trained to determine back view features from back view silhouettes. A fourth CNN 806A-4 may be trained to determine left side features from left side silhouettes. Different CNNs 806A-1 through 806A-N may be trained for each of the different orientations of silhouettes 804-1 through 804-N. Alternatively, one CNN may be trained to determine features from any orientation silhouette.

In implementations that utilize multiple images of the body 803 to produce multiple sets of features, such as the example illustrated in FIG. 8A, those features may be concatenated 806B and the concatenated features processed together with a CNN to generate a set of body parameters 807. For example, a CNN may be trained to receive features generated from different silhouettes 804 to produce body parameters 807. The body parameters 807 may indicate any aspect or information related to the body 803 represented in the images 802. For example, the body parameters 807 may indicate 3D joint locations, body volume, shape of the body, pose angles, etc. In some implementations, the CNN 806B may be trained to predict hundreds of body parameters 807 corresponding to the body 803 represented in the images 802.

Utilizing the body parameters 807, personalized 3D body modeling 810 of the body 803 represented in the 2D body images 802 is performed to generate a personalized 3D body model of the body 803 represented in the 2D body images 802. For example, the body parameters 807 may be provided to a body model, such as the SCAPE body model, the SMPL body model, etc., and the body model may generate the personalized 3D body model of the body 803 represented in the images 802 based on those body parameters 807.

In the illustrated example, personalized 3D model refinement 808 may be performed to refine or revise the generated personalized 3D body model to better represent the body 803 represented in the 2D body images 802. For example, the personalized 3D body model may be compared to the body 803 represented in one or more of the 2D body images to determine differences between the shape of the body 803 represented in the 2D body image 802 and the shape of the personalized 3D body model generated from the body parameters. In some implementations, the personalized 3D body model may be compared to a single image, such as image 802-1. In other implementations, the personalized 3D body model may be compared to each of the 2D body images 802-1 through 802-N in parallel or sequentially. In still other implementations, one or more 2D model images may be generated from the personalized 3D body model and those 2D model images may be compared to the silhouettes and/or the 2D body images to determine differences between the 2D model images and the silhouette/2D body images.

Comparing the personalized 3D body model and/or a 2D model image with a 2D body image 802 or silhouette 854 may include determining an approximate pose of the body 803 represented in the 2D body image and adjusting the personalized 3D body model to the approximate pose. The personalized 3D body model or rendered 2D model image may then be overlaid or otherwise compared to the body 803 represented in the 2D body image 802 and/or represented in the silhouette 804 to determine a difference between the personalized 3D body model and the 2D body image.

Based on the determined differences between the personalized 3D body model and the body 803 represented in the 2D body image 802, the silhouette 804 generated from that image may be revised to account for those differences. For example, if the personalized 3D body model is compared with the body 803 represented in the first image 802-1 and differences are determined, the silhouette 804-1 may be revised based on those differences. Alternatively, the body parameters and/or the personalized 3D body model may be revised to account for those differences.

If a silhouette is revised as part of the personalized 3D model refinement 808, the revised silhouette may be processed to determine revised features for the body 803 represented in the 2D body image based on the revised silhouette. The revised features may then be concatenated with the features generated from the other silhouettes or with revised features generated from other revised silhouettes that were produced by the personalized 3D model refinement 808. For example, the personalized 3D model refinement 808 may compare the generated personalized 3D body model with the body 803 as represented in two or more 2D body images 802, such as a front image 802-1 and a back image 802-3, differences determined for each of those images, revised silhouettes generated from those differences and revised front view features and revised back view features generated. Those revised features may then be concatenated with the two side view features to produce revised body model parameters. In other implementations, personalized 3D model refinement 808 may compare the personalized 3D body model with all views of the body 803 represented in the 2D body images 802 to determine differences and generate revised silhouettes for each of those 2D body images 802-1 through 802-N. Those revised silhouettes may then be processed by the CNNs 806A-1 through 806A-N to produce revised features and those revised features concatenated to produce revised body parameters 807. Finally, the revised body parameters may be processed by personalized 3D modeling 810 to generate a revised personalized 3D body model. This process of personalized 3D refinement may continue until there is no or limited difference (e.g., below a threshold difference) between the generated personalized 3D body model and the body 803 represented in the 2D body images 802.

In another implementation, personalized 3D model refinement 808 may sequentially compare the personalized 3D body model with representations of the body 803 in the different 2D body images 802. For example, personalized 3D model refinement 808 may compare the personalized 3D body model with a first representation of the body 803 in a first 2D body image 802-1 to determine differences that are then used to generate a revised silhouette 804-1 corresponding to that first 2D body image 802-1. The revised silhouette may then be processed to produce revised features and those revised features may be concatenated 806B with the features generated from the other silhouettes 804-2 through 804-N to generate revised body parameters, which may be used to generate a revised personalized 3D body model. The revised personalized 3D body model may then be compared with a next image of the plurality of 2D body images 802 to determine any differences and the process repeated. This process of personalized 3D refinement may continue until there is no or limited difference (e.g., below a threshold difference) between the generated personalized 3D body model and the body 803 represented in the 2D body images 802.

In some implementations, upon completion of personalized 3D model refinement 808, the personalized 3D body model of the body represented in the 2D body images 802 may be augmented with one or more textures, texture augmentation 812, determined from one or more of the 2D body images 802-1 through 802-N. For example, the personalized 3D body model may be augmented to have a same or similar color to a skin color of the body 803 represented the 2D body images 802, clothing or clothing colors represented in the 2D body images 802 may be used to augment the personalized 3D body model, facial features, hair, hair color, etc., of the body 803 represented in the 2D body image 802 may be determined and used to augment the personalized 3D body model.

Similar to personalized 3D model refinement, the approximate pose of the body in one of the 2D body images 802 may be determined and the personalized 3D body model adjusted accordingly so that the texture obtained from that 2D body image 802 may be aligned and used to augment that portion of the personalized 3D body model. In some implementations, alignment of the personalized 3D body model with the approximate pose of the body 803 may be performed for each 2D body image 802-1 through 802-N so that texture information or data from the different views of the body 803 represented in the different 2D body images 802 may be used to augment the different poses of the resulting personalized 3D body model.

The result of the processing illustrated in the transition 800 is a personalized 3D body model 814 or avatar representative of the body of the user, that has been generated from 2D body images 802 of the body 803 of the user.

Figure 8B:
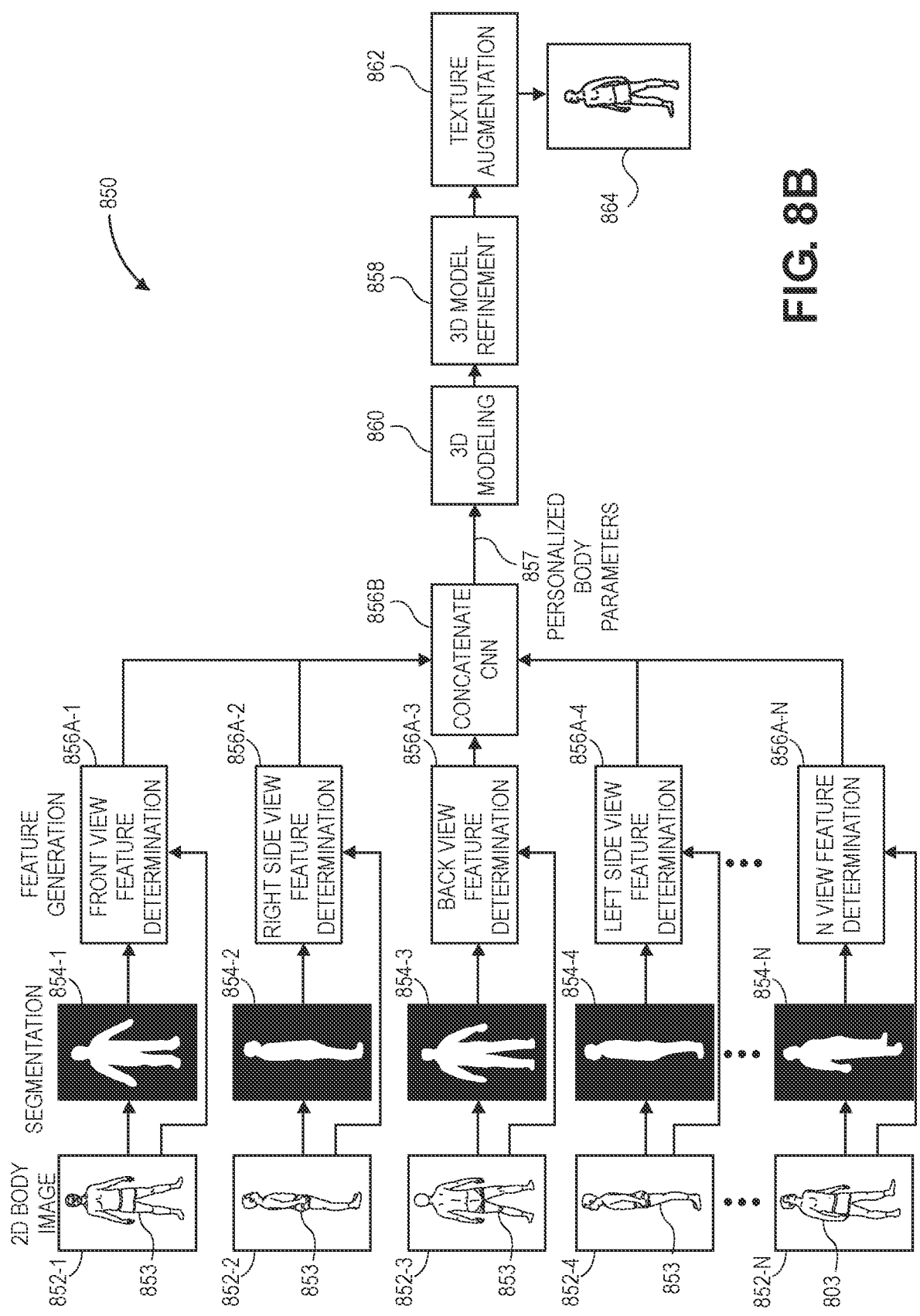
FIG. 8B is another transition diagram of processing two-dimensional body images to produce a personalized three-dimensional model of that body, in accordance with implementations of the present disclosure.

FIG. 8B is another transition diagram 850 of processing 2D body images 852 of a body to produce a personalized three-dimensional model of that body, in accordance with implementations of the present disclosure.

In some implementations, multiple 2D body images of a body from different views (e.g., front view, side view, back view, three-quarter view, etc.), such as 2D body images 852-1, 852-2, 852-3, 852-4 through 852-N may be utilized with the disclosed implementations to generate a personalized 3D body model of the body. In the illustrated example, the first 2D body image 852-1 is an image of a human body 853 oriented in a front view facing a 2D imaging element. The second 2D body image 852-2 is an image of the human body 853 oriented in a first side view facing the 2D imaging element. The third 2D body image 852-3 is an image of the human body 853 oriented in a back view facing the 2D imaging element. The fourth 2D body image 852-4 is an image of the human body 853 oriented in a second side view facing the 2D imaging element. As will be appreciated, any number of 2D body images 852-1 through 852-N may be generated with the view of the human body 853 in any number or orientations with respect to the 2D imaging element.

Each of the 2D body images 852-1 through 852-N are processed to segment pixels of the image that represent the human body from pixels of the image that do not represent the human body to produce a silhouette 854 of the human body as represented in that image. Segmentation may be done through, for example, background subtraction, semantic segmentation, etc. In one example, a baseline image of the background may be known and used to subtract out pixels of the image that correspond to pixels of the baseline image, thereby leaving only foreground pixels that represent the human body. The background pixels may be assigned RGB color values for black (i.e., 0,0,0). The remaining pixels may be assigned RGB values for white (i.e., 255, 255, 255) to produce the silhouette 854 or binary segmentation of the human body.

In another example, a CNN utilizing a semantic segmentation algorithm may be trained using images of human bodies, or simulated human bodies to train the CNN to distinguish between pixels that represent human bodies and pixels that do not represent human bodies. In such an example, the CNN may process the image 852 an indicate or label pixels that represent the body (foreground) and pixels that do not represent the body (background). The background pixels may be assigned RGB color values for black (i.e., 0,0,0). The remaining pixels may be assigned RGB values for white (i.e., 255, 255, 255) to produce the silhouette or binary segmentation of the human body.

In other implementations, other forms or algorithms, such as edge detection, shape detection, etc., may be used to determine pixels of the image 852 that represent the body and pixels of the image 852 that do not represent the body and a silhouette 854 of the body produced therefrom.

Returning to FIG. 8B, the first 2D body image 852-1 is processed to segment a plurality of pixels of the first 2D body image 852-1 that represent the human body from a plurality of pixels of the first 2D body image 852-1 that do not represent the human body, to produce a front silhouette 854-1 of the human body. The second 2D body image 852-2 is processed to segment a plurality of pixels of the second 2D body image 852-2 that represent the human body from a plurality of pixels of the second 2D body image 852-2 that do not represent the human body, to produce a first side silhouette 854-2 of the human body. The third 2D body image 852-3 is processed to segment a plurality of pixels of the third 2D body image 852-3 that represent the human body from a plurality of pixels of the third 2D body image 852-3 that do not represent the human body, to produce a back silhouette 854-3 of the human body. The fourth 2D body image 852-4 is processed to segment a plurality of pixels of the fourth 2D body image 852-4 that represent the human body from a plurality of pixels of the fourth 2D body image 852-4 that do not represent the human body, to produce a second side silhouette 854-4 of the human body. Processing of the 2D body images 852-1 through 852-N to produce silhouettes 854-1 through 854-N from different orientations of the human body 853 may be performed for any number of images 852.

Similar to FIG. 8A, in some implementations, in addition to generating a silhouette 854 from the 2D body image, the silhouette may be normalized in size and centered in the image. For example, the silhouette may be cropped by computing a bounding rectangle around the silhouette 854. The silhouette 854 may then be resized according to s, which is a function of a known height h of the user represented in the 2D body image (e.g., the height may be provided by the user):

$$s = h * \frac{0.8 * image_h}{\mu_h} \quad (1)$$

Where $image_h$ is the input image height, which may be based on the pixels of the image, and $\mu_h$ is the average height of a person (e.g., ~160 centimeters for females; ~176 centimeters for males). In some implementations, the body 853 represented in the 2D body image may be similarly resized to correspond to the resized dimensions of the resized silhouette.

Each silhouette 854 representative of the body may then be processed to determine body traits or features of the human body. For example, different CNNs may be trained using silhouettes of bodies, such as human bodies, from different orientations with known features. In some implementations, different CNNs may be trained for different orientations. For example, a first CNN 856A-1 may be trained to determine front view features from front view silhouettes 854-1. A second CNN 856A-2 may be trained to determine right side features from right side silhouettes. A third CNN 856A-3 may be trained to determine back view features from back view silhouettes. A fourth CNN 856A-4 may be trained to determine left side features from left side silhouettes. Different CNNs 856A-1 through 856A-N may be trained for each of the different orientations of silhouettes 854-1 through 854-N. Alternatively, one CNN may be trained to determine features from any orientation silhouette.

In some implementations, the same or different CNNs may also utilize the 2D body image 802 as an input to the CNN that is used to generate and determine the body features. For example, the first CNN 856A-1 may be trained to determine front view features based on inputs of the front view silhouettes 854-1 and/or the 2D body image 852-1. The second CNN 856A-2 may be trained to determine right side features from right side silhouettes and/or the right side 2D body image 852-2. The third CNN 856A-3 may be trained to determine back view features from back view silhouettes and/or the back view 2D body image 852-3. The fourth CNN 856A-4 may be trained to determine left side features from left side silhouettes and/or the left side 2D body image 852-4. Different CNNs 856A-1 through 856A-N may be trained for each of the different orientations of silhouettes 854-1 through 854-N and/or 2D body images 802-1 through 802-N.

In still other implementations, different CNNS may be trained for each of the silhouettes 854 and the 2D body images. For example, the first CNN 856A-1 may be trained to determine front view features from the silhouette 854-1 and another front view CNN may be trained to determine front view features from the 2D body image 852-1. The second CNN 856A-2 may be trained to determine right side view features from the silhouette 854-2 and another right side view CNN may be trained to determine right side view features from the 2D body image 852-2. The third CNN 856A-3 may be trained to determine back view features from the silhouette 854-3 and another back view CNN may be trained to determine back view features from the 2D body image 852-3. The fourth CNN 856A-4 may be trained to determine left side view features from the silhouette 854-4 and another left side view CNN may be trained to determine left side view features from the 2D body image 852-4.

In implementations that utilize multiple images of the body 853 and/or multiple silhouettes to produce multiple sets of features, such as the example illustrated in FIG. 8B, those features may be concatenated 856B and the concatenated features processed together with a CNN to generate a set of body parameters 857. For example, a CNN may be trained to receive features generated from different silhouettes 854, features generated from different 2D body images 852, and/or features generated by a CNN that processes both silhouettes 854 and the 2D body images 852 to produce body parameters 857. The body parameters 857 may indicate any aspect or information related to the body 853 represented in the images 852. For example, the body parameters 857 may indicate 3D joint locations, body volume, shape of the body, pose angles, etc. In some implementations, the CNN 856B may be trained to predict hundreds of body parameters 857 corresponding to the body 853 represented in the images 852.

Utilizing the body parameters 857, personalized 3D modeling 860 of the body 853 represented in the 2D body images 852 is performed to generate a personalized 3D body model of the body 853 represented in the 2D body images 852. For example, the body parameters 857 may be provided to a body model, such as the SCAPE body model, the SMPL body model, etc., and the body model may generate the personalized 3D body model of the body 853 represented in the images 852 based on those body parameters 857.

In the illustrated example, personalized 3D model refinement 858 may be performed to refine or revise the generated personalized 3D body model to better represent the body 853 represented in the 2D body images 852. For example, as discussed above, the personalized 3D body model may be compared to the body 853 represented in one or more of the 2D body images to determine differences between the shape of the body 853 represented in the 2D body image 852 and the shape of the personalized 3D body model generated from the body parameters. In some implementations, the personalized 3D body model may be compared to a single image, such as image 852-1. In other implementations, the personalized 3D body model may be compared to each of the 2D body images 852-1 through 852-N in parallel or sequentially. In still other implementations, one or more 2D model images may be generated from the personalized 3D body model and those 2D model images may be compared to the silhouettes and/or the 2D body images to determine differences between the 2D model images and the silhouette/2D body images.

Comparing the personalized 3D body model and/or a 2D model image with a 2D body image 852 or silhouette 854 may include determining an approximate pose of the body 853 represented in the 2D body image and adjusting the personalized 3D body model to the approximate pose. The personalized 3D body model or rendered 2D model image may then be overlaid or otherwise compared to the body 853 represented in the 2D body image 852 and/or represented in the silhouette 854 to determine a difference between the personalized 3D body model image and the 2D body image/silhouette.

Based on the determined differences between the personalized 3D body model and the body 853 represented in the 2D body image 852, the silhouette 854 generated from that image may be revised to account for those differences. Alternatively, the body parameters and/or the personalized 3D body model may be revised to account for those differences.

In some implementations, upon completion of personalized 3D model refinement 858, the personalized 3D body model of the body represented in the 2D body images 852 may be augmented with one or more textures, texture augmentation 862, determined from one or more of the 2D body images 852-1 through 852-N. For example, the personalized 3D body model may be augmented to have a same or similar color to a skin color of the body 853 represented the 2D body images 852, clothing or clothing colors represented in the 2D body images 852 may be used to augment the personalized 3D body model, facial features, hair, hair color, etc., of the body 853 represented in the 2D body image 852 may be determined and used to augment the personalized 3D body model.

Similar to personalized 3D model refinement, the approximate pose of the body in one of the 2D body images 852 may be determined and the personalized 3D body model adjusted accordingly so that the texture obtained from that 2D body image 852 may be aligned and used to augment that portion of the personalized 3D body model. In some implementations, alignment of the personalized 3D body model with the approximate pose of the body 853 may be performed for each 2D body image 852-1 through 852-N so that texture information or data from the different views of the body 853 represented in the different 2D body images 852 may be used to augment the different poses of the resulting personalized 3D body model.

The result of the processing illustrated in the transition 850 is a personalized 3D body model 864 or avatar representative of the body of the user, that has been generated from 2D body images 852 of the body 853 of the user.

As discussed above, features or objects expressed in imaging data, such as human bodies, colors, textures or outlines of the features or objects, may be extracted from the data in any number of ways. For example, colors of pixels, or of groups of pixels, in a digital image may be determined and quantified according to one or more standards, e.g., the RGB ("red-green-blue") color model, in which the portions of red, green or blue in a pixel are expressed in three corresponding numbers ranging from 0 to 255 in value, or a hexadecimal model, in which a color of a pixel is expressed in a six-character code, wherein each of the characters may have a range of sixteen. Moreover, textures or features of objects expressed in a digital image may be identified using one or more computer-based methods, such as by identifying changes in intensities within regions or sectors of the image, or by defining areas of an image corresponding to specific surfaces.

Furthermore, edges, contours, outlines, colors, textures, silhouettes, shapes or other characteristics of objects, or portions of objects, expressed in images may be identified using one or more algorithms or machine-learning tools. The objects or portions of objects may be identified at single, finite periods of time, or over one or more periods or durations. Such algorithms or tools may be directed to recognizing and marking transitions (e.g., the edges, contours, outlines, colors, textures, silhouettes, shapes or other characteristics of objects or portions thereof) within the digital images as closely as possible, and in a manner that minimizes noise and disruptions, and does not create false transitions. Some detection algorithms or techniques that may be utilized in order to recognize characteristics of objects or portions thereof in digital images in accordance with the present disclosure include, but are not limited to, Canny edge detectors or algorithms; Sobel operators, algorithms or filters; Kayyali operators; Roberts edge detection algorithms; Prewitt operators; Frei-Chen methods; semantic segmentation algorithms; background subtraction; or any other algorithms or techniques that may be known to those of ordinary skill in the pertinent arts.

Image processing algorithms, other machine learning algorithms or CNNs may be operated on computer devices of various sizes or types, including but not limited to smartphones or other cell phones, tablets, video cameras or other computer-based machines. Such mobile devices may have limited available computer resources, e.g., network bandwidth, storage capacity or processing power, as compared to larger or more complex computer devices. Therefore, executing computer vision algorithms, other machine learning algorithms, or CNNs on such devices may occupy all or much of the available resources, without any guarantee, or even a reasonable assurance, that the execution of such algorithms will be successful. For example, processing digital 2D body images captured by a user of a portable device (e.g., smartphone, tablet, laptop, webcam) according to one or more algorithms in order to produce a personalized 3D body model from the digital images may be an ineffective use of the limited resources that are available on the smartphone or tablet. Accordingly, in some implementations, as discussed herein, some or all of the processing may be performed by one or more computing resources that are remote from the portable device. In some implementations, initial processing of the images to generate binary segmented silhouettes may be performed on the device. Subsequent processing to generate and refine the personalized 3D body model may be performed on one or more remote computing resources. For example, the silhouettes may be sent from the portable device to the remote computing resources for further processing. Still further, in some implementations, texture augmentation of the personalized 3D body model of the body may be performed on the portable device or remotely.

In some implementations, to increase privacy of the user, only the binary segmented silhouette may be sent from the device for processing on the remote computing resources and the original 2D images that include the representation of the user may be maintained locally on the portable device. In such an example, the rendered personalized 3D body model may be sent back to the device and the device may perform texture augmentation of the received personalized 3D body model based on those images. Utilizing such a distributed computing arrangement retains user identifiable information on the portable device of the user while at the same time leveraging the increased computing capacity available at remote computing resources.

Machine learning tools, such as artificial neural networks, have been utilized to identify relations between respective elements of apparently unrelated sets of data. An artificial neural network, such as CNN, is a parallel distributed computing processor comprised of individual units that may collectively learn and store experimental knowledge, and make such knowledge available for use in one or more applications. Such a network may simulate the non-linear mental performance of the many neurons of the human brain in multiple layers by acquiring knowledge from an environment through one or more flexible learning processes, determining the strengths of the respective connections between such neurons, and utilizing such strengths when storing acquired knowledge. Like the human brain, an artificial neural network may use any number of neurons in any number of layers, including an input layer, an output layer, and one or more intervening hidden layers. In view of their versatility, and their inherent mimicking of the human brain, machine learning tools including not only artificial neural networks but also nearest neighbor methods or analyses, factorization methods or techniques, K-means clustering analyses or techniques, similarity measures such as log likelihood similarities or cosine similarities, latent Dirichlet allocations or other topic models, or latent semantic analyses have been utilized in image processing applications.

Artificial neural networks may be trained to map inputted data to desired outputs by adjusting the strengths of the connections between one or more neurons, which are sometimes called synaptic weights. An artificial neural network may have any number of layers, including an input layer, an output layer, and any number of intervening hidden layers. Each of the neurons in a layer within a neural network may receive one or more inputs and generate one or more outputs in accordance with an activation or energy function, with parameters corresponding to the various strengths or synaptic weights. Likewise, each of the neurons within a network may be understood to have different activation or energy functions; in this regard, such a network may be dubbed a heterogeneous neural network. In some neural networks, at least one of the activation or energy functions may take the form of a sigmoid function, wherein an output thereof may have a range of zero to one or 0 to 1. In other neural networks, at least one of the activation or energy functions may take the form of a hyperbolic tangent function, wherein an output thereof may have a range of negative one to positive one, or −1 to +1. Thus, the training of a neural network according to an identity function results in the redefinition or adjustment of the strengths or weights of such connections between neurons in the various layers of the neural network, in order to provide an output that most closely approximates or associates with the input to the maximum practicable extent.

Artificial neural networks may typically be characterized as either feedforward neural networks or recurrent neural networks, and may be fully or partially connected. In a feedforward neural network, e.g., a convolutional neural network, information specifically flows in one direction from an input layer to an output layer, while in a recurrent neural network, at least one feedback loop returns information regarding the difference between the actual output and the targeted output for training purposes. Additionally, in a fully connected neural network architecture, each of the neurons in one of the layers is connected to all of the neurons in a subsequent layer. By contrast, in a sparsely connected neural network architecture, the number of activations of each of the neurons is limited, such as by a sparsity parameter.

Moreover, the training of a neural network is typically characterized as supervised or unsupervised. In supervised learning, a training set comprises at least one input and at least one target output for the input. Thus, the neural network is trained to identify the target output, to within an acceptable level of error. In unsupervised learning of an identity function, such as that which is typically performed by a sparse autoencoder, target output of the training set is the input, and the neural network is trained to recognize the input as such. Sparse autoencoders employ backpropagation in order to train the autoencoders to recognize an approximation of an identity function for an input, or to otherwise approximate the input. Such backpropagation algorithms may operate according to methods of steepest descent, conjugate gradient methods, or other like methods or techniques, in accordance with the systems and methods of the present disclosure. Those of ordinary skill in the pertinent art would recognize that any algorithm or method may be used to train one or more layers of a neural network. Likewise, any algorithm or method may be used to determine and minimize the error in an output of such a network. Additionally, those of ordinary skill in the pertinent art would further recognize that the various layers of a neural network may be trained collectively, such as in a sparse autoencoder, or individually, such that each output from one hidden layer of the neural network acts as an input to a subsequent hidden layer.

Once a neural network has been trained to recognize dominant characteristics of an input of a training set, e.g., to associate an image with a label, a category, a cluster or a pseudolabel thereof, to within an acceptable tolerance, an input and/or multiple inputs, in the form of an image, silhouette, features, known traits corresponding to the image, etc., may be provided to the trained network, and an output generated therefrom. For example, the CNN discussed above may receive as inputs a generated silhouette and one or more body attributes (e.g., height, weight, gender) corresponding to the body represented by the silhouette. The trained CNN may then produce as outputs the predicted features corresponding to those inputs.

Figure 9:
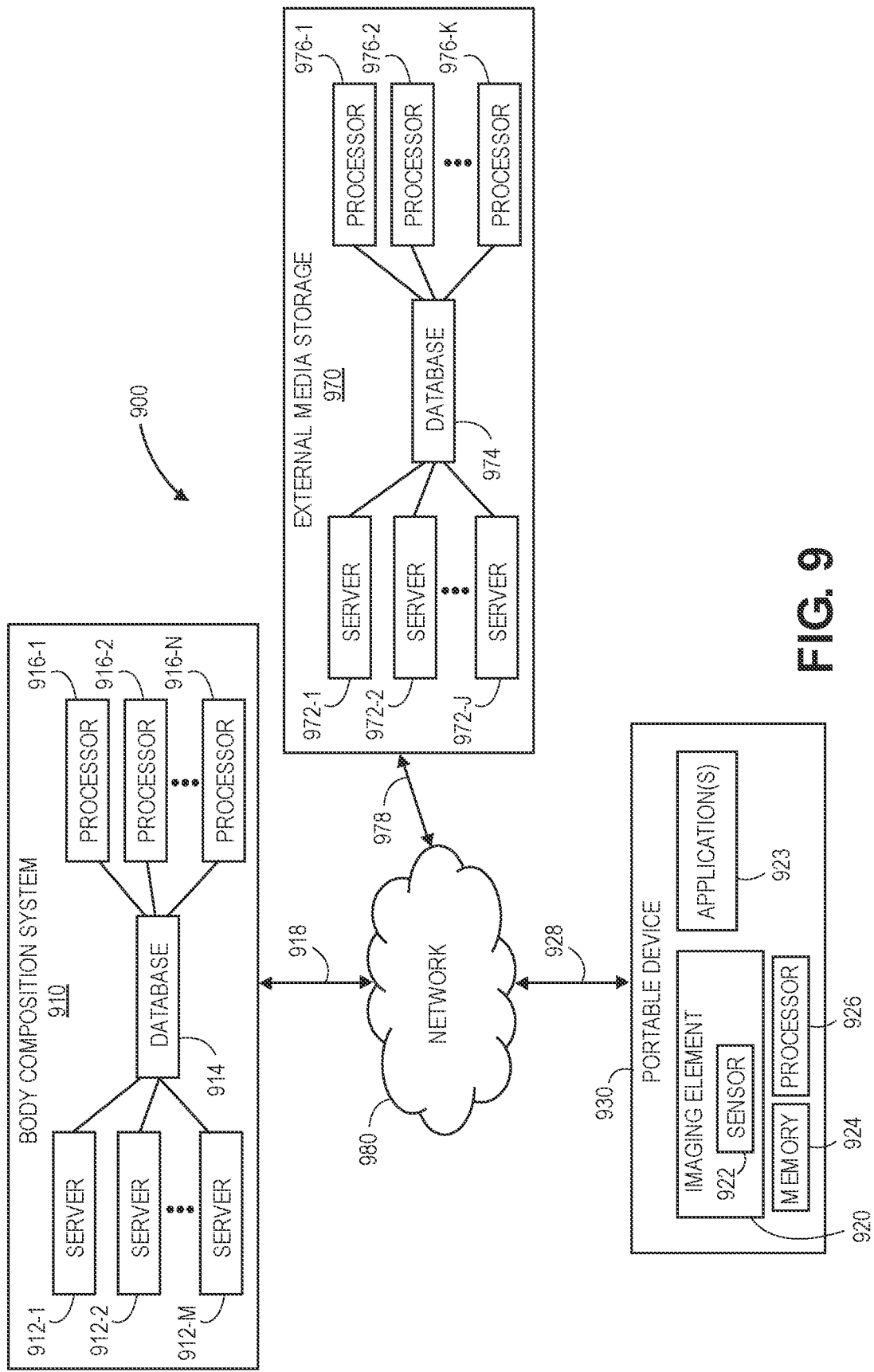
FIG. 9 is a block diagram of components of an image processing system, in accordance with implementations of the present disclosure.

Referring to FIG. 9, a block diagram of components of one image processing system 900 in accordance with implementations of the present disclosure is shown.

The system 900 of FIG. 9 includes a body composition system 910, an imaging element 920 that is part of a portable device 930 of a user, such as a tablet, a laptop, a cellular phone, a webcam, etc., and an external media storage facility 970 connected to one another across a network 980, such as the Internet.

The body composition system 910 of FIG. 9 includes M physical computer servers 912-1, 912-2 . . . 912-M having one or more databases (or data stores) 914 associated therewith, as well as N computer processors 916-1, 916-2 . . . 916-N provided for any specific or general purpose. For example, the body composition system 910 of FIG. 9 may be independently provided for the exclusive purpose of generating personalized 3D body models from 2D body images captured by imaging elements, such as imaging element 920, or silhouettes produced therefrom, or, alternatively, provided in connection with one or more physical or virtual services configured to manage or monitor such information, as well as one or more other functions. The servers 912-1, 912-2 . . . 912-M may be connected to or otherwise communicate with the databases 914 and the processors 916-1, 916-2 . . . 916-N. The databases 914 may store any type of information or data, including simulated silhouettes, body parameters, simulated 3D body models, etc. The servers 912-1, 912-2 . . . 912-M and/or the computer processors 916-1, 916-2 . . . 916-N may also connect to or otherwise communicate with the network 980, as indicated by line 918, through the sending and receiving of digital data.

The imaging element 920 may comprise any form of optical recording sensor or device that may be used to photograph or otherwise record information or data regarding a body of the user, or for any other purpose. As is shown in FIG. 9, the portable device 930 that includes the imaging element 920 is connected to the network 980 and includes one or more sensors 922, one or more memory or storage components 924 (e.g., a database or another data store), one or more processors 926, and any other components that may be required in order to capture, analyze and/or store imaging data, such as the 2D body images discussed herein. For example, the imaging element 920 may capture one or more still or moving images and may also connect to or otherwise communicate with the network 980, as indicated by the line 928, through the sending and receiving of digital data. Although the system 900 shown in FIG. 9 includes just one imaging element 920 therein, any number or type of imaging elements, portable devices, or sensors may be provided within any number of environments in accordance with the present disclosure.

The portable device 930 may be used in any location and any environment to generate 2D body images that represent a body of the user. In some implementations, the portable device may be positioned such that it is stationary and approximately vertical (within approximately ten-degrees of vertical) and the user may position their body within a field of view of the imaging element 920 of the portable device at different orientations so that the imaging element 920 of the portable device may generate 2D body images that include a representation of the body of the user from different orientations.

The portable device 930 may also include one or more applications 923 stored in memory that may be executed by the processor 926 of the portable device to cause the processor of the portable device to perform various functions or actions. For example, when executed, the application 923 may provide instructions to a user regarding placement of the portable device, positioning of the body of the user within the field of view of the imaging element 920 of the portable device, orientation of the body of the user, etc. Likewise, in some implementations, the application may present a personalized 3D body model, generated from the 2D body images in accordance with the described implementations, to the user and allow the user to interact with the personalized 3D body model. For example, a user may rotate the personalized 3D body model to view different angles of the personalized 3D body model, obtain approximately accurate measurements of the body of the user from the dimensions of the personalized 3D body model, view body fat, body mass, volume, etc. Likewise, in some implementations, the personalized 3D body model may be modified by request of the user to simulate what the body of the user may look like under certain conditions, such as loss of weight, gain of muscle, etc.

The external media storage facility 970 may be any facility, station or location having the ability or capacity to receive and store information or data, such as silhouettes, simulated or rendered personalized 3D body models of bodies, textures, body dimensions, etc., received from the body composition system 910, and/or from the portable device 930. As is shown in FIG. 9, the external media storage facility 970 includes J physical computer servers 972-1, 972-2 . . . 972-J having one or more databases 974 associated therewith, as well as K computer processors 976-1, 976-2 . . . 976-K. The servers 972-1, 972-2 . . . 972-J may be connected to or otherwise communicate with the databases 974 and the processors 976-1, 976-2 . . . 976-K. The databases 974 may store any type of information or data, including digital images, silhouettes, personalized 3D body models, etc. The servers 972-1, 972-2 . . . 972-J and/or the computer processors 976-1, 976-2 . . . 976-K may also connect to or otherwise communicate with the network 980, as indicated by line 978, through the sending and receiving of digital data.

The network 980 may be any wired network, wireless network, or combination thereof, and may comprise the Internet in whole or in part. In addition, the network 980 may be a personal area network, local area network, wide area network, cable network, satellite network, cellular telephone network, or combination thereof. The network 980 may also be a publicly accessible network of linked networks, possibly operated by various distinct parties, such as the Internet. In some implementations, the network 980 may be a private or semi-private network, such as a corporate or university intranet. The network 980 may include one or more wireless networks, such as a Global System for Mobile Communications (GSM) network, a Code Division Multiple Access (CDMA) network, a Long Term Evolution (LTE) network, or some other type of wireless network. Protocols and components for communicating via the Internet or any of the other aforementioned types of communication networks are well known to those skilled in the art of computer communications and thus, need not be described in more detail herein.

The computers, servers, devices and the like described herein have the necessary electronics, software, memory, storage, databases, firmware, logic/state machines, microprocessors, communication links, displays or other visual or audio user interfaces, printing devices, and any other input/output interfaces to provide any of the functions or services described herein and/or achieve the results described herein. Also, those of ordinary skill in the pertinent art will recognize that users of such computers, servers, devices and the like may operate a keyboard, keypad, mouse, stylus, touch screen, or other device (not shown) or method to interact with the computers, servers, devices and the like, or to "select" an item, link, node, hub or any other aspect of the present disclosure.

The body composition system 910, the portable device 930 or the external media storage facility 970 may use any web-enabled or Internet applications or features, or any other client-server applications or features including E-mail or other messaging techniques, to connect to the network 980, or to communicate with one another, such as through short or multimedia messaging service (SMS or MMS) text messages. For example, the servers 912-1, 912-2 . . . 912-M may be adapted to transmit information or data in the form of synchronous or asynchronous messages from the body composition system 910 to the processor 926 or other components of the portable device 930, or any other computer device in real time or in near-real time, or in one or more offline processes, via the network 980. Those of ordinary skill in the pertinent art would recognize that the body composition system 910, the portable device 930 or the external media storage facility 970 may operate any of a number of computing devices that are capable of communicating over the network, including but not limited to set-top boxes, personal digital assistants, digital media players, web pads, laptop computers, desktop computers, electronic book readers, cellular phones, and the like. The protocols and components for providing communication between such devices are well known to those skilled in the art of computer communications and need not be described in more detail herein.

The data and/or computer executable instructions, programs, firmware, software and the like (also referred to herein as "computer executable" components) described herein may be stored on a computer-readable medium that is within or accessible by computers or computer components such as the servers 912-1, 912-2 . . . 912-M, the processor 926, the servers 972-1, 972-2 . . . 972-J, or any other computers or control systems utilized by the body composition system 910, the portable device 930, applications 923, or the external media storage facility 970, and having sequences of instructions which, when executed by a processor (e.g., a central processing unit, or "CPU"), cause the processor to perform all or a portion of the functions, services and/or methods described herein. Such computer executable instructions, programs, software and the like may be loaded into the memory of one or more computers using a drive mechanism associated with the computer readable medium, such as a floppy drive, CD-ROM drive, DVD-ROM drive, network interface, or the like, or via external connections.

Some implementations of the systems and methods of the present disclosure may also be provided as a computer-executable program product including a non-transitory machine-readable storage medium having stored thereon instructions (in compressed or uncompressed form) that may be used to program a computer (or other electronic device) to perform processes or methods described herein. The machine-readable storage media of the present disclosure may include, but is not limited to, hard drives, floppy diskettes, optical disks, CD-ROMs, DVDs, ROMs, RAMs, erasable programmable ROMs ("EPROM"), electrically erasable programmable ROMs ("EEPROM"), flash memory, magnetic or optical cards, solid-state memory devices, or other types of media/machine-readable medium that may be suitable for storing electronic instructions. Further, implementations may also be provided as a computer executable program product that includes a transitory machine-readable signal (in compressed or uncompressed form). Examples of machine-readable signals, whether modulated using a carrier or not, may include, but are not limited to, signals that a computer system or machine hosting or running a computer program can be configured to access, or including signals that may be downloaded through the Internet or other networks.

Figure 10:
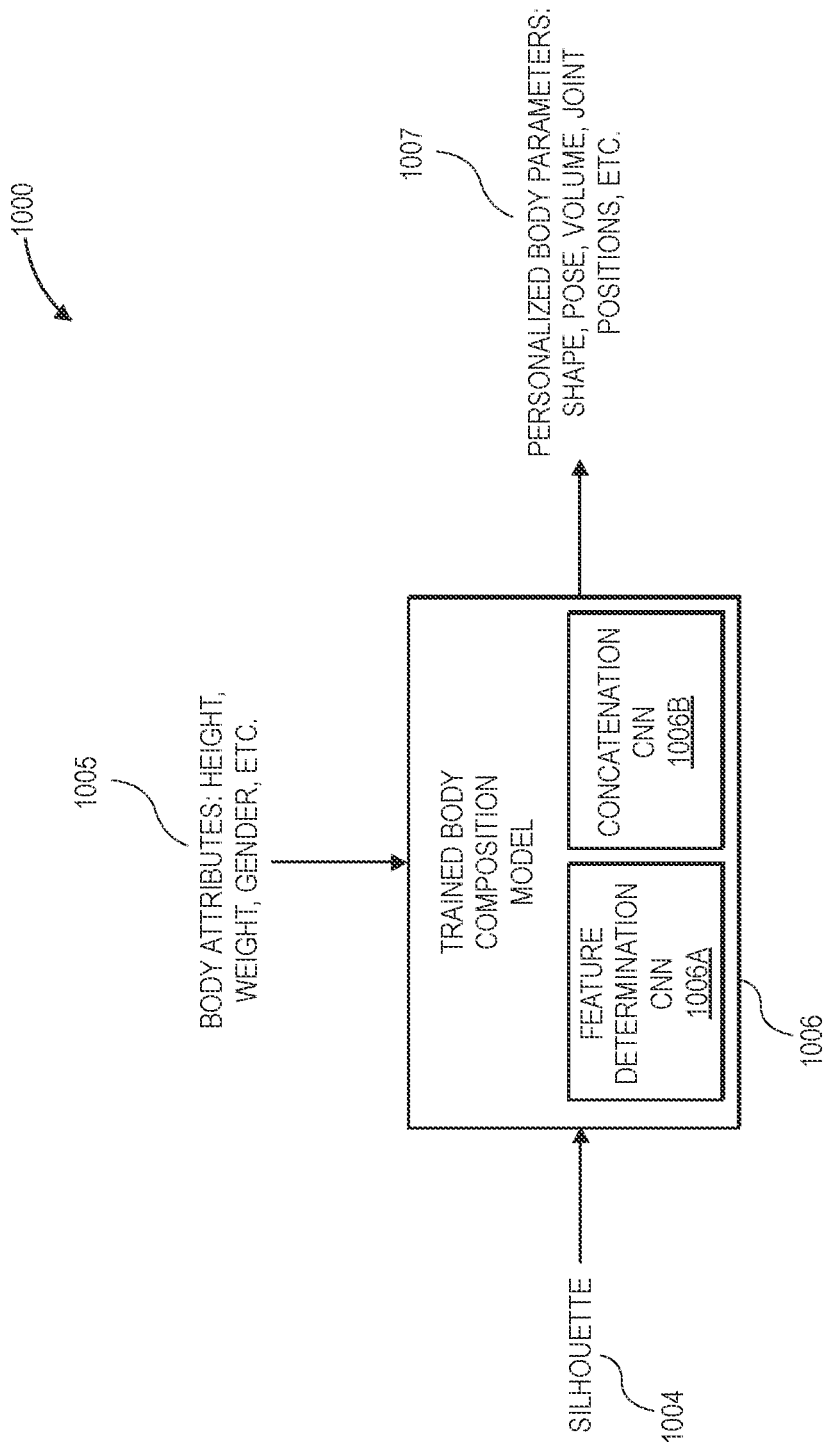
FIG. 10 is a block diagram of a trained body composition model that determines body parameters of a body represented in two-dimensional body images, in accordance with implementations of the present disclosure.

FIG. 10 is a block diagram of a trained body composition model 1000 that determines body parameters 1007 of a body represented in two-dimensional images, in accordance with implementations of the present disclosure. As discussed above, the model 1000 may be a neural network, such as a CNN that is trained to receive one or more inputs that are processed to generate one or more outputs, such as the body parameters 1007. In the illustrated example, the trained body composition model 1006 may include several component CNNs that receive different inputs and provide different outputs. Likewise, outputs from one of the component CNNs may be provided as an input to one or more other component CNNs of the trained body composition model. For example, the trained body composition model may include two parts of component CNNs. In one implementation, a first component part may include one or more feature determination CNNs 1006A and a second component part may include a concatenation CNN 1006B. In the illustrated example, there may be different feature determination CNNs 1006A for each of the different body orientations (e.g., front view, right side view, back view, left side view, three-quarter view), different silhouettes 1004 corresponding to those different body orientations, and/or different 2D body images corresponding to those different body orientations, each CNN trained for inputs having the particular orientation. Likewise, in some implementations, the feature determination CNNs 1006A may receive multiple different types of inputs. For example, in addition to receiving a silhouette 1004 and/or 2D body image, each feature determination CNN 1006A may receive one or more body attributes 1005 corresponding to the body represented by the silhouettes 1004 and/or 2D body images. The body attributes 1005 may include, but are not limited to, height, weight, gender, etc. As discussed, the trained feature determination CNNs 1006A process the inputs and generate features representative of the bodies represented in the 2D body images that were used to produce the silhouettes 1004. For example, if there are four silhouettes, one for a front view, one or a right side view, one for a back view, and one for a left side view, the four feature determination CNNs 1006A trained for those views each produce a set of features representative of the body represented in the 2D body image used to generate the silhouette.

Utilizing binary silhouettes 1004 of bodies improves the accuracy of the feature determination CNN 1006A as it can focus purely on size, shape, dimensions, etc. of the body, devoid of any other aspects (e.g., color, clothing, hair, etc.). In other implementations, the use of the 2D body images in conjunction with or independent of the silhouettes provides additional data, such as shadows, skin tone, etc., that the feature determination CNN 1006A may utilize in determining and producing a set of features representative of the body represented in the 2D body image.

The features output from the feature determination CNNs 1006A, in the disclosed implementation, are received as inputs to the concatenation CNN 1006B. Likewise, in some implementations, the concatenation CNN 1006B may be trained to receive other inputs, such as body attributes 1005.

As discussed, the concatenation CNN 1006B may be trained to receive the inputs of features, and optionally other inputs, produce concatenated features, and produce as outputs a set of body parameters 1007 corresponding to the body represented in the 2D body images. In some implementations, the body parameters may include hundreds of parameters, including, but not limited to, shape, pose, volume, joint position, etc., of the represented body.

Figure 11:
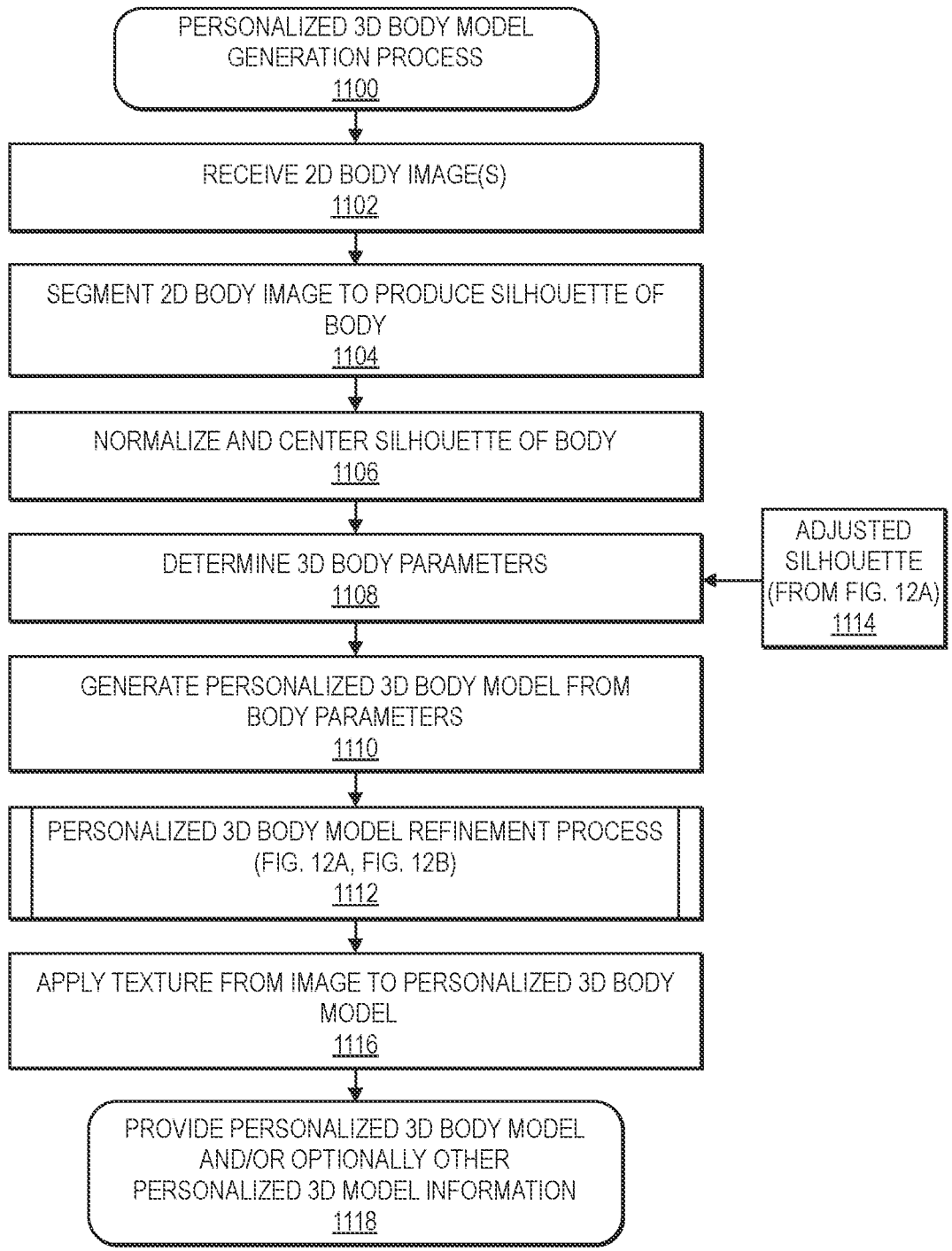
FIG. 11 is an example flow diagram of a three-dimensional body model generation process, in accordance with implementations of the present disclosure.

FIG. 11 is an example flow diagram of a personalized 3D body model generation process 1100, in accordance with implementations of the present disclosure.

The example process 1100 begins upon receipt of one or more 2D body images of a body, as in 1102. As noted above, the disclosed implementations are operable with any number of 2D body images for use in generating a personalized 3D body model of that body. For example, in some implementations, a single 2D body image may be used. In other implementations, two, three, four, or more 2D body images may be used.

As discussed above, the 2D body images may be generated using any 2D imaging element, such as a camera on a portable device, a webcam, etc. The received 2D body images are then segmented to produce a binary silhouette of the body represented in the one or more 2D body images, as in 1104. As discussed above, one or more segmentation techniques, such as background subtraction, semantic segmentation, Canny edge detectors or algorithms, Sobel operators, algorithms or filters, Kayyali operators, Roberts edge detection algorithms, Prewitt operators, Frei-Chen methods, or any other algorithms or techniques that may be known to those of ordinary skill in the pertinent arts.

In addition, in some implementations, the silhouettes may be normalized in height and centered in the image before further processing, as in 1106. For example, the silhouettes may be normalized to a standard height based on a function of a known or provided height of the body of the user represented in the image and an average height (e.g., average height of female body, average height of male body). In some implementations, the average height may be more specific than just gender. For example, the average height may be the average height of a gender and a race corresponding to the body, or a gender and a location (e.g., United States) of the user, etc.

The normalized and centered silhouette may then be processed by one or more neural networks, such as one or more CNNs as discussed above, to generate body parameters representative of the body represented in the 2D body images, as in 1108. As discussed above, there may be multiple steps involved in body parameter prediction. For example, each silhouette may be processed using CNNs trained for the respective orientation of the silhouette to generate sets of features of the body as determined from the silhouette. The sets of features generated from the different silhouette may then be processed using a neural network, such as a CNN, to concatenate the features and generate the body parameters representative of the body represented in the 2D body images.

The body parameters may then be provided to one or more body models, such as an SMPL body model or a SCAPE body model and the body model may generate a personalized 3D body model for the body represented in the 2D body images, as in 1110. In addition, in some implementations, the personalized 3D body model may be revised, if necessary, to more closely correspond to the actual image of the body of the user, as in 1200. Personalized 3D body model refinement is discussed above, and discussed further below with respect FIGS. 12A and 12B.

As discussed below, the personalized 3D body model refinement process 1200 (FIG. 12A) returns an adjusted silhouette, as in 1114. Upon receipt of the adjusted silhouette, the example process 1100 again generates body parameters, as in 1108, and continues. This may be done until no further refinements are to be made to the silhouette. In comparison, the personalized 3D body model refinement process 1250 (FIG. 12B) generates and returns and adjusted personalized 3D body model and the example process 1100 continues at block 1116.

Figure 12A:
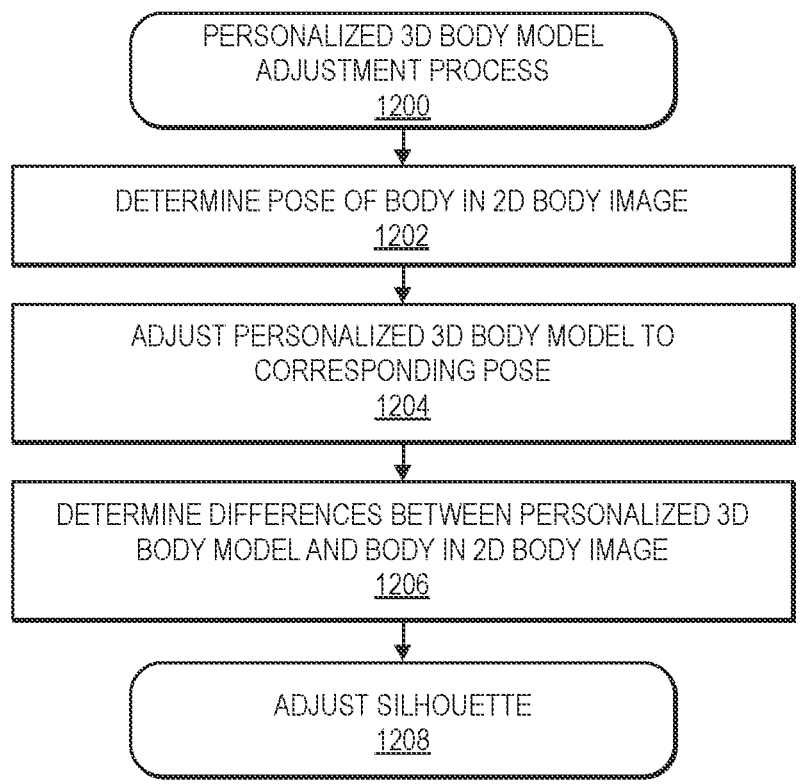
FIG. 12A is an example flow diagram of a three-dimensional body model adjustment process, in accordance with implementations of the present disclosure.
Figure 12B:
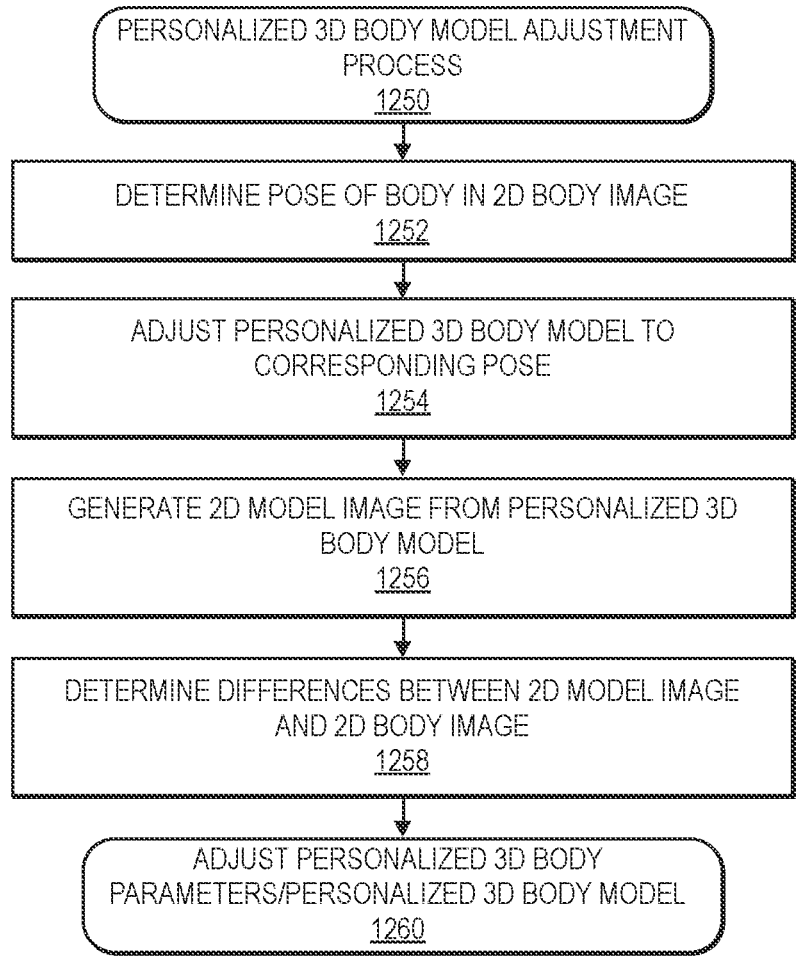
FIG. 12B is another example flow diagram of a three-dimensional body model adjustment process, in accordance with implementations of the present disclosure.

After adjustment of the silhouette and generation of a personalized 3D body model from adjusted body parameters, or after receipt of the adjusted personalized 3D body model from FIG. 12B, one or more textures (e.g., skin tone, hair, clothing, etc.) from the 2D body images may be applied to the personalized 3D body model, as in 1116. Finally, the personalized 3D body model may be provided to the user as representative of the body of the user and/or other personalized 3D body model information (e.g., body mass, joint locations, arm length, body fat percentage, etc.) may be determined from the model, as in 1118.

FIG. 12A is an example flow diagram of a personalized 3D body model adjustment process 1200, in accordance with implementations of the present disclosure. The example process 1200 begins by determining a pose of a body represented in one of the 2D body images, as in 1202. A variety of techniques may be used to determine the approximate pose of the body represented in a 2D body image. For example, camera parameters (e.g., camera type, focal length, shutter speed, aperture, etc.) included in the metadata of the 2D body image may be obtained and/or additional camera parameters may be determined and used to estimate the approximate pose of the body represented in the 2D body image. For example, a personalized 3D body model may be used to approximate the pose of the body in the 2D body image and then a position of a virtual camera with respect to that model that would produce the 2D body image of the body may be determined. Based on the determined position of the virtual camera, the height and angle of the camera used to generate the 2D body image may be inferred. In some implementations, the camera tilt may be included in the metadata and/or provided by a portable device that includes the camera. For example, many portable devices include an accelerometer and information from the accelerometer at the time the 2D body image was generated may be provided as the tilt of the camera. Based on the received and/or determined camera parameters, the pose of the body represented in the 2D body image with respect to the camera may be determined, as in 1202.

The personalized 3D body model of the body of the user may then be adjusted to correspond to the determined pose of the body in the 2D body image, as in 1204. With the personalized 3D body model adjusted to approximately the same pose as the user represented in the image, the shape of the personalized 3D body model may be compared to the shape of the body in the 2D body image and/or the silhouette to determine any differences between the personalized 3D body model and the representation of the body in the 2D body image and/or silhouette, as in 1206.

In some implementations, it may be determined whether any determined difference is above a minimum threshold (e.g., 2%). If it is determined that there is a difference between the personalized 3D body model and the body represented in one or more of the 2D body images, the silhouette may be adjusted. The silhouette may then be used to generate revised body parameters for the body represented in the 2D body images, as discussed above with respect to FIG. 11. If the silhouette is revised, the revised silhouette is returned to the example process 1100, as discussed above and as illustrated in block 1114 (FIG. 11). If no difference is determined or if it is determined that the difference does not exceed a minimum threshold, an indication may be returned to the example process 1100 that there are no differences between the personalized 3D body model and the 2D body image/silhouette.

FIG. 12B is an example flow diagram of another personalized 3D body model adjustment process 1250, in accordance with implementations of the present disclosure. The example process 1250 begins by determining a pose of a body represented in one of the 2D body images, as in 1252. A variety of techniques may be used to determine the approximate pose of the body represented in a 2D body image. For example, camera parameters (e.g., camera type, focal length, shutter speed, aperture, etc.) included in the metadata of the 2D body image may be obtained and/or additional camera parameters may be determined and used to estimate the approximate pose of the body represented in the 2D body image. For example, a personalized 3D body model may be used to approximate the pose of the body in the 2D body image and then a position of a virtual camera with respect to that model that would produce the 2D body image of the body may be determined. Based on the determined position of the virtual camera, the height and angle of the camera used to generate the 2D body image may be inferred. In some implementations, the camera tilt may be included in the metadata and/or provided by a portable device that includes the camera. For example, many portable devices include an accelerometer and information from the accelerometer at the time the 2D body image was generated may be provided as the tilt of the camera. Based on the received and/or determined camera parameters, the pose of the body represented in the 2D body image with respect to the camera may be determined, as in 1252.

The personalized 3D body model of the body of the user may then be adjusted to correspond to the determined pose of the body in the 2D body image, as in 1254. With the personalized 3D body model adjusted to approximately the same pose as the user represented in the image, a 2D model image from the personalized 3D body model is generated, as in 1256. The 2D model image may be generated, for example, by converting or imaging the personalized 3D body model into a 2D image with the determined pose, as if a digital 2D image of the personalized 3D body model had been generated. Likewise, the 2D model image may be a binary image with pixels corresponding to the model having a first set of values (e.g., white—RGB values of 255, 255, 255) and pixels that do not represent the model having a second set of values (e.g., black—RGB values of 0, 0, 0)

The 2D model image is then compared with the 2D body image and/or the silhouette to determine any differences between the 2D model image and the representation of the body in the 2D body image and/or silhouette, as in 1258. For example, the 2D model image may be aligned with the 2D body image and/or the silhouette and pixels between the images compared to determine differences between the pixels values. In implementations in which the pixels are binary (e.g., white or black) an error (e.g., % difference) may be determined as a difference in pixel values between the 2D model image and the 2D body image. That error is differentiable and may be utilized to adjust the body parameters and, as a result, the shape of the personalized 3D body model.

In some implementations, it may be determined whether any determined difference is above a minimum threshold (e.g., 2%). If it is determined that there is a difference between the 2D model image and the body represented in one or more of the 2D body images/silhouette, the personalized 3D body model and/or the body parameters may be adjusted to correspond to the shape and/or size of body represented in the 2D body image and/or the silhouette, as in 1260. This example process 1250 may continue until there is no difference between the 2D model image and the 2D body image/silhouette, or the difference is below a minimum threshold. As discussed above, the revised personalized 3D body model produced from the example process 1250, or if no adjustment are necessary, the personalized 3D body model is returned to example process 1100 at block 1112 and the process 1100 continues.

Figure 13:
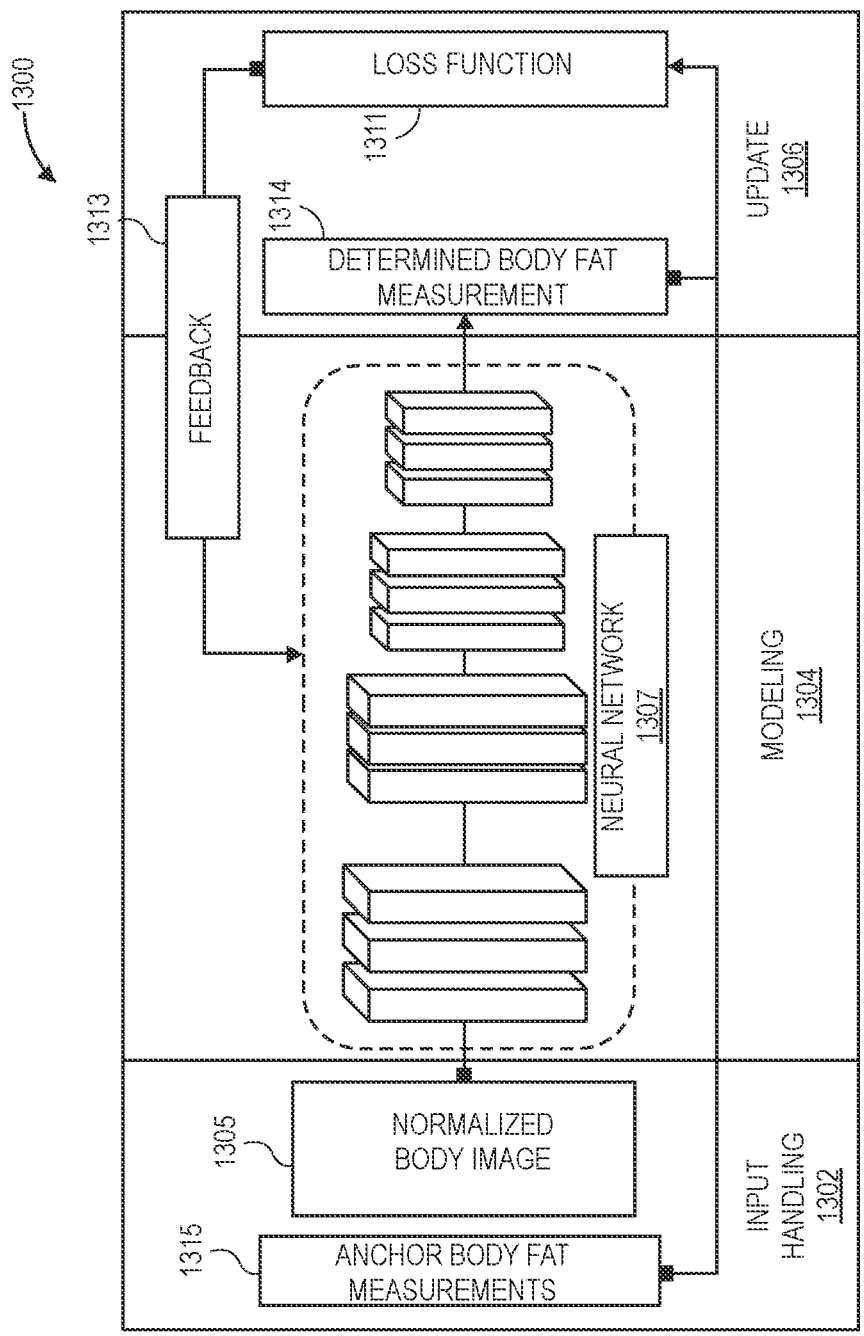
FIG. 13 is a block diagram of an example system operable to determine body fat measurements from a two-dimensional body image, in accordance with implementations of the present disclosure.

FIG. 13 is a block diagram of an example system 1300 operable to determine body fat measurements 1314 from a 2D body image, in accordance with implementations of the present disclosure. As discussed above, the input 2D body image may include a representation of an entire body or a representation of a portion of the body (e.g., head, torso, leg, arm, head to knee, neck to knee, neck to torso, etc.). Likewise, while the discussions herein focus primarily on receiving and processing a 2D body image, the disclosed implementations may likewise be used with 2D video. In such an implementation, a frame from the video may be extracted and processed with the disclosed implementations to determine body fat measurements for a body represented in the extracted frame.

Each component of the system 1300 may be performed as computer executable instructions executing on a computing device, such as the computing resources 103/203 (FIGS. 1A, 1B, 2) and/or the portable device 130/230 (FIGS. 1A, 1B, 2). In some implementations, all aspects of the system may execute on one set of computing resources, such as the computing resources 103/203 or the portable device 130/230. In other implementations, a first portion of the system 1300 may execute on one set of computing resources, such as the portable device 130/230 while a second portion of the system 1300 executes on a second set of computing resources, such as the computing resources 103/203.

Regardless of the source, the 2D body image is received by an input handling component 1302. The input handling component, as discussed in further detail below with respect to FIGS. 15 and 16, processes the received 2D body image and produces a normalized body image 1305. The normalized body image is of a defined size, such as 640×256 pixels by 3 channels (red, green, blue). Likewise, pixels that do not represent the body may be suppressed by setting their color values to a defined color, such as black (0,0,0). The normalized body image decreases the number of input variations into the remainder of the system 1300.

The normalized body image is then passed to a modeling component 1304 that may include one or more neural networks 1307. For example, the neural network 1307 may be a modified version of a residual network, such as ResNet-50. Residual learning, or a residual network, such as ResNet-50 utilizes several layers or bottlenecks that are stacked and trained to the task to be performed (such as image classification). The network learns several low/mid/high level features at the end of its layers. In residual learning, the neural network 1307 is trained to learn the residual of each bottleneck. A residual can be simply understood as a subtraction of the feature learned from input of that layer. Some residual networks, such as ResNet-50 do this by connecting the output of one bottleneck to the input of another bottleneck.

As discussed further below, the disclosed implementations modify the residual network by extracting the features learned in each layer and concatenating those features with the output of the network to determine a body fat measurement value 1314 of the body represented in the received 2D body image. The neural network 1307 is discussed in further detail below with respect to FIGS. 17 and 18.

In addition to determining a body fat measurement value 1314 of the body represented in the 2D image, in some implementations, an update component 1306 may be used to determine one or more loss functions 1311 from the determined body fat measurements and from anchor body fat measurements 1315 that are maintained by the system 1300. Anchor body fat measurements, as discussed further below, may be baseline or known body fat measurements for different images, different body parts, body fat measurements corresponding to different body shapes, muscle definitions, etc. The determined loss functions 1311 may be fed back into the modeling component 1304 and/or directly to the neural network 1307 as a feedback 1313. The feedback may be used to improve the accuracy of the system 1300. Loss functions are discussed in greater detail below with respect to FIG. 19.

In some implementations, additional information may be received by the system 1300 and used as additional inputs to the system 1300. For example, additional information about the body, such as age, gender, ethnicity, height, weight, etc., may also be received as inputs and used by the neural network 1307 in determining a body fat measurement representation and/or a body fat measurement value, as discussed herein.

Figure 14:
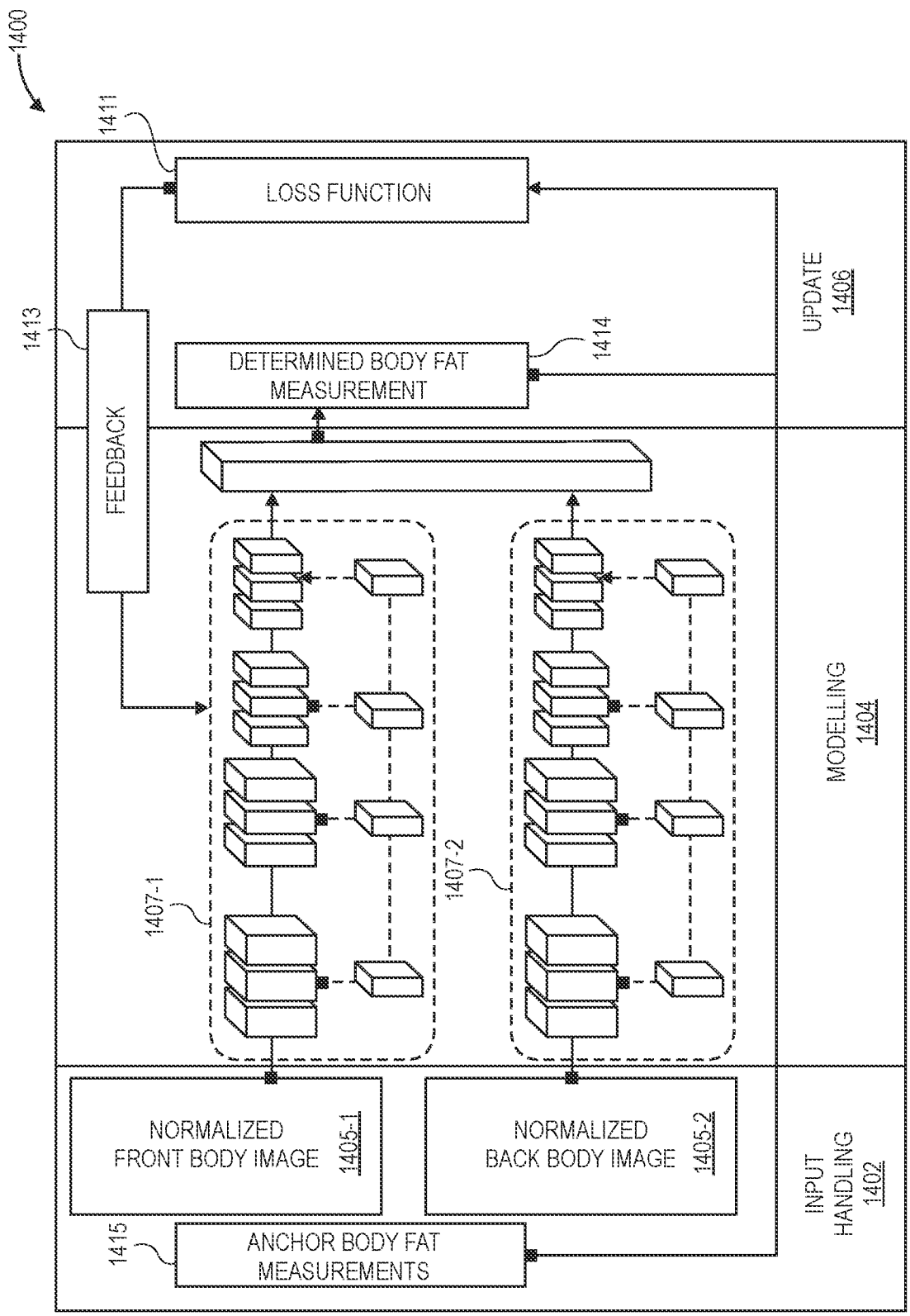
FIG. 14 is a block diagram of an example system operable to determine body fat measurements from multiple two-dimensional body images, in accordance with implementations of the present disclosure.

FIG. 14 is a block diagram of another example system 1400 operable to determine body fat measurements from multiple 2D body images, in accordance with implementations of the present disclosure.

In the example illustrated in FIG. 14, multiple input images are received by the input handling component 1402 and each image is processed, as discussed below, to generate respective normalized body images. For example, if a first image is a front side view image, the front side view image may be processed by the input handling component 1402 to produce a normalized front body image 1405-1. Likewise, if the second image is a back side view image, the back side view image may be processed by the input handling component 1402 to produce a normalized back body image 1405-2.

Each normalized body image 1405 is passed to the modeling component 1404 and processed by one or more neural networks, such as neural network 1407-1 or neural network 1407-2 to determine respective body fat measurement values. The outputs of those processes may be combined to produce a single body fat measurement value 1414 representative of the body represented in the input images.

In addition, the determined body fat measurement may be processed by an update component 1406 along with anchor body measurements 1415 to determine one or more loss functions 1411 that are provided as feedback 1413 to the modeling component and/or the neural networks 1407 to improve the accuracy of the system 1400. In some implementations the final body fat measurement value 1414 may be processed by the update component 1406 to determine the loss functions. In other implementations, the determined body fat measurement representations determined for each of the normalized body images may be individually processed by the update component 1406 and the respective loss function provided as feedback 1413 to the respective portion of the modeling component and/or the neural network that processed the normalized body image. For example, the update component may determine a first loss function based on the determined body fat measurement generated by the neural network 1407-1 and provide first loss functions as first feedback to the neural network 1407-1. Likewise, the update component 1406 may also determine a second loss function based on the determined body fat measurement generated by the neural network 1407-2 and provide the second loss functions as second feedback to the neural network 1407-2.

In still other examples, rather than utilizing a single neural network to process each received normalized input image, neural networks may be trained to process a combination of normalized input images to determine a body fat measurement value. For example, if the combination of front side view body image and back side view body image is often received, a single neural network may be trained to process both normalized body images concurrently to determine a body fat measurement value from the two images. In other implementations, other combinations of images, body directions in the images, or number of images may likewise be used to train a neural network for processing those images and determining a body fat measurement for the body represented in those images.

In some implementations, additional information may be received by the system 1400 and used as additional inputs to the system 1400. For example, additional information about the body, such as age, gender, ethnicity, height, weight, etc., may also be received as inputs and used by the neural networks 1407 in determining a measured visual body fat representation and/or a body fat measurement value, as discussed herein.

In some implementations, the system 1300/1400 may also produce other outputs in addition to the body fat measurement representations and/or body fat measurement values. For example, in some implementations, the disclosed implementations may also produce information indicating the age, gender, ethnicity, body mass index, height, weight, body dimensions (e.g., arm length, waist circumference, leg circumference, etc.).

Figure 15:
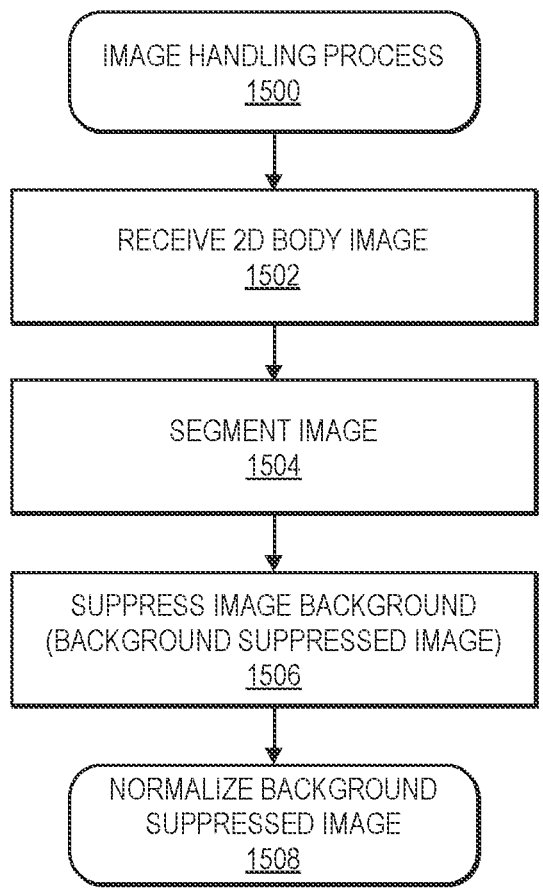
FIG. 15 is an example two-dimensional body image handling process, in accordance with implementations of the present disclosure.

FIG. 15 is an example 2D body image handling process 1500, in accordance with implementations of the present disclosure. The example process 1500 may be performed by the input handing component 1302/1402 discussed above in FIGS. 13 and 14.

The example process 1500 begins upon receipt of a 2D body image, as in 1502. The 2D body image may be received directly from a 2D camera or may be one of the 2D body images selected from the body direction determination and body direction image selection process 600 (FIG. 6) discussed above.

Regardless of the source, the received 2D body image is segmented and the pixels that correspond to a background are suppressed to isolate the body represented in the image and produce a background suppressed image, as in 1504 and 1506. For example, referring now to FIG. 16, input image 1610, which in this example is a 2D body image 1601, may be processed to segment 1612 pixels of the image that represent the body 1600 from pixels of the image that do not represent the body, referred to herein as background 1602-1/1602-2 pixels, to produce an image that only includes a representation of the body 1600, as represented in the segmented image 1603. Segmentation may be done through, for example, background subtraction, semantic segmentation, etc. In one example, a baseline image of the background may be known and used to subtract out pixels of the image that correspond to pixels of the baseline image, thereby leaving only foreground pixels that represent the body. The background pixels may be assigned RGB color values for black (i.e., 0,0,0).

In another example, a neural network utilizing a semantic segmentation algorithm may be trained using images of bodies, such as human bodies, or simulated human bodies to train the neural network to distinguish between pixels that represent human bodies and pixels that do not represent human bodies. In such an example, the neural network may process the received image 1601 and indicate or label pixels that represent portions of the body, such as hair, body, hands, feet, upper-clothing, lower-clothing, and pixels that do not represent the body (background). The background pixels 1602-1/1602-2 may be assigned RGB color values for black (i.e., 0,0,0).

In other implementations, other forms or algorithms, such as edge detection, shape detection, etc., may be used to determine pixels of the image that represent the body and pixels of the image that do not represent the body and pixels that do not represent the body suppressed.

Returning to FIG. 15, the background suppressed image is then normalized to produce a normalized body image, as in 1508. Referring again to FIG. 16, background suppressed image 1603 is normalized 1614 to produce a normalized body image 1605 that is of a defined size, such as 640×256 pixels, with three channels (Red, Green, Blue). Producing the normalized body image may include rescaling the body 1600 to fill a bounding box of the defined size and then setting the normalized body image to that bounding box so that the body is resized and centered in the image.

Figure 17:
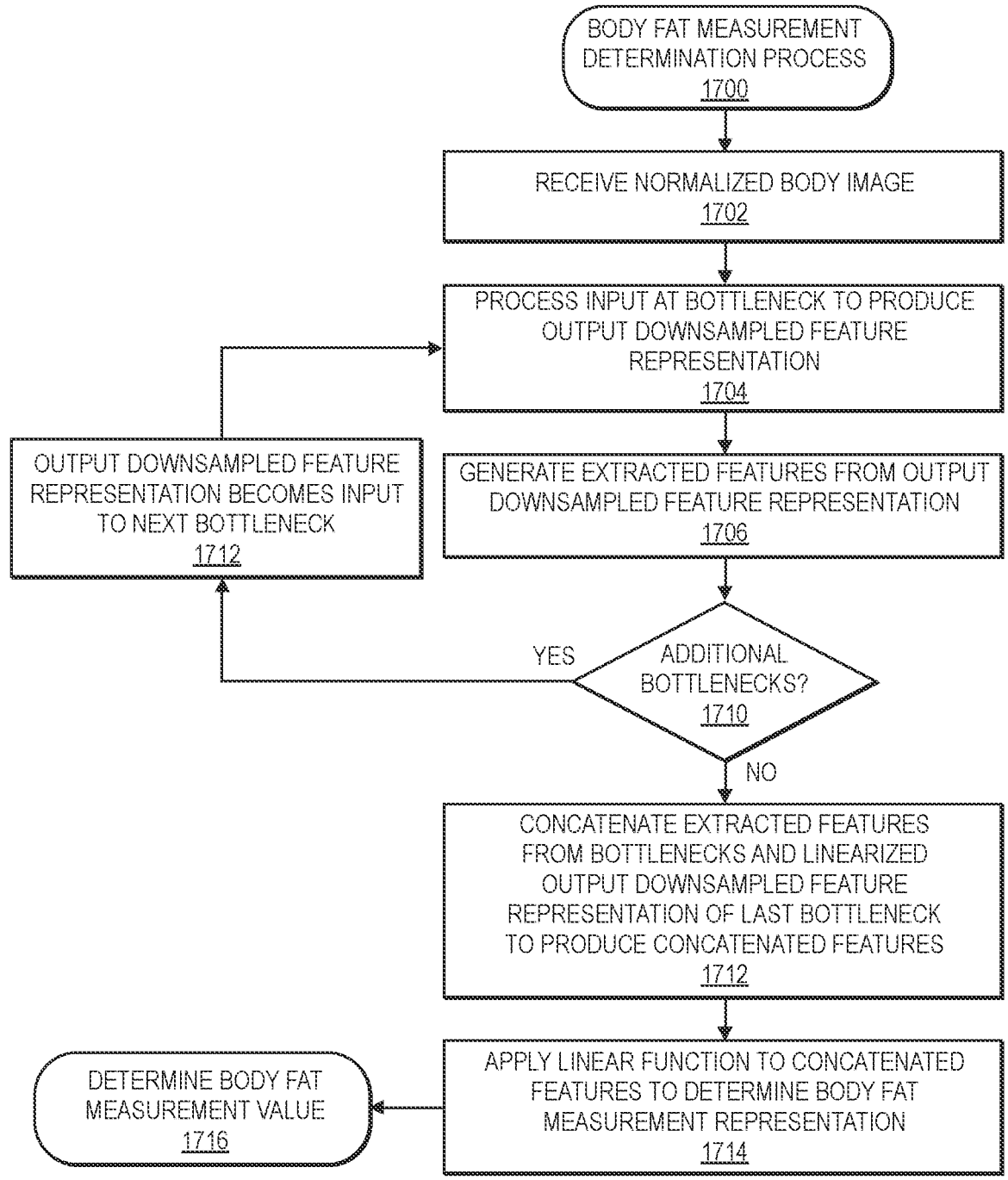
FIG. 17 is an example body fat measurement determination process, in accordance with implementations of the present disclosure.

FIG. 17 is an example body fat measurement determination process 1700, in accordance with implementations of the present disclosure. The example body fat measurement determination process may be performed by the modeling component 1304/1404 (FIGS. 13 and 14) discussed above. For example, the body fat measurement determination process 1700 may be performed by the modified neural network 1307/1407 discussed above.

Figure 16:
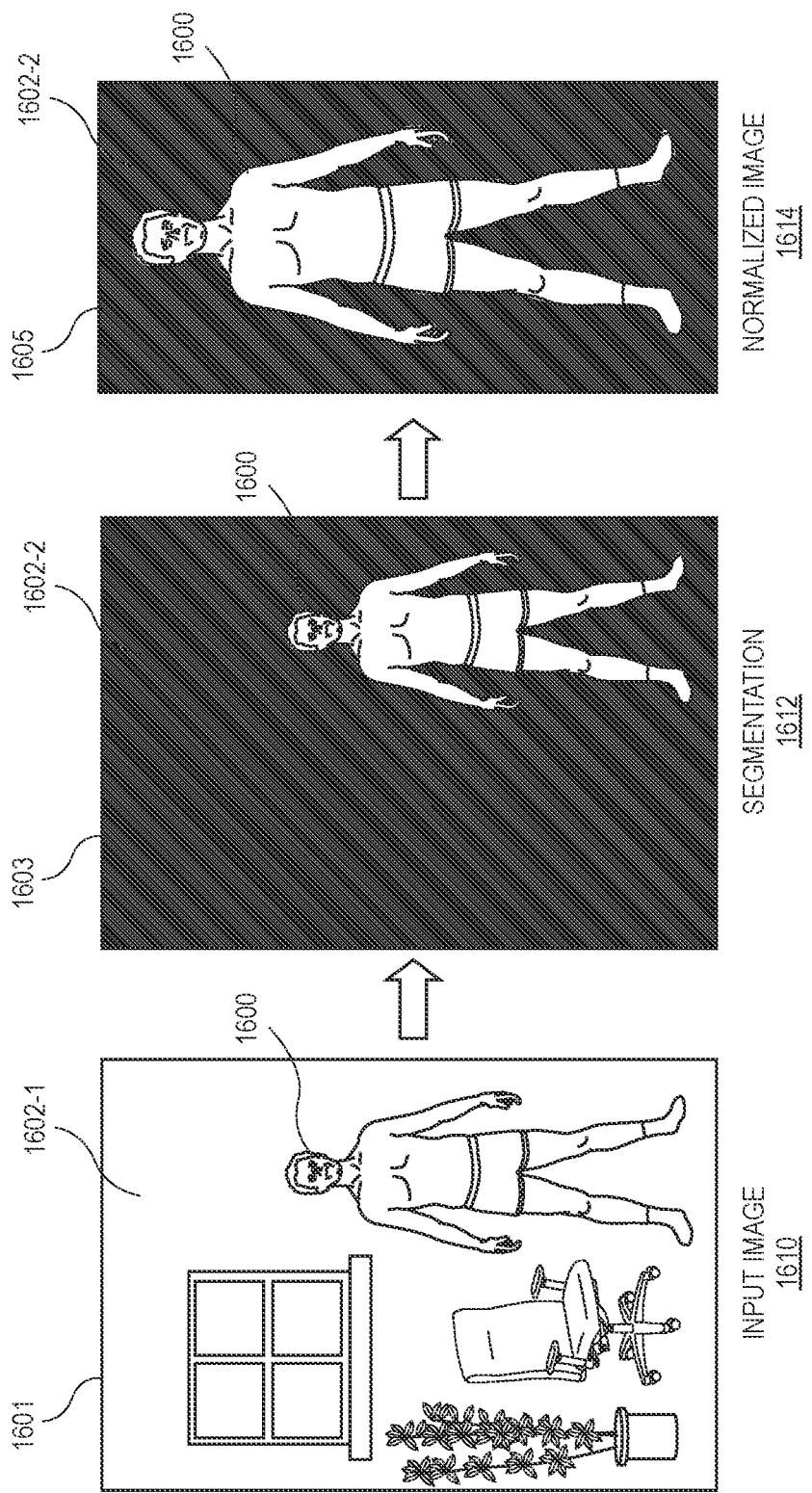
FIG. 16 is an example of image handling of a two-dimensional body image, in accordance with implementations of the present disclosure.

The example process 1700 begins upon receipt of the normalized body image, as in 1702. The normalized body image may be, for example, the normalized body image produced from the example process 1600 (FIG. 16).

The normalized body image is processed as an input to a first bottleneck of the neural network and the first bottleneck outputs a downsampled feature representation, as in 1704. For example, referring to FIG. 18, illustrated is an example system 1800 that includes a neural network 1807 configured to determine body fat measurements from a normalized 2D image, in accordance with implementations of the present disclosure.

Figure 18:
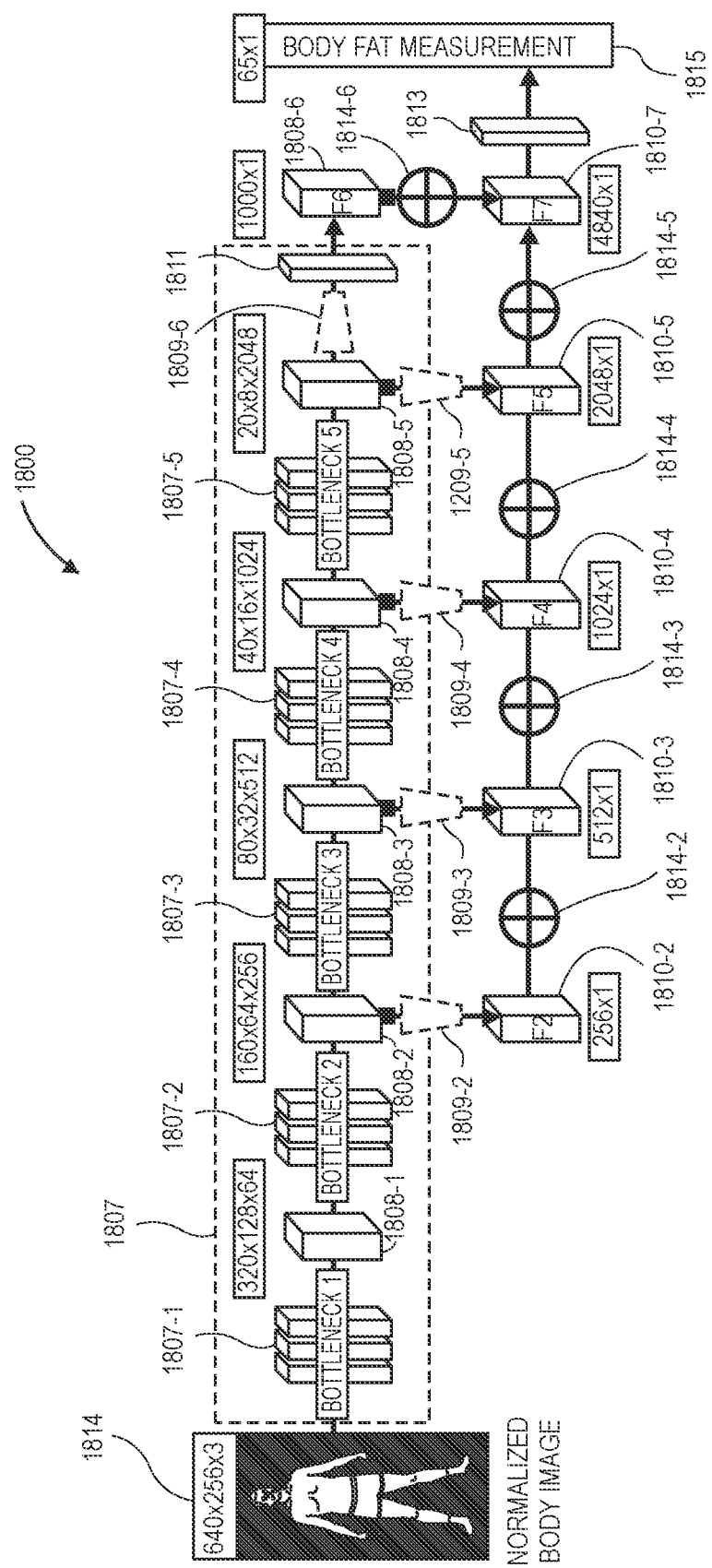
FIG. 18 is an example neural network configured to determine body fat measurements from a normalized two-dimensional image, in accordance with implementations of the present disclosure.

FIG. 18 illustrates an example neural network, such as ResNet-50, modified as discussed herein. In the illustrated example, the neural network 1807 includes five bottlenecks 1807-1, 1807-2, 1807-3, 1807-4, and 1807-5, each of which process an input and generate a downsampled feature representation as an output. Each bottleneck is a stack of deep-learning units, such as convolution layers, non-linear activation functions (Rectified Linear Units ("ReLU")), pooling operations (MaxPooling, Average Pooling) and batch normalization.

In the illustrated example, each bottleneck 1807-1 through 1807-5 reduces the spatial resolution of the input by a factor of two. In other implementations, the spatial resolution may be downsampled differently.

The first bottleneck 1807-1 receives the normalized body image 1814 as the input and reduces the spatial resolution of the normalized body image from 640×256, by a factor of two, down to 320×128. Likewise, in this example, the channels are increased to 64 channels. In other implementations, channel increase may be different based on, for example, computing capacity, computation time, etc. Accordingly, in this example, the output of the first bottleneck 1807-1 is a feature representation 1808-1 with a height of 320, a width of 128, and 64 channels.

Referring back to FIG. 17, the example process 1700 then generates extracted features from the downsampled feature representation, as in 1706. For example, the features from any one or more bottlenecks may be extracted by averaging the outputs of the bottleneck across the spatial dimensions. For example, referring again to FIG. 18, if the features are extracted from the output 1808-1 of the first bottleneck 1807-1, the 64 feature channels are averaged across the 320×128 spatial dimensions to get $F_1 \in 64 \times 1$. In some implementations, features may not be extracted from all bottlenecks of the neural network. For example, as illustrated in FIG. 18, features may not be extracted from the first output of the first bottleneck for use in determining the body fat measurement. In other examples, features may not be extracted from other bottlenecks of the neural network. In comparison, in some implementations, features may be extracted from all bottleneck outputs and utilized with the disclosed implementations.

As the features are extracted, a determination is made as to whether additional bottlenecks remain to be processed, as in 1710. If it is determined that additional bottlenecks remain, the downsampled feature representation from the upstream bottleneck is used as the input to the next bottleneck, as in 1712, and the process 1700 continues.

For example, referring again to FIG. 18, the first downsampled feature representation 1808-1 output from the first bottleneck 1807-1 is provided as an input to the second bottleneck 1807-2. The second bottleneck 1807-2 receives the first downsampled feature representation 1808-1, which has spatial dimensions of 320×128, and 64 channels and processes that input to produce a second downsampled feature representation 1808-2 that has spatial dimensions of 160×64 and 256 channels. As the example process 1700 (FIG. 17) continues, the third bottleneck 1807-3 receives the second downsampled feature representation 1808-2 and processes that input to produce a third downsampled feature representation 1808-3 that has spatial dimensions of 80×32 and 512 channels. The fourth bottleneck 1807-4 receives the third downsampled feature representation 1808-3 and processes that input to produce a fourth downsampled feature representation 1808-4 that has spatial dimensions of 40×16 and 1024 channels. The fifth bottleneck 1807-5 receives the fourth downsampled feature representation 1808-4 and processes that input to produce a fifth downsampled feature representation 1808-5 that has spatial dimensions of 20×8 and 2048 channels.

As illustrated in the example process 1700 and the system 1800, extracted features 1810 are generated from the output downsampled feature representations, as in 1706. For example, continuing with the discussion of FIG. 18, the 256 channels of the second downsampled feature representation 1808-2 may be averaged 1809-2 across the 160×64 spatial dimensions to get second extracted features 1810-2 $F_2 \in 256 \times 1$. The 512 channels of the third downsampled feature representation 1808-3 may be averaged 1809-3 across the 80×32 spatial dimensions to get third extracted features 1810-3 $F_3 \in 512 \times 1$. The 1024 channels of the fourth downsampled feature representation 1808-4 may be averaged 1809-4 across the 40×16 spatial dimensions to get fourth extracted features 1810-4 $F_4 \in 1024 \times 1$. The 2048 channels of the fifth downsampled feature representation 1808-5 may be averaged 1809-5 across the 20×8 spatial dimensions to get fifth extracted features 1810-5 $F_5 \in 2048 \times 1$.

In addition to the extracted features 1810-2 through 1810-5 (i.e., $F_1$ through $F_5$) extracted from each downsampled output, a neural network output feature may also be generated based on an output of the neural network 1200. For example, block 1209-6, which corresponds to block 1209-5, may output an average of the fifth downsampled feature representation 1208-5. A linear function 1211 may be applied to the output to produce a 1000-channel feature 1808-6 $F_6$.

Returning to FIG. 17, if there are no additional bottlenecks to process, the example process 1700 utilizes a multi-scale representation which combines the extracted features from each of the downsampled inputs and concatenates them with the 1000-channel feature output from the neural network to produce concatenated features, as in 1712.

Referring again to FIG. 18, as features 1810-2 through 1810-5 are extracted or after all have been extracted, the features are concatenated. For example, $F_2$ 1810-2 is concatenated with $F_3$ 1810-3, which is concatenated with $F_4$ 1810-4, which is then concatenated with $F_5$ 1810-5, as illustrated by concatenation indicators 1814-2, 1814-3, 1814-4. The concatenation of features $F_1$ through $F_5$ is also concatenated with the feature F6 output from the neural network 1807, as indicated by concatenation indicators 1814-5 and 1814-6 to produce concatenated features 1810-7 $F_7 = [F_2, F_3, F_4, F_5, F_6] \in 4840 \times 1$.

A linear function may then be applied to the concatenated features to determine a body fat measurement representation, as in 1714 (FIG. 17). For example, as illustrated in FIG. 18, linear function 1813 may be applied to $F_7$ 1810-7 to produce a determined body fat measurement representation 1815 which, in this example is a 65×1 dimensional vector. For example, the determined body fat measurement representation ("V") 1815 may be determined as:

$$V = W \times F_7 + B \in 65 \times 1$$

where $W \in 65 \times 4840$ and $B \in 65$ are weights and bias of a linear function which my be implemented as a matrix product $W \times F_7$ and summed with the bias matrix B. The weights may be different for each feature $F_1$ through $F_5$ and may be applied as part of the extraction and averaging 1209, or as part of the vector representation of the body fat measurement representation. In other implementations, no weights may be applied.

As illustrated, the above determines a 65-dimensional measured body fat representation $V \in 65 \times 1$ in which each element $V_j$, $j \in \{0, \ldots 64\}$ denotes the probability of the body fat measurement being j. This body fat measurement representation 1815 may then be further processed to determine a body fat measurement value, as in 1716. For example, a probability weighted average of V, namely $\hat{V} = \Sigma_j j V_j$, may be determined and used as the body fat measurement value ("$\hat{V}$"). For example, if the neural network 1807 determines that the probability of the body fat measurement being 22 is 0.5, the probability of the body fat measurement being 23 is 0.5, and all other probabilities are 0:

$$\hat{V} = 22 \times 0.5 + 23 \times 0.5 = 22.5$$

Figure 19:
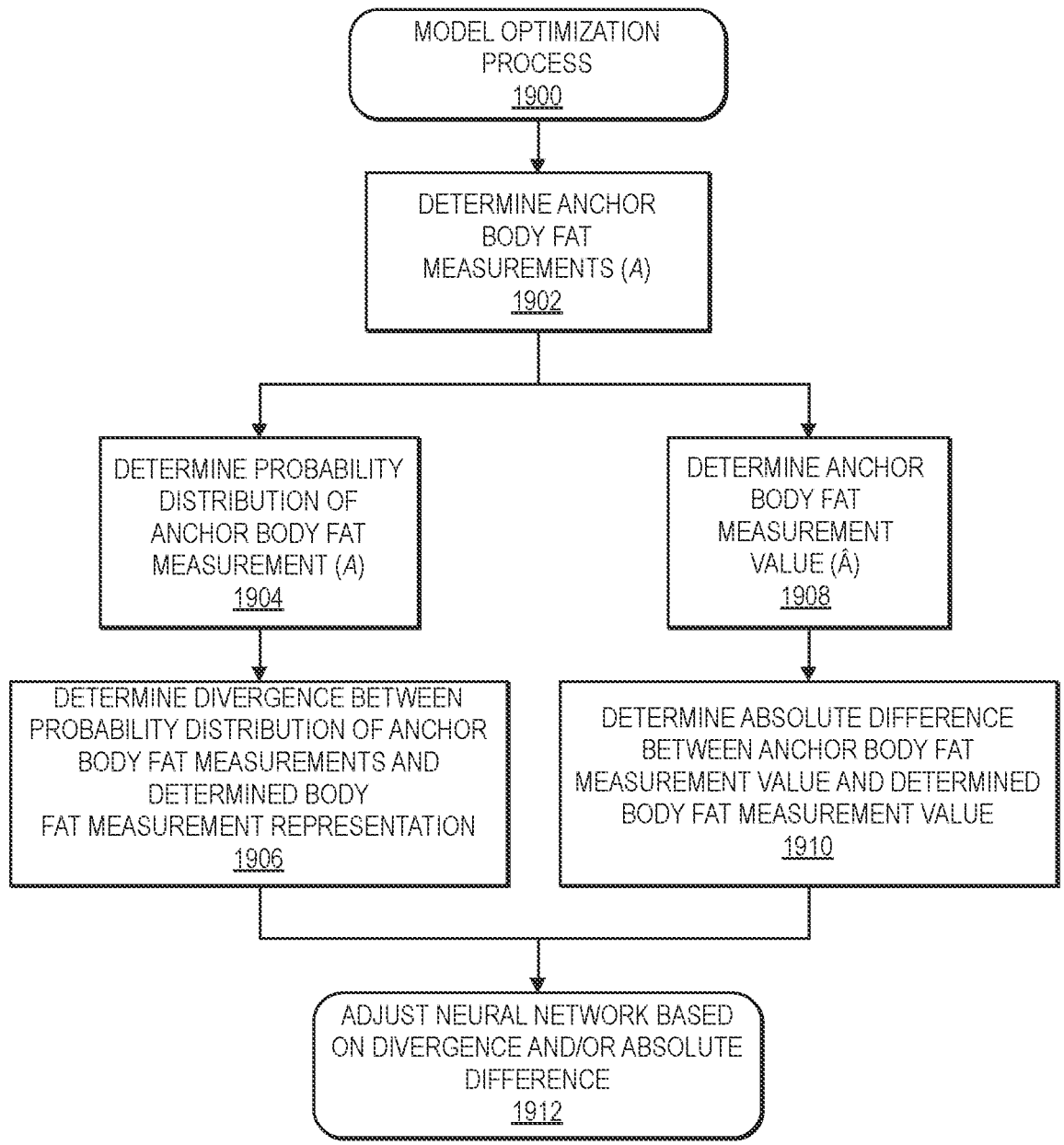
FIG. 19 is an example model optimization process, in accordance with implementations of the present disclosure.

FIG. 19 is an example model optimization process 1900, in accordance with implementations of the present disclosure. As discussed above, in some implementations the determined body fat measurement representation or the body fat measurement value may be compared to known or anchor body fat measurement representation or anchor body fat measurement values to determine loss functions and those loss functions may be provided back to the neural network to improve the accuracy of the neural network and the resultant body fat measurements.

The example process 1900 begins by determining anchor body fat measurements ("A"), as in 1902. The anchor body fat measurements may be vector based body fat measurements representations and/or body fat measurements values. The anchor body fat measurements may be obtained from human annotators that are trained to determine body fat measurements for bodies represented in images, obtained from other systems that measure body fat of a body (e.g., DEXA, ADP), and/or obtained from other sources. In some implementations, the anchor body fat measurements may be an average of multiple body fat measurements of a body obtained from different sources. For example, if there are N human annotators that have determined the body fat of a particular body to be $a_1, a_2, a_3 \ldots a_N$ an anchor body fat measurement may be determined for the body as an average of those determination $$\hat{A} = \frac{1}{N} \Sigma_n a_n.$$

Likewise, to determine an anchor probability distribution, a probability distribution may be determined based on the body fat measurements provided by the annotators themselves. For example, if four annotators determine the body fat measurement of the body to be 20, 21, 21, 22, the probability distribution may be determined to be $A_{20}=0.25$, $A_{21}=0.5$, $A_{22}=0.25$, and $A_n=0$, $\forall n \notin \{20, 21, 22\}$. As another example, the body fat measurements may be fit to a Gaussian probability distribution that is centered about the average body fat measurement and decays as it moves away from the average. The peak location and the rate of decay may be controlled by varying the mean and sigma parameters μ, σ.

Returning to FIG. 19, in this example, two loss functions, a KL-Divergence and a Smooth L1 loss may be computed. Computation may be done in parallel, as illustrated, or in series. Likewise, in other implementations fewer, additional, and/or different loss functions may be computed and used to update the parameters of the neural networks to improve the operation thereof and continue to increase the accuracy of the resultant visual body fat measurements.

For the KL-Divergence, a probability distribution of the anchor body fat measurements is determined, as in 1904. The probability distribution of the anchor body fat measurements may be determined as discussed above.

A divergence between the probability distribution of the anchor body fat measurement and the determined body fat measurement representation is then determined, as in 1906. As discussed above, the determined body fat measurement representation may be a 65-dimensional vector that represents the probability distribution of the body fat measurement determined in accordance with the above disclosed implementations.

An anchor body fat measurement value ("A") may also be determined for the anchor body fat measurements, as in 1908. As discussed above, the body fat measurement value may be an average of the body fat measurements for the body received from different sources. The smooth L1 loss, also known as a Huber Loss, is an unsigned difference between the anchor body fat measurement value (A) and the determined body fat measurement value ($\hat{V}$), or $|\hat{V}-\hat{A}|$, as in 1910.

Finally, the neural network may be adjusted based on the computed loss functions, in this example the divergence and the absolute difference, as in 1912.

In addition to generating personalized 3D body models of a body and/or determining body fat of the body, as discussed above, in some implementations, predicted personalized 3D body models may be determined and presented that represent the predicted appearance of the body with different body measurement values. For example, if a user desires to see how their body will look if the user lowers their body from a current body fat measurement value to a target body fat measurement value, the disclosed implementations may determine predicted personalized 3D body parameters of the body of the user with a different body fat percentage and generate, based on those predicted personalized 3D body parameters a predicted personalized 3D body model representative of a predicted appearance of the body of the user with the target body fat measurement value. Likewise, in some implementations, multiple predicted personalized 3D body models may be generated for a body and a user my interact with the personalized 3D body models to view different predicted personalized 3D body models with different body measurements.

Figure 20:
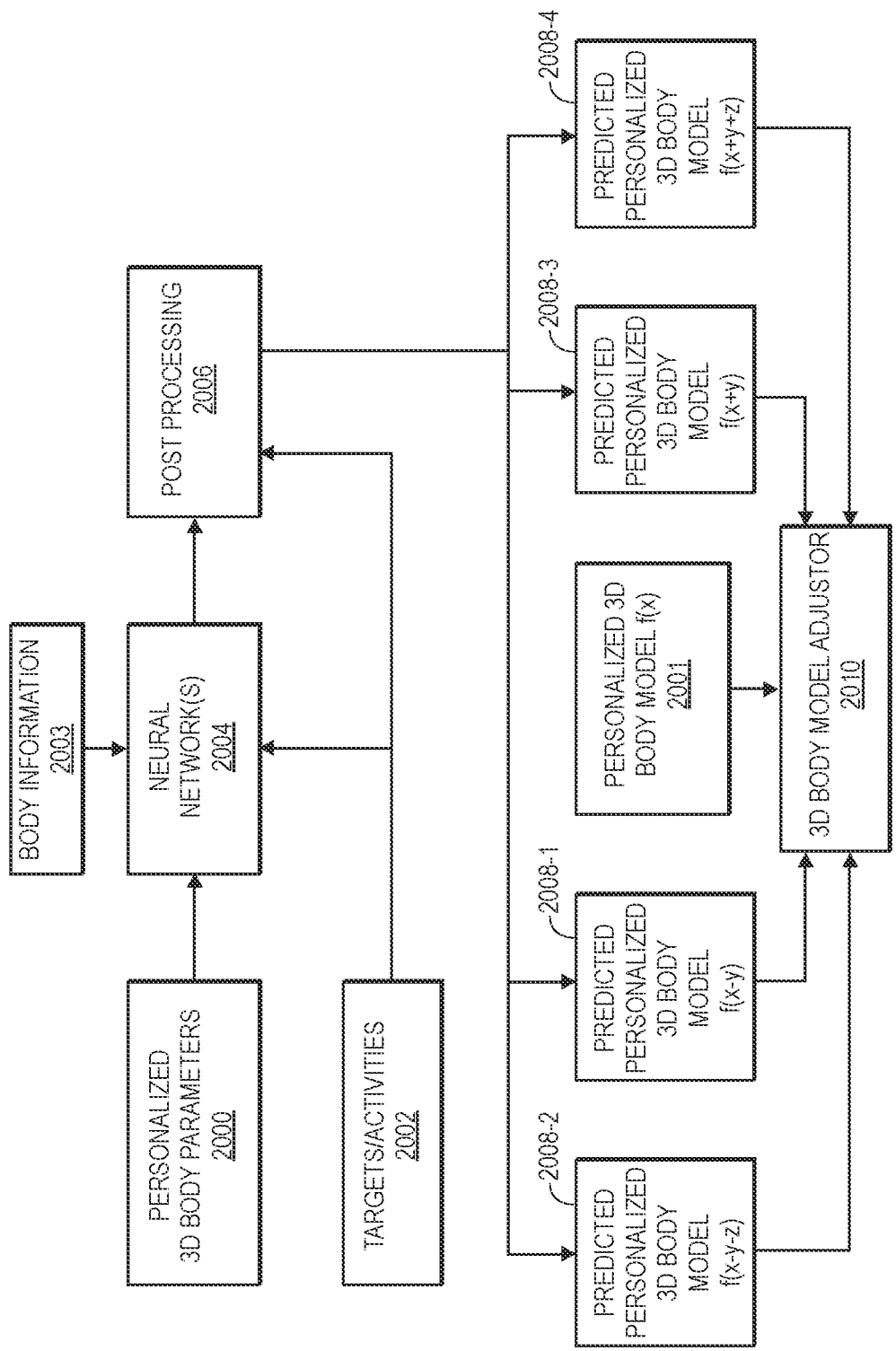
FIG. 20 is an example transition diagram of the generation of predicted three-dimensional body models, in accordance with implementations of the present disclosure.

FIG. 20 is an example transition diagram of the generation of predicted personalized 3D body models, in accordance with implementations of the present disclosure. As illustrated, different predicted personalized 3D body models 2008 may be generated based on personalized 3D body parameters 2000 and/or other body information 2003 about a body so that the generated predicted personalized 3D body models are representative of the actual body under consideration. For example, personalized 3D body parameters 2000, determined as discussed above, may be provided to a neural network 2004 with or without other body information 2003 about the body. Other body information may include, but is not limited to, height, weight, age, gender, ethnicity, body type, etc.

In addition to the personalized 3D body parameters 2000 and optionally other body information 2003, target body measurements and/or target activities 2002 may be provided to the neural network 2004 and used by the neural network to produce one or more predicted personalized 3D body models. Target body measurements may be one or more of any adjustable body measurement of a body, such as body fat, muscle mass, body weight, etc. Activities may be any activities that the user desires to perform to adjust one or more body measurements. For example, activities may include, but are not limited to, exercising X number of minutes, Y days per week, limiting calorie intake to Z calories per day, sleeping ZZ hours per day, etc.

The disclosed implementations may consider activity targets and other information about the body to determine potential changes in one or more body measurement values over time and utilize that information to generate predicted personalized 3D body models. For example, if a user provides a target of exercising 30 minutes per day, six days per week, the disclosed implementations may determine, assuming all other factors (e.g., food intake, rest, etc.) remain unchanged, the predicted change in the body fat measurement and/or muscle mass of the body of the user and utilize that information to generate predicted personalized 3D body models 2008.

In some implementations, the neural network may also consider historical information about the body to determine different predicted personalized 3D body parameters that correspond to the target body measurement values. For example, if historical information, such as a series of target body measurements and/or personalized 3D body parameters over a period of time have been maintained for the body, the disclosed implementations may compare different personalized 3D body parameters for those different measurements to determine the rate or amount of change that occurs for different portions of the body. For example, if a body of a user loses weight first in their face and torso area, that information may be determined from historical 3D body parameters for the body and the rate of change for those different portions of the body may be used to generate predicted personalized 3D body parameters based on a target body measurement.

Likewise, different body model parameters may be applied based on the target changes or target activities, such as walking compared to weightlifting to represent different predicted personalized 3D body models having different appearances. For example, if a user specifies a target body fat percentage that is 10% lower than their current body fat percentage and an activity change of walking X miles per day, Y days per week, the disclosed implementations may utilize a first neural network to generate a predicted personalized 3D body model with fat and muscle changes that correspond to the target body fat that are likely based on the specified activity of walking. In comparison, if the user specifies a target body fat percentage that is 10% lower than their current body fat percentage and an activity change of lifting weights X minutes per day, Y days per week, the disclosed implementations may utilize a second neural network to generate a predicted personalized 3D body model with fat and muscle changes that correspond to the target body fat that are likely based on the specified activity of lifting weights.

Referring back to FIG. 20, and as discussed further below, the predicted personalized 3D body parameters generated by the neural network 2004 based on the personalized 3D body parameters and the target body measurements and/or activities may be further processed using post processing 2006 to further adapt the generated predicted personalized 3D body models to the personalized 3D body model 2001. For example, shading, contours, clothing patterns, skin color, etc., of the personalized 3D body model 2001 may be adjusted and applied to the predicted personalized 3D body models as part of the post processing 2006 to further adjust the predicted personalized 3D body models to the appearance of the body represented in the personalized 3D body model 2001.

As will be appreciated, in some implementations, multiple predicted personalized 3D body models may be determined using the disclosed implementations and a 3D body model adjustor 2010 may be presented to the user to allow the user to interact with and view the different predicted personalized 3D body models. In the example illustrated in FIG. 20, four predicted personalized 3D body models 2008-1, 2008-2, 2008-3, and 2008-4 are generated that correspond to the personalized 3D body model 2001. The different predicted personalized 3D body models 2008 illustrate the body represented by the personalized 3D body model 2001 having different body measurement values. For example, if the personalized 3D body model 2001 has body measurements represented by $f(x)$, a first predicted personalized 3D body model 2008-1 may represent the body with a first lower body fat measurement, represented as $f(x-y)$ and a second predicted personalized 3D body model 2008-2 may represent the body with a second lower body fat measurement that is lower than the first body fat measurement, represented as $f(x-y-z)$. Similarly, the disclosed implementations may also generate predicted personalized 3D body models representative of the body at higher body measurements. For example, predicted personalized 3D body model 2008-3 may represent the body with a first higher body fat measurement, represented as $f(x+y)$ and a second predicted personalized 3D body model 2008-4 may represent the body with a second higher body fat measurement that is higher than the first body fat measurement, represented as $f(x+y+z)$. As a specific example, if the personalized 3D body model has a 27% body fat measurement value, the first predicted personalized 3D body model 2008-1 may correspond to a 22% body fat measurement value, the second predicted personalized 3D body model 2008-2 may correspond to a 17% body fat measurement value, the third predicted personalized 3D body model may correspond to a 32% body fat measurement value, and the fourth predicted personalized 3D body model may correspond to a 37% body fat measurement value.

As will be appreciated, any range of body measurement values may be selected and used to generate predicted body models and any number of predicted body models may be generated using the disclosed implementations. Likewise, while the disclosed implementations primarily discuss changes in body fat value measurements, other adjustable body measurements, such as muscle mass may likewise be predicted and illustrated with the disclosed implementations.

In still further implementations, one or more predicted personalized 3D body models and the personalized 3D body model may be integrated to produce multiple predicted personalized 3D body models between each generated predicted personalized 3D body model such that a user can visualize a continuous change to the appearance of the body between the different body measurement values. For example, the personalized 3D body model 2001 may be integrated with each of the four predicted personalized 3D body models 2008-1, 2008-2, 2008-3, and 2008-4 to produce any number of intervening predicted personalized 3D body models that may rendered and presented as a user interacts with the 3D body model adjustor 2010 to illustrate the predicted appearance of the body between any of the different predicted personalized 3D body models.

Figure 21:
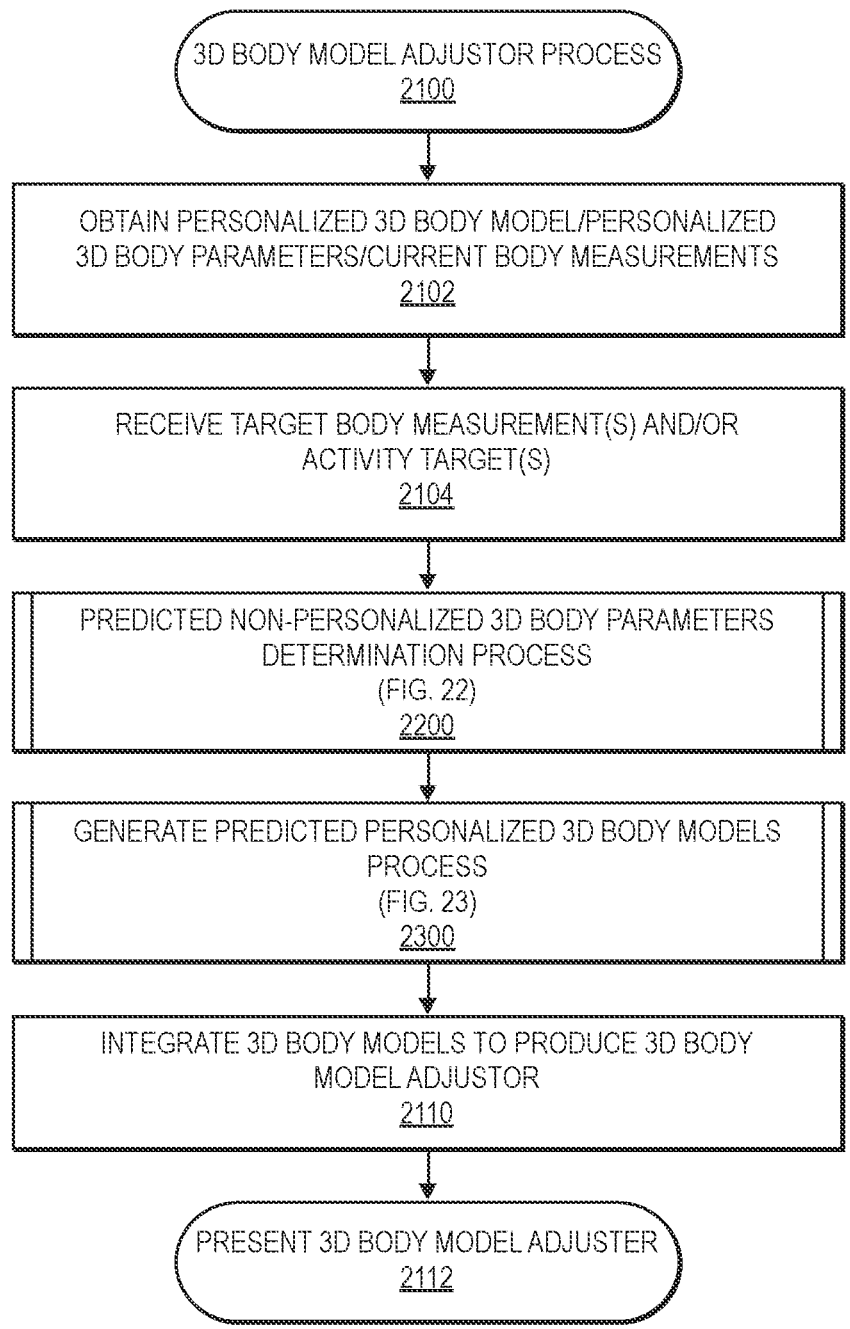
FIG. 21 is an example three-dimensional personalized 3D process, in accordance with implementations of the present disclosure.

FIG. 21 is an example 3D body model adjustor process 2100, in accordance with implementations of the present disclosure. The example process 2100 begins by obtaining a personalized 3D body model of a body, personalized 3D body parameters of that body, and current body measurements, as in 2102. For example, the personalized 3D body model, personalized 3D body parameters, and/or the current body measurements, may be obtained from any of the above described implementations. Alternatively, or in addition thereto, one or more of the personalized 3D body parameters and/or the current body measurements may be obtained from other sources, such as from a user, a third party, etc.

The example process 2100 also receives one or more target body measurements, such as a target change in body fat measurement value or a target change in muscle mass measurement value and optionally one or more target activities, as in 2104. A target activity, as discussed above, may be any activity (e.g., walking, running, lifting weights, swimming, skiing, etc.) or change in behavior (change in calorie intake, change in sleep, etc.) specified by a user that will result in a change in one or more body measurement values.

Based on current body measurements, body information, and target body measurements and/or activity targets, non-personalized 3D body parameters and one or more predicted non-personalized 3D body parameters are determined by the predicted non-personalized 3D body parameters determination process, as in 2200. The predicted non-personalized 3D body parameters determination process 2200 is discussed in further detail below with respect to FIG. 22. As discussed below, the output from the predicted non-personalized 3D body parameters determination process 2200 is one or more sets of predicted non-personalized 3D body parameters generated by a trained neural network based on the target body measurements, body information, and any activity goals received by the example process 2100 at blocks 2102 and 2104.

Utilizing the predicted non-personalized 3D body parameters, one or more predicted personalized 3D body models are generated by the generate predicted personalized 3D body models process, as in 2300. The generate predicted personalized 3D body models process 2300 is discussed in further detail below with respect to FIG. 23. As discussed below, the output from the generate predicted personalized 3D body model process 2300 is one or more predicted personalized 3D body models corresponding to the personalized 3D body model received in block 2102.

The example process 2100 may then integrate the returned predicted personalized 3D body models and the personalized 3D body model to produce a 3D body model adjustor that may be viewed and interacted with by a user to view predicted appearances of the body at different body measurements, as in 2110. For example, the personalized 3D body model and a first predicted personalized 3D body model may be integrated by averaging the two models to determine body parameters for intermediate personalized 3D body models between the personalized 3D body model and the predicted personalized 3D body model.

Finally, the 3D body model adjustor is presented to a user so that the user can interact with the 3D body model adjustor and view the predicted appearance changes to the body based on different activities and/or based on different body measurements, as in 2112.

Figure 22:
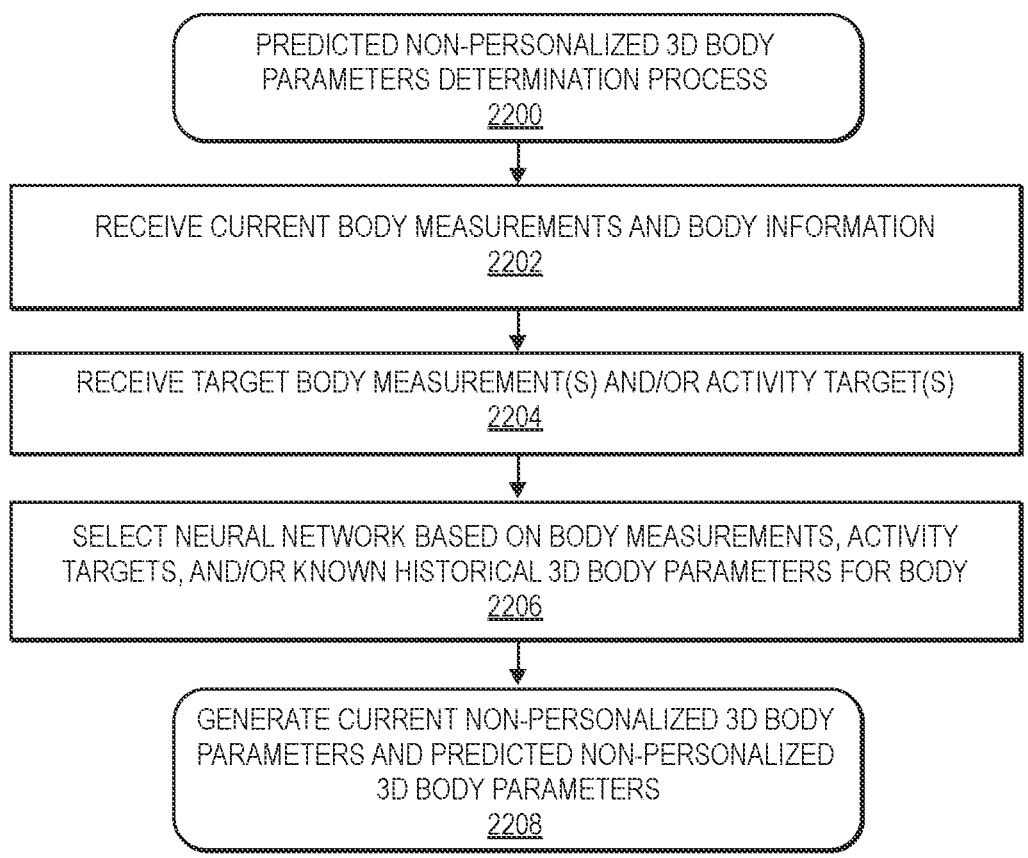
FIG. 22 is an example predicted non-personalized three-dimensional body parameters determination process, in accordance with implementations of the present disclosure.

FIG. 22 is an example predicted non-personalized 3D body parameters determination process 2200, in accordance with implementations of the present disclosure. The example process 2200 begins upon receipt of current body measurements (e.g., weight, body fat measurement value, muscle mass measurement value, etc.) and body information (e.g., age, gender, ethnicity, height, body type, etc.), as in 2202. In addition, one or more target body measurements and/or activity targets are received, as in 2204. For example, a user may provide a target change in body fat, muscle mass, body weight, etc. Alternatively, or in addition thereto, a user may specify one or more changes in activities and/or behavior that will affect one or more body measurements. In addition, the example process may also determine if there is any historical 3D body parameters maintained in a memory.

For example, if the body has been scanned by the disclosed implementations periodically over a period of time and personalized 3D body parameters determined for the body at each of those points in time, changes in body measurements and the corresponding changes in the personalized 3D body parameters may be utilized to determine how the body will likely respond to additional body measurement changes. For example, it may be determined from historical personalized 3D body parameters that when the body loses or gains body fat, on average, 30% of that gain/loss occurs in the legs of the body, 55% of that gain/loss occurs in the torso of the body, 10% of that gain/loss occurs in the arms of the body, and 5% of that gain/loss occurs in the head and neck of the body.

The example process 2200 may then select one or more neural networks based on one or more of the body information, body measurements, and/or stored historical 3D body parameters for the body, as in 2206.

As discussed, multiple different neural networks may be trained to produce predicted non-personalized 3D body parameters based on different body types, ages, gender, ethnicity, etc., because different bodies may respond differently to difference changes in body measurements. For example, older men may lose body fat first in their face and neck compared to younger women who may lose body fat first in their legs and arms. In addition, bodies respond differently to different activity types. For example, if a target is to decrease body fat measurement values and an activity type is lifting weights, the body may respond by increasing muscle mass and losing a first amount of body weight thereby resulting in a first body composition that has more muscle mass and a lower body fat measurement values. Comparatively, if the same body has the same target change in body fat measurement value but an activity target of altering calorie intake and walking, the body will respond by losing more body fat but not gaining as much muscle mass, compared to the prior example. As a result, the predicted personalized 3D body models will appear different, because one will have a larger gain in muscle mass, even though the body fat percentage measurement will be the same.

In some implementations, the selected neural network may also be adjusted based on body measurements, body information, activity targets, and/or historical personalized 3D body parameters known for the body.

After selecting and/or adjusting the neural network, non-personalized 3D body parameters and one or more sets of predicted non-personalized 3D body parameters are determined by the neural network, as in 2208. In some implementations, a single set of predicted 3D body parameters may be determined for the target body measurements and/or the target activities. In other implementations, multiple sets of predicted non-personalized 3D body parameters may be determined for the body. Predicted non-personalized 3D body parameters are generated by the neural network based on body information about the body and based on the trained data of the neural network that correspond to the size, shape, ethnicity, gender, historical information, etc., of the body. As discussed further below, while the non-personalized 3D body parameters and predicted non-personalized 3D body parameters correspond to the body, they may not be directly representative of the body. As such, as discussed further below, the non-personalized 3D body parameters and predicted non-personalized 3D body parameters may be further processed to generate predicted personalized 3D body parameters that are directly correlated to the body to be represented by the predicted personalized 3D body models.

Figure 23A:
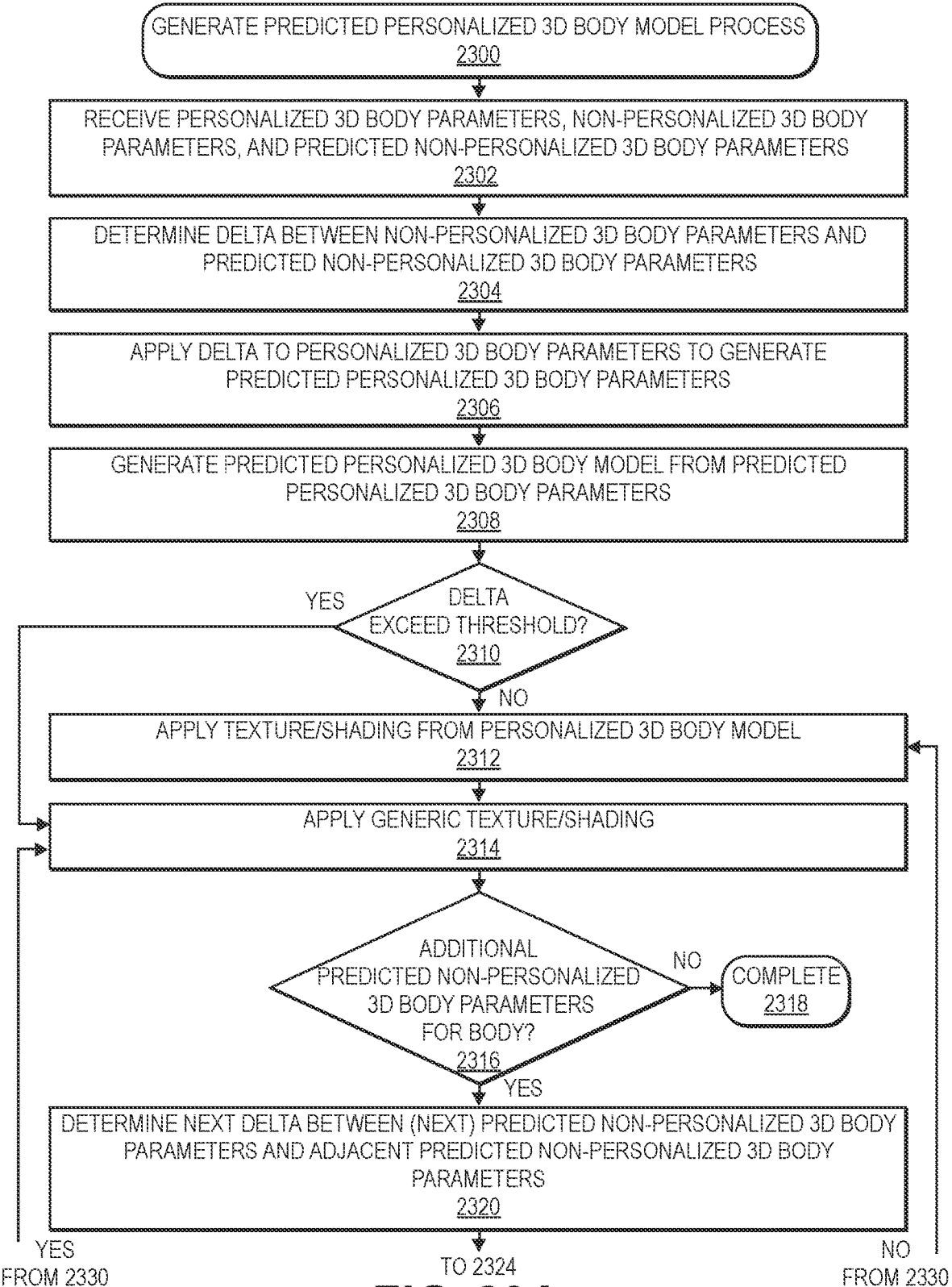
FIGS. 23A through 23B is an example generate predicted three-dimensional body model process, in accordance with implementations of the present disclosure.
Figure 23B:
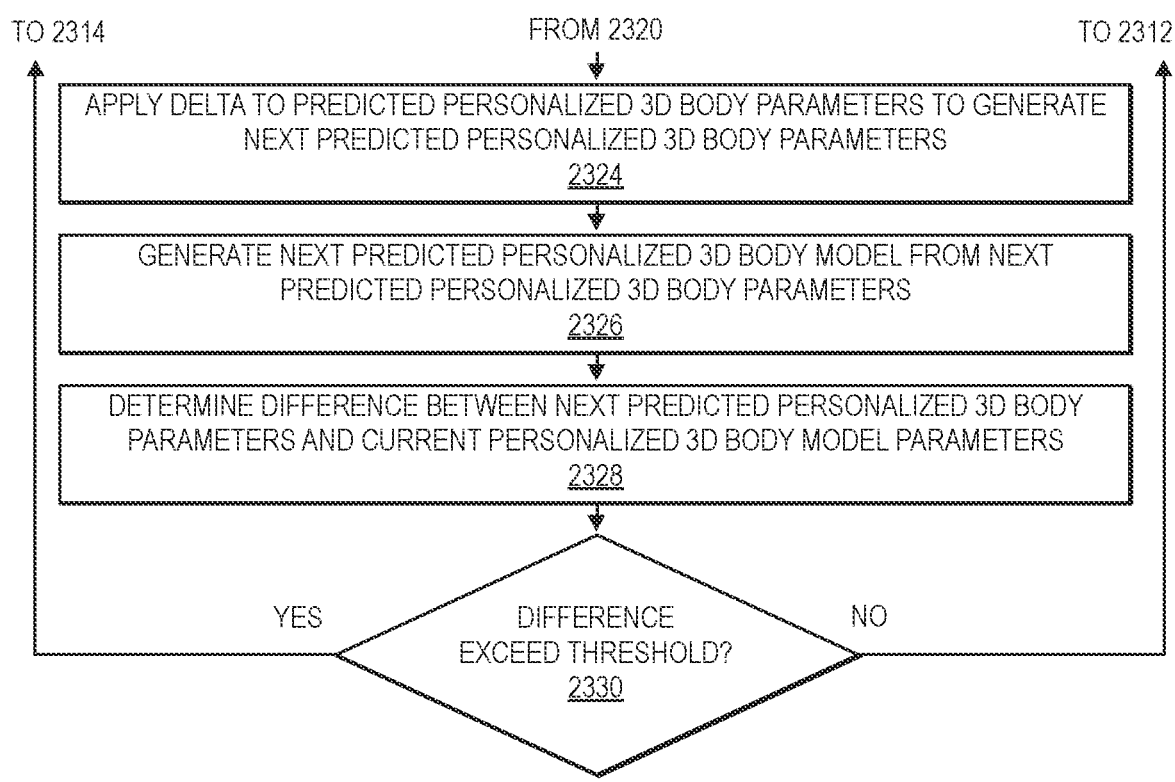

FIGS. 23A through 23B is an example generate predicted personalized 3D body model process 2300, in accordance with implementations of the present disclosure. The example process 2300 begins by receiving a personalized 3D body parameters (FIG. 10), non-personalized 3D body parameters (FIG. 22), and predicted non-personalized 3D body parameters (FIG. 22), as in 2302.

A delta or difference is then determined between the non-personalized 3D body parameters and the predicted non-personalized 3D body parameters, as in 2304. Those deltas are then applied to the personalized 3D body parameters to produce predicted personalized 3D parameters that illustrate the predicted change from a current state of the body to the target or predicted state of the body, based on the personalized 3D body parameters, as in 2306.

Utilizing the predicted personalized 3D body parameters, a predicted personalized 3D body model representative of a predicted appearance of the body at the target or predicted state of the body is generated, as in 2308. The predicted personalized 3D body parameters may be used to generate a predicted personalized 3D body model as if the predicted personalized 3D body parameters were personalized 3D body parameters.

A determination is then made as to whether the delta or change exceeds a threshold, as in 2310. The threshold may be any defined amount or value and may vary for different bodies, different ranges of body measurement values, different body types, etc.

If it is determined that the delta does not exceed the threshold, texture (e.g., clothing, skin color, hair color) and shading (e.g., body contours, shadows) from the personalized 3D body model are modified according to the changes in the personalized 3D body parameters and applied to the predicted personalized 3D body model, as in 2312. In addition to applying texture and shading from the personalized 3D body model to the predicted personalized 3D body model, or if it is determined that the delta exceeds the threshold, one or more generic texture and/or shading may be applied to the predicted personalized 3D body model, as in 2314. Generic texture may include generic clothing that may be applied when the delta exceeds the threshold. Generic shading may be shadings applied to different body types to aid in the illustration of muscle definition at different body fat or muscle mass measurement values.

After generating a first predicted personalized 3D body model, a determination is made as to whether additional predicted non-personalized 3D body parameters remain for which a predicted personalized 3D body model is to be generated, as in 2316. If no predicted non-personalized 3D body parameters remain, the example process 2300 completes, as in 2318. However, if there are additional predicted non-personalized 3D body parameters for which predicted personalized 3D body models are to be generated, the example process 2300 determines a next delta between a next predicted non-personalized 3D body parameters and an adjacent predicted non-personalized 3D body parameters, as in 2320. Adjacent predicted non-personalized 3D body parameters may be any set of predicted non-personalized 3D body parameters. For example, if the first predicted non-personalized 3D body parameters corresponds to a body with 20% body fat, an adjacent set of predicted non-personalized body parameters may be the next set that corresponds to the body at a 15% body fat.

Referring now to FIG. 23B, the next delta is then applied to the predicted personalized 3D body parameters to generate next predicted personalized 3D body parameters, as in 2324. As above, the next predicted personalized 3D body parameters may then be used to generate a next predicted personalized 3D body model, as in 2326.

A difference between the next predicted personalized 3D body parameters and the personalized 3D body parameters may also be determined, as in 2328, and a determination made as to whether that difference exceeds the threshold, as in 2330. The threshold discussed in 2330 and in 2310 may be the same or a different threshold. For example, texture and shading from the personalized 3D body model may be applied to predicted personalized 3D body models provided the differences between the personalized 3D body model and the predicted personalized 3D body model do not exceed 10%. By determining, for each generated predicted personalized 3D body model, a difference between that predicted personalized 3D body model and the personalized 3D body model, the same threshold may be used to determine whether to transform and apply texture and/or shading from the personalized 3D body model or only apply generic texture and/or shading. If it is determined that the difference exceeds the threshold, the example process 2300 returns to block 2314 and continues. In comparison, if it is determined that the difference does not exceed the threshold, the example process 2300 returns to block 2312 and continues.

Figure 24:
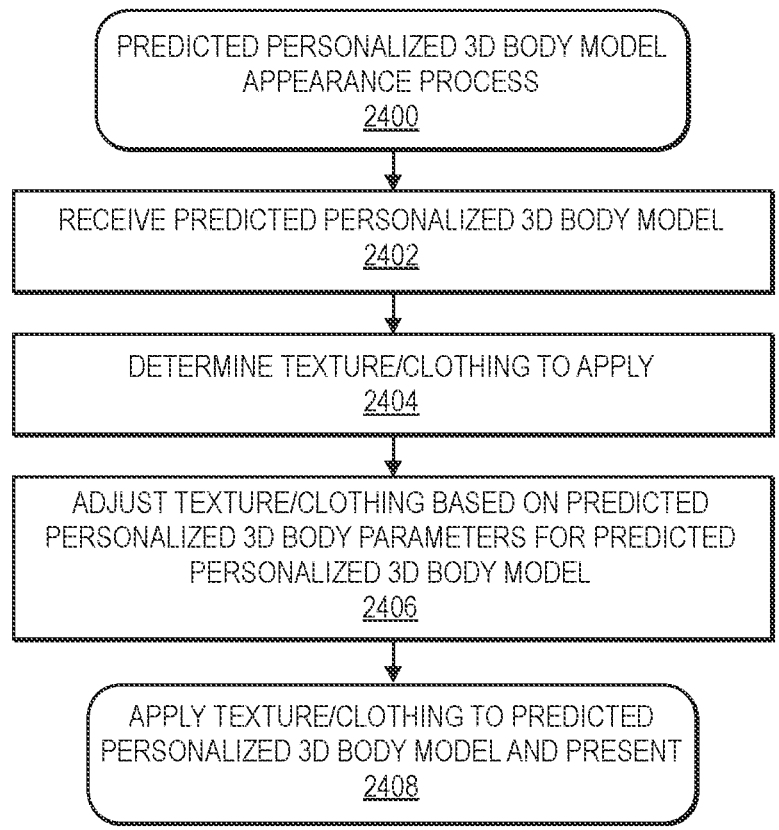
FIG. 24 is an example predicted three-dimensional body model appearance process, in accordance with implementations of the present disclosure.

FIG. 24 is an example predicted by model appearance process 2400, in accordance with implementations of the present disclosure. The example process 2400 may be used to simulate how a body or a predicted body may look in different clothing or outfits.

The example process 2400 begins by receiving a personalized 3D body model or predicted personalized 3D body model of a body, as in 2402. The example process may then determine a texture and/or clothing to apply to the personalized 3D body model or predicted personalized 3D body model, as in 2404. For example, a user may specify that they want to see how the body will look in a wedding dress, a bathing suit, a suit, shorts, etc., when the body has different body measurements (e.g., higher/lower body fat).

The determined clothing/texture is then adjusted to correspond to the personalized 3D body parameters and/or predicted personalized 3D body parameters corresponding to the personalized 3D body model or predicted personalized 3D body model so that the clothing/texture conforms to the shape of the respective personalized 3D body model, as in 2406.

Finally, the texture/clothing is applied to the personalized 3D body model and/or predicted personalized 3D body model and presented to a user so that the user can view the clothing/texture on the body at different body measurements, as in 2408. In some implementations, the personalized 3D body model with the applied clothing/texture and one or more predicted personalized 3D body models with the applied clothing/texture may be integrated, as discussed above and a 3D body model adjustor generated that allows the user to view the body at each different body measurement with the applied clothing/texture.

Figure 25:
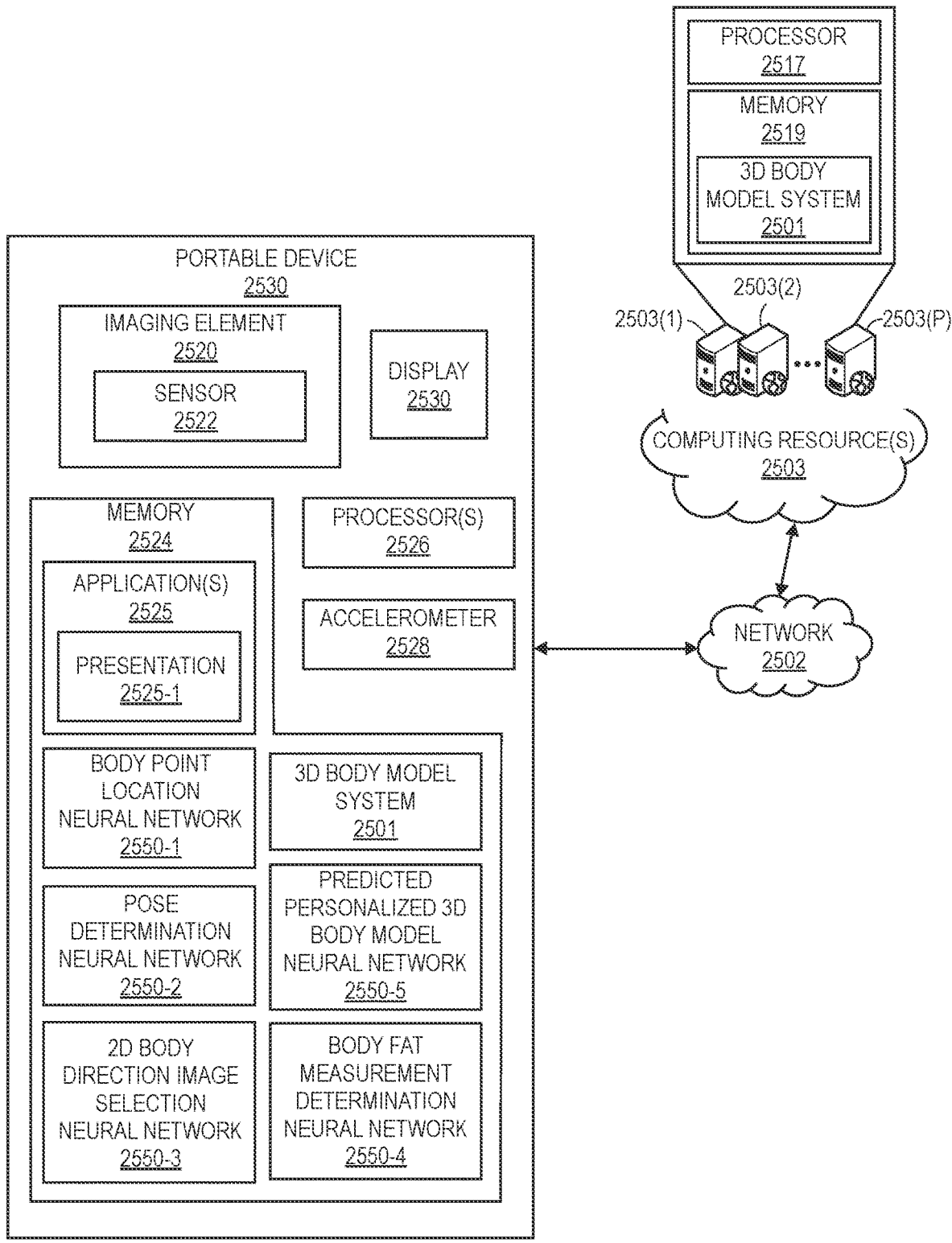
FIG. 25 is a block diagram of example components of a portable device and remote computing resources, in accordance with implementations of the present disclosure.

FIG. 25 is a block diagram of example components of a portable device 2530 and remote computing resources 2503, in accordance with implementations of the present disclosure. In some implementations, the portable device 2530 may correspond to the portable device 930 of FIG. 9 and/or the computing resources 2503 or the 3D body model system 2501 may correspond to the body composition system 910 of FIG. 9.

As illustrated, the portable device may be any portable device 2530 such as a tablet, cellular phone, laptop, wearable, etc. The imaging element 2520 of the portable device 2530 may comprise any form of optical recording sensor 2522 or device that may be used to photograph or otherwise record information or data regarding a body of the user, or for any other purpose. As is shown in FIG. 25, the portable device 2530 is connected to the network 2502 and includes one or more memory 2524 or storage components (e.g., a database or another data store), one or more processors 2526, an accelerometer 2528 or other position/orientation/angle determining component, an output, such as a display 2530, speaker, haptic output, etc., and any other components that may be required in order to capture, analyze and/or store and/or transmit imaging data, such as the 2D body images discussed herein and/or to receive personalized 3D body parameters and/or body measurements and to render and present a personalized 3D body model. For example, the imaging element 2520 may capture one or more still or moving images. The portable device 2530 may also connect to or otherwise communicate with the network 2502 through the sending and receiving of digital data.

The portable device 2530 may be used in any location and any environment to generate 2D body images that represent a body of the user. In some implementations, the portable device may be positioned such that it is stationary and approximately vertical (within approximately ten-degrees of vertical) and the user may position their body within a field of view of the imaging element 2520 of the portable device at different directions so that the imaging element 2520 of the portable device may generate 2D body images that include a representation of the body of the user from different directions, also referred to herein as 2D body direction images.

The portable device 2530 may also include one or more applications 2525, such as presentation application 2525-1, stored in memory that may be executed by the one or more processors 2526 of the portable device to cause the processor of the portable device to perform various functions or actions. For example, when executed, the application 2525 may provide instructions to a user regarding placement of the portable device, positioning of the body of the user within the field of view of the imaging element 2520 of the portable device, pose of the body, direction of the body, etc. Likewise, in some implementations, the presentation application 2525-1 may present a personalized 3D body model, generated from the 2D body images in accordance with the described implementations, to the user and allow the user to interact with the personalized 3D body model. For example, a user may rotate the personalized 3D body model to view different angles of the personalized 3D body model, obtain approximately accurate measurements of the body of the user from the dimensions of the personalized 3D body model, view body measurements, such as body fat, body mass, volume, etc.

The application may also include or communicate with one or more neural networks, such as a body point location neural network 2550-1, pose determination neural network 2550-2, a 2D body direction image selection neural network 2550-3, a body fat measurement determination neural network 2550-4, and/or a predicted personalized 3D body model neural network 2550-5 that are maintained in the memory 2524 of the portable device 2530 and executed by the one or more processors 2526 of the portable device 2530. As discussed above, the body point location neural network may receive one or more 2D body image from the imaging element 2520, process those images and generate, for each received image, a heat map indicating predicted body point locations. The pose determination neural network 2550-2 may receive as inputs the heat map produced by the body point location neural network 2550-1 and further process that heat map to determine whether the body represented in the 2D body image is in a defined pose, such as an A Pose. The 2D body direction image selection neural network 2550-3 may also receive the heat map and/or the 2D body images and further process that information to determine body direction confidence scores for a plurality of 2D body images and to select a 2D body image as the 2D body direction image for a determined body direction. The body fat measurement determination neural network 1550-4 may receive one or more 2D body images and/or one or more normalized body images and process those images to determine a body fat measurement value representation illustrative of the body fat of the body represented in the image(s). The predicted personalized 3D body model neural network 2550-5 may receive one or more adjustments to body measurements and/or activity levels, generally targets, and generate predicted personalized 3D body parameters corresponding to those targets and/or generate predicted personalized 3D body models corresponding to those targets that are representative of the predicted body appearance based on those targets.

Machine learning tools, such as artificial neural networks, have been utilized to identify relations between respective elements of apparently unrelated sets of data. An artificial neural network, such as CNN, is a parallel distributed computing processor comprised of individual units that may collectively learn and store experimental knowledge, and make such knowledge available for use in one or more applications. Such a network may simulate the non-linear mental performance of the many neurons of the human brain in multiple layers by acquiring knowledge from an environment through one or more flexible learning processes, determining the strengths of the respective connections between such neurons, and utilizing such strengths when storing acquired knowledge. Like the human brain, an artificial neural network may use any number of neurons in any number of layers, including an input layer, an output layer, and one or more intervening hidden layers. In view of their versatility, and their inherent mimicking of the human brain, machine learning tools including not only artificial neural networks but also nearest neighbor methods or analyses, factorization methods or techniques, K-means clustering analyses or techniques, similarity measures such as log likelihood similarities or cosine similarities, latent Dirichlet allocations or other topic models, or latent semantic analyses have been utilized in image processing applications.

Artificial neural networks may be trained to map inputted data to desired outputs by adjusting the strengths of the connections between one or more neurons, which are sometimes called synaptic weights. An artificial neural network may have any number of layers, including an input layer, an output layer, and any number of intervening hidden layers. Each of the neurons in a layer within a neural network may receive one or more inputs and generate one or more outputs in accordance with an activation or energy function, with parameters corresponding to the various strengths or synaptic weights. Likewise, each of the neurons within a network may be understood to have different activation or energy functions; in this regard, such a network may be dubbed a heterogeneous neural network. In some neural networks, at least one of the activation or energy functions may take the form of a sigmoid function, wherein an output thereof may have a range of zero to one or 0 to 1. In other neural networks, at least one of the activation or energy functions may take the form of a hyperbolic tangent function, wherein an output thereof may have a range of negative one to positive one, or −1 to +1. Thus, the training of a neural network according to an identity function results in the redefinition or adjustment of the strengths or weights of such connections between neurons in the various layers of the neural network, in order to provide an output that most closely approximates or associates with the input to the maximum practicable extent.

Artificial neural networks may typically be characterized as either feedforward neural networks or recurrent neural networks, and may be fully or partially connected. In a feedforward neural network, e.g., a CNN, information specifically flows in one direction from an input layer to an output layer, while in a recurrent neural network, at least one feedback loop returns information regarding the difference between the actual output and the targeted output for training purposes. Additionally, in a fully connected neural network architecture, each of the neurons in one of the layers is connected to all of the neurons in a subsequent layer. By contrast, in a sparsely connected neural network architecture, the number of activations of each of the neurons is limited, such as by a sparsity parameter.

Moreover, the training of a neural network is typically characterized as supervised or unsupervised. In supervised learning, a training set comprises at least one input and at least one target output for the input. Thus, the neural network is trained to identify the target output, to within an acceptable level of error. In unsupervised learning of an identity function, such as that which is typically performed by a sparse autoencoder, target output of the training set is the input, and the neural network is trained to recognize the input as such. Sparse autoencoders employ backpropagation in order to train the autoencoders to recognize an approximation of an identity function for an input, or to otherwise approximate the input. Such backpropagation algorithms may operate according to methods of steepest descent, conjugate gradient methods, or other like methods or techniques, in accordance with the systems and methods of the present disclosure. Those of ordinary skill in the pertinent art would recognize that any algorithm or method may be used to train one or more layers of a neural network. Likewise, any algorithm or method may be used to determine and minimize the error in an output of such a network. Additionally, those of ordinary skill in the pertinent art would further recognize that the various layers of a neural network may be trained collectively, such as in a sparse autoencoder, or individually, such that each output from one hidden layer of the neural network acts as an input to a subsequent hidden layer.

Once a neural network has been trained to recognize dominant characteristics of an input of a training set, e.g., to associate an image with a label, a category, a cluster or a pseudolabel thereof, to within an acceptable tolerance, an input and/or multiple inputs, in the form of an image, features, known traits corresponding to the image, etc., may be provided to the trained network, and an output generated therefrom. For example, one of the neural network discussed above may receive as inputs a 2D body direction image. The trained neural network may then produce as outputs the probability that the body is a particular body direction. As another example, one of the neural network discussed above may receive as inputs the 2D body direction image and generate as outputs a heat map indicating for each x, y coordinate of the heat map a probability that the coordinate corresponds to a body point of the body represented in the 2D body direction image.

Returning to FIG. 25, the application 2525, upon selection of a 2D body direction image by the 2D body direction image selection neural network 2550-3 may send, via the network 2502, the selected 2D body direction image to the computing resources 2503 for processing by the 3D body model system 2501.

Generally, the 3D body model system 2501 includes computing resource(s) 2503. The computing resource(s) 2503 are separate from the portable device 2530. Likewise, the computing resource(s) 2503 may be configured to communicate over the network 2502 with the portable device 2530 and/or other external computing resources, data stores, etc.

As illustrated, the computing resource(s) 2503 may be remote from the portable device 2530 and implemented as one or more servers 2503(1), 2503(2), . . . , 2503(P) and may, in some instances, form a portion of a network-accessible computing platform implemented as a computing infrastructure of processors, storage, software, data access, and so forth that is maintained and accessible by components/devices of the 3D body model system 2501 and/or the portable device 2530 via the network 2502, such as an intranet (e.g., local area network), the Internet, etc. The computing resources 2503, which may include one or more neural network, may process one or more 2D body direction images representative of a body of a user, generate therefrom personalized 3D body parameters and/or body measurements, and send those personalized 3D body parameters and/or body measurements to the portable device 2530. In other implementations, some or all of the 3D body model system 2501 may be included or incorporated on the portable device, as illustrated.

The computing resource(s) 2503 do not require end-user knowledge of the physical location and configuration of the system that delivers the services. Common expressions associated for these remote computing resource(s) 2503 include "on-demand computing," "software as a service (SaaS)," "platform computing," "network-accessible platform," "cloud services," "data centers," and so forth. Each of the servers 2503(1)-(P) include a processor 2517 and memory 2519, which may store or otherwise have access to a 3D body model system 2501.

The network 2502 may be any wired network, wireless network, or combination thereof, and may comprise the Internet in whole or in part. In addition, the network 2502 may be a personal area network, local area network, wide area network, cable network, satellite network, cellular telephone network, or combination thereof. The network 2502 may also be a publicly accessible network of linked networks, possibly operated by various distinct parties, such as the Internet. In some implementations, the network 2502 may be a private or semi-private network, such as a corporate or university intranet. The network 2502 may include one or more wireless networks, such as a Global System for Mobile Communications (GSM) network, a Code Division Multiple Access (CDMA) network, a Long Term Evolution (LTE) network, or some other type of wireless network. Protocols and components for communicating via the Internet or any of the other aforementioned types of communication networks are well known to those skilled in the art of computer communications and thus, need not be described in more detail herein.

The computers, servers, devices and the like described herein have the necessary electronics, software, memory, storage, databases, firmware, logic/state machines, microprocessors, communication links, displays or other visual or audio user interfaces, printing devices, and any other input/output interfaces to provide any of the functions or services described herein and/or achieve the results described herein. Also, those of ordinary skill in the pertinent art will recognize that users of such computers, servers, devices and the like may operate a keyboard, keypad, mouse, stylus, touch screen, or other device (not shown) or method to interact with the computers, servers, devices and the like, or to "select" an item, personalized 3D body model, body measurements, and/or any other aspect of the present disclosure.

The 3D body model system 2501, the application 2525, and/or the portable device 2530 may use any web-enabled or Internet applications or features, or any other client-server applications or features including E-mail or other messaging techniques, to connect to the network 2502, or to communicate with one another, such as through short or multimedia messaging service (SMS or MMS) text messages. For example, the servers 2503-1, 2503-2 . . . 2503-P may be adapted to transmit information or data in the form of synchronous or asynchronous messages from the 3D body model system 2501 to the processor 2526 or other components of the portable device 2530, or any other computer device in real time or in near-real time, or in one or more offline processes, via the network 2502. Those of ordinary skill in the pertinent art would recognize that the 3D body model system 2501 may operate any of a number of computing devices that are capable of communicating over the network, including but not limited to set-top boxes, personal digital assistants, digital media players, web pads, laptop computers, desktop computers, electronic book readers, cellular phones, and the like. The protocols and components for providing communication between such devices are well known to those skilled in the art of computer communications and need not be described in more detail herein.

The data and/or computer executable instructions, programs, firmware, software and the like (also referred to herein as "computer executable" components) described herein may be stored on a computer-readable medium that is within or accessible by computers or computer components such as the servers 2503-1, 2503-2 . . . 2503-P, the processor 2526, or any other computers or control systems utilized by the application 2525, the 3D body model system 2501, and/or the portable device 2530, and having sequences of instructions which, when executed by a processor (e.g., a central processing unit, or "CPU"), cause the processor to perform all or a portion of the functions, services and/or methods described herein. Such computer executable instructions, programs, software and the like may be loaded into the memory of one or more computers using a drive mechanism associated with the computer readable medium, such as a floppy drive, CD-ROM drive, DVD-ROM drive, network interface, or the like, or via external connections.

Some implementations of the systems and methods of the present disclosure may also be provided as a computer-executable program product including a non-transitory machine-readable storage medium having stored thereon instructions (in compressed or uncompressed form) that may be used to program a computer (or other electronic device) to perform processes or methods described herein. The machine-readable storage media of the present disclosure may include, but is not limited to, hard drives, floppy diskettes, optical disks, CD-ROMs, DVDs, ROMs, RAMs, erasable programmable ROMs ("EPROM"), electrically erasable programmable ROMs ("EEPROM"), flash memory, magnetic or optical cards, solid-state memory devices, or other types of media/machine-readable medium that may be suitable for storing electronic instructions. Further, implementations may also be provided as a computer executable program product that includes a transitory machine-readable signal (in compressed or uncompressed form). Examples of machine-readable signals, whether modulated using a carrier or not, may include, but are not limited to, signals that a computer system or machine hosting or running a computer program can be configured to access, or including signals that may be downloaded through the Internet or other networks.

Although the disclosure has been described herein using exemplary techniques, components, and/or processes for implementing the systems and methods of the present disclosure, it should be understood by those skilled in the art that other techniques, components, and/or processes or other combinations and sequences of the techniques, components, and/or processes described herein may be used or performed that achieve the same function(s) and/or result(s) described herein and which are included within the scope of the present disclosure.

Additionally, in accordance with the present disclosure, the training of machine learning tools (e.g., artificial neural networks or other classifiers) and the use of the trained machine learning tools to detect body pose, determine body point locations, determined body direction, and/or to generate personalized 3D body models of a body based on one or more 2D body images of that body may occur on multiple, distributed computing devices, or on a single computing device, as described herein.

Likewise, while the above discussions focus primarily on a personalized 3D body model of a body being generated from multiple 2D body direction images, in some implementations, the personalized 3D body model may be generated based on a single 2D body direction image of the body. In other implementations, two or more 2D direction body images may be used with the disclosed implementations. Likewise, a single 2D body direction image, such as a front view image, may be used to determine body measurements. In general, the more 2D body direction images, the more accurate the final representation and dimensions of the personalized 3D body model may be.

Still further, while the above implementations are described with respect generating personalized 3D body models of human bodies represented in 2D body images, in other implementations, non-human bodies, such as dogs, cats, or other animals may be modeled in 3D based on 2D images of those bodies. Accordingly, the use of a human body in the disclosed implementations should not be considered limiting.

It should be understood that, unless otherwise explicitly or implicitly indicated herein, any of the features, characteristics, alternatives or modifications described regarding a particular implementation herein may also be applied, used, or incorporated with any other implementation described herein, and that the drawings and detailed description of the present disclosure are intended to cover all modifications, equivalents and alternatives to the various implementations as defined by the appended claims. Moreover, with respect to the one or more methods or processes of the present disclosure described herein, including but not limited to the flow charts shown in FIGS. 4 through 7, 11, 12A, 12B, 15, 17, and 19 through 24, orders in which such methods or processes are presented are not intended to be construed as any limitation on the claimed inventions, and any number of the method or process steps or boxes described herein can be combined in any order and/or in parallel to implement the methods or processes described herein. Also, the drawings herein are not drawn to scale.

Conditional language, such as, among others, "can," "could," "might," or "may," unless specifically stated otherwise, or otherwise understood within the context as used, is generally intended to convey in a permissive manner that certain implementations could include, or have the potential to include, but do not mandate or require, certain features, elements and/or steps. In a similar manner, terms such as "include," "including" and "includes" are generally intended to mean "including, but not limited to." Thus, such conditional language is not generally intended to imply that features, elements and/or steps are in any way required for one or more implementations or that one or more implementations necessarily include logic for deciding, with or without user input or prompting, whether these features, elements and/or steps are included or are to be performed in any particular implementation.

The elements of a method, process, or algorithm described in connection with the implementations disclosed herein can be embodied directly in hardware, in a software module stored in one or more memory devices and executed by one or more processors, or in a combination of the two. A software module can reside in RAM, flash memory, ROM, EPROM, EEPROM, registers, a hard disk, a removable disk, a CD-ROM, a DVD-ROM or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Disjunctive language such as the phrase "at least one of X, Y, or Z," or "at least one of X, Y and Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain implementations require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Language of degree used herein, such as the terms "about," "approximately," "generally," "nearly" or "substantially" as used herein, represent a value, amount, or characteristic close to the stated value, amount, or characteristic that still performs a desired function or achieves a desired result. For example, the terms "about," "approximately," "generally," "nearly" or "substantially" may refer to an amount that is within less than 10% of, within less than 5% of, within less than 1% of, within less than 0.1% of, and within less than 0.01% of the stated amount.

Although the invention has been described and illustrated with respect to illustrative implementations thereof, the foregoing and various other additions and omissions may be made therein and thereto without departing from the spirit and scope of the present disclosure.

What is claimed is:

1. A computer-implemented method, comprising:
receiving personalized three-dimensional ("3D") body parameters corresponding to a body at a current body measurement value;
receiving non-personalized 3D body parameters corresponding to the body;
receiving predicted non-personalized 3D body parameters corresponding to a target body measurement value for the body;
determining one or more deltas between the predicted non-personalized 3D body parameters and the non-personalized 3D body parameters;
generating, based at least in part on the predicted non-personalized 3D body parameters and the one or more deltas, a predicted personalized 3D body model of the body, the predicted personalized 3D body model representative of a predicted appearance of the body at the target body measurement value;
determining if the one or more deltas exceed a threshold; and
in response to determining that the one or more deltas exceed the threshold:
applying a generic texture and a generic shading to the predicted personalized 3D body model; and
presenting, on a display, the predicted personalized 3D body model with the generic texture and shading.

2. The computer-implemented method of claim 1, further comprising:
in response to determining that the one or more deltas do not exceed the threshold:
modifying at least one of a texture or a shading from a personalized 3D body model based at least in part on the one or more deltas;
applying at least one of the modified texture or the modified shading to the predicted personalized 3D body model; and
presenting, on the display, the predicted personalized 3D body model with the applied at least one of the modified texture or the modified shading.

3. The computer-implemented method of claim 1, further comprising:
determining at least one of a texture or a clothing to apply to the predicted personalized 3D body model;
adjusting the at least one of the texture or the clothing to correspond to predicted personalized 3D body parameters corresponding to the predicted personalized 3D body model to produce at least one of an adjusted texture or an adjusted clothing; and
applying to the predicted personalized 3D body model, at least one of the adjusted texture or the adjusted clothing,
wherein the predicted personalized 3D body model presented on the display includes the at least one of the applied adjusted texture or the applied adjusted clothing.

4. The computer-implemented method of claim 1, further comprising:
integrating at least a personalized 3D body model and the predicted personalized 3D body model to produce a 3D body model adjustor that includes a plurality of personalized 3D body models representative of predicted appearances of the body between the personalized 3D body model and the predicted personalized 3D body model.

5. A computing system, comprising:
one or more processors; and
a memory storing program instructions that, when executed by the one or more processors, cause the one or more processors to at least:
  determine one or more deltas between predicted non-personalized 3D body parameters corresponding to a body and non-personalized 3D body parameters;
  generate, based at least in part on predicted personalized 3D body parameters corresponding to the body and the one or more deltas, a predicted personalized 3D body model of the body, the predicted personalized 3D body model representative of a predicted appearance of the body at a target body measurement value;
  determine if the one or more deltas exceed a threshold; and
  in response to a determination that the one or more deltas do not exceed the threshold:
    apply at least one of a texture or a shading from a personalized 3D body model to the predicted personalized 3D body model; and
    present, on a display, the predicted personalized 3D body model.

6. The computing system of claim 5, wherein the program instructions, when executed by the one or more processors, further cause the one or more processors to at least:
  in response to a determination that the one or more deltas exceed the threshold:
    apply at least one of a generic texture or a generic shading to the predicted personalized 3D body model; and
    present, on the display, the predicted personalized 3D body model with the generic texture or the generic shading.

7. The computing system of claim 6, wherein the program instructions, when executed by the one or more processors, further cause the one or more processors to at least:
  determine at least one of a texture or a clothing to apply to the predicted personalized 3D body model;
  adjust the at least one of the texture or the clothing to correspond to the predicted personalized 3D body parameters to produce at least one of an adjusted texture or an adjusted clothing; and
  apply to the predicted personalized 3D body model, the at least one of the adjusted texture or the adjusted clothing,
  wherein the predicted personalized 3D body model presented on the display includes the at least one of the applied adjusted texture or the applied adjusted clothing.

8. The computing system of claim 6, wherein the program instructions, when executed by the one or more processors, further cause the one or more processors to at least:
  determine the target body measurement value for a body measurement of the body; and
  determine, based at least in part on the target body measurement value, the predicted personalized 3D body parameters corresponding to the predicted appearance of the body with the target body measurement value.

9. The computing system of claim 5, wherein the target body measurement value is at least one of a weight of the body, a body fat measurement value of the body, or a muscle mass of the body.

10. The computing system of claim 5, wherein the program instructions, when executed by the one or more processors, further cause the one or more processors to at least:
  generate a personalized 3D body model of the body based at least in part on personalized 3D body parameters, wherein the personalized 3D body model is different than the predicted personalized 3D body model.

11. The computing system of claim 5, wherein the program instructions, when executed by the one or more processors to generate the predicted personalized 3D body model of the body, further include instructions that, when executed by the one or more processors, further cause the one or more processors to at least:
  determine, using one or more neural networks, predicted personalized 3D body parameters for the body with the target body measurement value; and
  generate the predicted personalized 3D body model based at least in part on the predicted personalized 3D body parameters.

12. The computing system of claim 11, wherein the program instructions, when executed by the one or more processors, further cause the one or more processors to at least:
  determine historical personalized 3D body parameters for the body, the historical personalized 3D body parameters indicative of actual personalized 3D body parameters of the body at prior points in time;
  determine, based at least in part on the historical personalized 3D body parameters, personalized 3D body parameter changes indicative of actual body parameter changes of the body; and
  altering the one or more neural networks based at least in part on the historical personalized 3D body parameters.

13. The computing system of claim 5, wherein the program instructions, when executed by the one or more processors, further cause the one or more processors to at least:
  determine that a plurality of historical personalized 3D body parameters for the body are known;
  determine, for the body and based at least in part on the plurality of historical personalized 3D body parameters, changes in personalized 3D body parameters; and
  select a neural network based at least in part on the changes, wherein the neural network is used to generate the predicted personalized 3D body parameters.

14. The computing system of claim 5, wherein the program instructions that, when executed by the one or more processors, further cause the one or more processors to at least:
  receive an activity target indicative of a change in at least one activity type for the body; and
  select, based at least in part on the activity type, a neural network, wherein the neural network determines the predicted personalized 3D body parameters.

15. The computing system of claim 14, wherein:
  the activity type is at least one of a cardio activity or a weightlifting activity; and
  the neural network is selected based on training data corresponding to the cardio activity or the weightlifting activity and representative of body model changes resultant from the cardio activity or the weightlifting activity.

16. A method, comprising:
  determining one or more deltas between predicted non-personalized 3D body parameters corresponding to a body with a target body measurement value and non-personalized 3D body parameters;

determining, using one or more neural networks, predicted personalized 3D body parameters for the body with the target body measurement value;

generating, based at least in part on the predicted personalized 3D body parameters, a predicted personalized 3D body model representative of a predicted appearance of the body with the target body measurement value;

determining if the one or more deltas exceed a threshold; and in response to determining that the one or more deltas do not exceed the threshold:
  applying at least one of a texture or a shading from a personalized 3D body model of the body to the predicted personalized 3D body model; and
  presenting, on a display, the predicted personalized 3D body model with the applied at least one of the texture or the shading.

17. The method of claim 16, further comprising:
applying the one or more deltas to personalized 3D body parameters to produce the predicted personalized 3D body parameters.

18. The method of claim 16, further comprising:
determining historical personalized 3D body parameters for the body, the historical personalized 3D body parameters indicative of actual personalized 3D body parameters of the body at prior points in time;

determining, based at least in part on the historical personalized 3D body parameters, personalized 3D body parameter changes indicative of actual body parameter changes of the body; and altering the one or more neural networks based at least in part on the historical personalized 3D body parameters.

19. The method of claim 16, further comprising:
determining at least one of a texture or a clothing to apply to the predicted personalized 3D body model;

adjusting the at least one of the texture or the clothing to correspond to the predicted personalized 3D body parameters to produce at least one of an adjusted texture or an adjusted clothing; and applying to the predicted personalized 3D body model, the at least one of the adjusted texture or the adjusted clothing, wherein the predicted personalized 3D body model presented on the display includes the at least one of the applied adjusted texture or the applied adjusted clothing.

20. The method of claim 19, further comprising:
in response to determining that the one or more deltas exceed the threshold:
  applying at least one of a generic texture or a generic shading to the predicted personalized 3D body model; and
  presenting, on the display, the predicted personalized 3D body model with the generic texture or the generic shading.

* * * * *